United States Patent
Marsot et al.

(10) Patent No.: US 8,282,576 B2
(45) Date of Patent: *Oct. 9, 2012

(54) METHOD AND APPARATUS FOR AN IMPROVED SAMPLE CAPTURE DEVICE

(75) Inventors: Travis Marsot, Mountain View, CA (US); Paul Lum, Los Altos, CA (US); Don Alden, Sunnyvale, CA (US); James Ross, Livermore, CA (US); Ron L. Bardell, Minneapolis, MN (US); Bernhard Weigl, Seattle, WA (US)

(73) Assignee: Sanofi-Aventis Deutschland GmbH, Franfurt am Main (DE)

( * ) Notice: Subject to any disclaimer, the term of this patent is extended or adjusted under 35 U.S.C. 154(b) by 563 days.

This patent is subject to a terminal disclaimer.

(21) Appl. No.: 10/574,242

(22) PCT Filed: Sep. 29, 2004

(86) PCT No.: PCT/US2004/032025
§ 371 (c)(1), (2), (4) Date: Feb. 9, 2009

(87) PCT Pub. No.: WO2005/033659
PCT Pub. Date: Apr. 14, 2005

(65) Prior Publication Data
US 2009/0204025 A1    Aug. 13, 2009

(51) Int. Cl.
*A61B 5/00* (2006.01)
*A61B 17/14* (2006.01)
*A61B 17/32* (2006.01)

(52) U.S. Cl. .......................... 600/583; 606/183

(58) Field of Classification Search ................ 600/583, 600/584; 606/181–183; 382/128; 204/403.01
See application file for complete search history.

(56) References Cited

U.S. PATENT DOCUMENTS

| 2,061 A | 4/1841 | Osdel ................ 606/182 |
| 55,620 A | 6/1866 | Capewell ............ 606/181 |
| 657,416 A | 9/1900 | Haviland ............... 435/4 |
| 1,135,465 A | 4/1915 | Pollock .............. 606/181 |
| 1,733,847 A | 10/1929 | Wilmot ............... 292/332 |
| 2,258,857 A | 10/1941 | McCann .............. 601/81 |
| 2,628,319 A | 2/1953 | Vang ................ 310/15 |

(Continued)

FOREIGN PATENT DOCUMENTS

DE      4420232      12/1995

(Continued)

OTHER PUBLICATIONS

Wolfbeis et al. (Sol-gel based glucose biosensors employing optical oxygen transducers, and a method for compensating for variable oxygen background, Biosensors & Bioelectronics 15 (2000) pp. 69-76).

(Continued)

*Primary Examiner* — Brian Szmal
(74) *Attorney, Agent, or Firm* — Paul Davis; Goodwin Procter LLP

(57) ABSTRACT

A body fluid sampling device is provided. A mesh may be used to guide blood or fluid to travel directly from the wound to an analyte detecting port on the cartridge. Thus the volume of blood or body fluid produced at the wound site irregardless of its droplet geometry can be reliable and substantially completely transported to the analyte detecting member for measurement.

14 Claims, 24 Drawing Sheets

U.S. PATENT DOCUMENTS

| | | | |
|---|---|---|---|
| 2,714,890 A | 8/1955 | Alfred | 606/169 |
| 2,763,935 A | 9/1956 | Whaley | 33/511 |
| 2,801,633 A | 8/1957 | Ehrlich | 606/181 |
| 2,880,876 A | 4/1959 | Dujardin | 210/523 |
| 3,046,987 A | 7/1962 | Ehrlich | 128/314 |
| 3,030,959 A | 9/1962 | Grunert | 128/329 |
| 3,086,288 A | 4/1963 | Balamuth | 30/277.4 |
| 3,090,384 A | 5/1963 | Baldwin et al. | 604/272 |
| 3,208,452 A | 9/1965 | Stern | 606/182 |
| 3,358,689 A | 12/1967 | Higgins | 128/329 |
| 3,412,729 A | 11/1968 | Smith, Jr. | 128/2.05 |
| 3,448,307 A | 6/1969 | Rudolph | 310/23 |
| 3,494,358 A | 2/1970 | Grossenbacher | 128/218 |
| 3,620,209 A | 11/1971 | Kravitz | 601/79 |
| 3,626,929 A | 12/1971 | Sanz | 128/2 R |
| 3,628,026 A | 12/1971 | Cronin | 250/214.1 |
| 3,665,672 A | 5/1972 | Speelman | 53/435 |
| 3,673,475 A | 6/1972 | Britton | 318/122 |
| 3,712,293 A | 1/1973 | Mielke, Jr. | 128/2 G |
| 3,734,812 A | 5/1973 | Yazawa | 428/107 |
| 3,742,954 A | 7/1973 | Strickland | 128/302 |
| 3,780,960 A | 12/1973 | Tokuno | 242/555.2 |
| 3,832,776 A | 9/1974 | Sawyer | 30/272 |
| 3,836,148 A | 9/1974 | Manning | 273/368 |
| 3,851,543 A | 12/1974 | Krom | 74/493 |
| 3,853,010 A | 12/1974 | Christen | 73/864.24 |
| 3,924,818 A | 12/1975 | Pfeifle | 242/364.7 |
| 3,938,526 A | 2/1976 | Anderson | 128/303.1 |
| 3,953,172 A | 4/1976 | Shapiro | 23/230 |
| 3,971,365 A | 7/1976 | Smith | 128/2.17 |
| 4,057,394 A | 11/1977 | Genshaw | 23/230 |
| 4,077,406 A | 3/1978 | Sandhage | 604/61 |
| 4,109,655 A | 8/1978 | Chaconac | 128/253 |
| 4,139,011 A | 2/1979 | Benoit | 606/182 |
| 4,154,228 A | 5/1979 | Feldstein | 606/169 |
| 4,168,130 A | 9/1979 | Barth | 404/99 |
| 4,184,486 A | 1/1980 | Papa | 600/373 |
| 4,190,420 A | 2/1980 | Covington | 422/63 |
| 4,191,193 A | 3/1980 | Seo | 600/488 |
| 4,193,690 A | 3/1980 | Levenson | 356/301 |
| 4,203,446 A | 5/1980 | Hofert | 606/182 |
| 4,207,870 A | 6/1980 | Eldridge | 128/766 |
| 4,223,674 A | 9/1980 | Fluent | 604/504 |
| 4,224,125 A | 9/1980 | Nakamura | 204/195 B |
| 4,224,949 A | 9/1980 | Scott | 128/734 |
| 4,230,118 A | 10/1980 | Holman et al. | 128/314 |
| 4,240,439 A | 12/1980 | Abe | 600/412 |
| 4,254,083 A | 3/1981 | Columbus | 422/55 |
| 4,258,001 A | 3/1981 | Pierce | 422/56 |
| 4,259,653 A | 3/1981 | McGonigal | 310/15 |
| 4,299,230 A | 11/1981 | Kubota | 600/300 |
| 4,301,412 A | 11/1981 | Hill | 324/442 |
| 4,321,397 A | 3/1982 | Nix | 548/366 |
| 4,338,174 A | 7/1982 | Tamura | 204/195 |
| 4,340,669 A | 7/1982 | Bauer | 435/14 |
| 4,350,762 A | 9/1982 | De Luca | 435/10 |
| 4,353,984 A | 10/1982 | Yamada | 435/14 |
| 4,356,826 A | 11/1982 | Kubota | 600/300 |
| 4,360,016 A | 11/1982 | Sarrine | 128/763 |
| 4,388,922 A | 6/1983 | Telang | 604/319 |
| 4,391,905 A | 7/1983 | Bauer | 435/14 |
| 4,391,906 A | 7/1983 | Bauer | 435/14 |
| 4,392,933 A | 7/1983 | Nakamura | 204/403.14 |
| 4,394,512 A | 7/1983 | Batz | 548/365 |
| 4,397,556 A | 8/1983 | Muller | 356/301 |
| 4,407,008 A | 9/1983 | Schmidt | 356/301 |
| 4,411,266 A | 10/1983 | Cosman | 128/303.18 |
| 4,414,975 A | 11/1983 | Ryder | 128/314 |
| 4,418,037 A | 11/1983 | Katsuyama | 422/56 |
| 4,420,564 A | 12/1983 | Tsuji | 435/288 |
| 4,425,039 A | 1/1984 | Grant | 356/35.5 |
| 4,426,451 A | 1/1984 | Columbus | 436/518 |
| 4,426,884 A | 1/1984 | Polchaninoff | 73/172 |
| 4,440,301 A | 4/1984 | Intengan | 206/456 |
| 4,442,836 A | 4/1984 | Meinecke | 128/314 |
| 4,442,972 A | 4/1984 | Sahay | 236/1 EA |
| 4,449,529 A | 5/1984 | Burns | 606/182 |
| 4,462,405 A | 7/1984 | Ehrlich | 606/182 |
| 4,469,110 A | 9/1984 | Slama | 128/770 |
| 4,517,978 A | 5/1985 | Levin | 128/314 |
| 4,518,384 A | 5/1985 | Tarello | 604/61 |
| 4,523,994 A | 6/1985 | Shono | 549/352 |
| 4,535,769 A | 8/1985 | Burns | 128/314 |
| 4,535,773 A | 8/1985 | Yoon | 606/185 |
| 4,537,197 A | 8/1985 | Hulka | 128/633 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,561,445 A | 12/1985 | Berke | 128/642 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,586,819 A | 5/1986 | Tochigi | 356/301 |
| 4,586,926 A | 5/1986 | Osborne | 604/272 |
| 4,590,411 A | 5/1986 | Kelly | 318/687 |
| 4,595,479 A | 6/1986 | Kimura | 204/294 |
| 4,600,014 A | 7/1986 | Beraha | 128/754 |
| 4,603,209 A | 7/1986 | Tsien | 549/352 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia | 600/583 |
| 4,637,393 A | 1/1987 | Ray | 128/305 |
| 4,637,403 A | 1/1987 | Garcia | 600/583 |
| 4,643,189 A | 2/1987 | Mintz | 128/314 |
| 4,648,408 A | 3/1987 | Hutcheson | 128/770 |
| 4,648,714 A | 3/1987 | Benner | 356/301 |
| 4,653,511 A | 3/1987 | Goch | 128/763 |
| 4,653,513 A | 3/1987 | Dombrowski | 600/578 |
| 4,655,225 A | 4/1987 | Dahne | 600/316 |
| 4,661,768 A | 4/1987 | Carusillo | 324/678 |
| 4,666,438 A | 5/1987 | Raulerson | 604/272 |
| 4,676,244 A | 6/1987 | Enstrom | 128/314 |
| 4,677,979 A | 7/1987 | Burns | 128/314 |
| 4,678,277 A | 7/1987 | Delhaye | 356/301 |
| 4,682,892 A | 7/1987 | Chawla | 356/353 |
| 4,702,594 A | 10/1987 | Grant | 356/35.5 |
| 4,711,245 A | 12/1987 | Higgins | 128/635 |
| 4,712,460 A | 12/1987 | Allen | 83/208 |
| 4,712,548 A | 12/1987 | Enstrom | 128/314 |
| 4,714,462 A | 12/1987 | DiDomenico | 604/67 |
| 4,715,374 A | 12/1987 | Maggio | 128/314 |
| 4,731,330 A | 3/1988 | Hilll | 436/16 |
| 4,731,726 A | 3/1988 | Allen, III | 600/300 |
| 4,734,360 A | 3/1988 | Phillips | 435/25 |
| 4,735,203 A | 4/1988 | Ryder | 128/314 |
| 4,737,458 A | 4/1988 | Batz | 435/28 |
| 4,750,489 A | 6/1988 | Berkman | 606/166 |
| 4,753,776 A | 6/1988 | Hillman | 422/101 |
| 4,756,884 A | 7/1988 | Hillman | 422/73 |
| 4,757,022 A | 7/1988 | Shults | 204/403.05 |
| 4,758,323 A | 7/1988 | Davis | 204/403 |
| 4,774,192 A | 9/1988 | Teriniello | 436/530 |
| 4,784,486 A | 11/1988 | Van Wagenen | 356/301 |
| 4,787,398 A | 11/1988 | Garcia | 600/583 |
| 4,790,979 A | 12/1988 | Teriniello | 422/56 |
| 4,794,926 A | 1/1989 | Munsch et al. | 606/183 |
| 4,797,283 A | 1/1989 | Allen | 424/443 |
| 4,814,142 A | 3/1989 | Gleisner | 422/56 |
| 4,814,661 A | 3/1989 | Ratzlaff | 310/328 |
| 4,817,603 A | 4/1989 | Turner | 606/182 |
| 4,818,493 A | 4/1989 | Coville | 422/102 |
| 4,820,010 A | 4/1989 | Sciefres | 385/43 |
| 4,820,399 A | 4/1989 | Senda | 204/403 |
| 4,823,806 A | 4/1989 | Bajada | 600/557 |
| 4,824,639 A | 4/1989 | Hildenbrand | 422/56 |
| RE32,922 E | 5/1989 | Levin | 128/314 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeill | 435/53 |
| 4,836,904 A | 6/1989 | Armstrong | 204/294 |
| 4,840,893 A | 6/1989 | Hill | 435/6 |
| 4,844,095 A | 7/1989 | Chiodo | 128/314 |

| Patent No. | Date | Name | Ref. |
|---|---|---|---|
| 4,845,392 A | 7/1989 | Mumbower | 310/14 |
| 4,850,973 A | 7/1989 | Jordan | 604/157 |
| 4,857,274 A | 8/1989 | Simon | 422/72 |
| 469,265 A | 9/1989 | McEwen | 128/774 |
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |
| 4,897,173 A | 1/1990 | Nankai | 204/403 |
| 4,900,424 A | 2/1990 | Birch | 204/409 |
| 4,900,666 A | 2/1990 | Phillips | 435/25 |
| 4,911,794 A | 3/1990 | Parce | 204/1 T |
| 4,920,977 A | 5/1990 | Haynes | 128/770 |
| 4,924,879 A | 5/1990 | O'brien | 600/583 |
| 4,935,346 A | 6/1990 | Phillips | 435/14 |
| 4,938,218 A | 7/1990 | Goodman | 128/633 |
| 4,940,468 A | 7/1990 | Petillo | 606/170 |
| 4,944,304 A | 7/1990 | Nishina | 128/667 |
| 4,945,045 A | 7/1990 | Forrest | 435/25 |
| 4,946,795 A | 8/1990 | Gibbons | 436/179 |
| 4,948,727 A | 8/1990 | Cass | 435/18 |
| 4,948,961 A | 8/1990 | Hillman | 250/252.1 |
| 4,952,373 A | 8/1990 | Sugarman | 422/99 |
| 4,952,515 A | 8/1990 | Gleisner | 436/169 |
| 4,953,552 A | 9/1990 | DeMarzo | 128/633 |
| 4,953,976 A | 9/1990 | Adler-Golden | 356/301 |
| 4,963,498 A | 10/1990 | Hillman | 436/69 |
| 4,966,581 A | 10/1990 | Landau | 604/72 |
| 4,966,646 A | 10/1990 | Zdeblick | 156/633 |
| 4,966,671 A | 10/1990 | Nylander | 204/153.14 |
| 4,975,581 A | 12/1990 | Robinson | 250/339 |
| 4,976,724 A | 12/1990 | Nieto | 606/182 |
| 4,977,910 A | 12/1990 | Miyahara | 134/7 |
| 4,983,178 A | 1/1991 | Schnell | 606/181 |
| 4,984,085 A | 1/1991 | Landowski | 358/213 |
| 4,990,154 A | 2/1991 | Brown | 606/182 |
| 4,995,402 A | 2/1991 | Smith | 600/584 |
| 4,999,582 A | 3/1991 | Parks | 324/438 |
| 5,001,054 A | 3/1991 | Wagner | 435/14 |
| 5,001,873 A | 3/1991 | Rufin | 451/39 |
| 5,004,923 A | 4/1991 | Hillman | 250/341 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| D318,331 S | 7/1991 | Phillips | D24/169 |
| 5,028,142 A | 7/1991 | Ostoich | 366/273 |
| 5,029,583 A | 7/1991 | Meserol | 600/316 |
| 5,035,704 A | 7/1991 | Lambert | 606/182 |
| 5,039,617 A | 8/1991 | McDonald | 436/69 |
| 5,043,143 A | 8/1991 | Shaw | 422/65 |
| 5,046,496 A | 9/1991 | Betts | 600/352 |
| 5,047,044 A | 9/1991 | Smith | 606/182 |
| 5,049,373 A | 9/1991 | Ballou | 549/352 |
| 5,049,487 A | 9/1991 | Phillips | 435/4 |
| 5,054,487 A | 10/1991 | Clarke | 128/633 |
| 5,054,499 A | 10/1991 | Swierczek | 128/770 |
| 5,057,082 A | 10/1991 | Burchette, Jr. | 604/164 |
| 5,057,277 A | 10/1991 | Mauze | 422/56 |
| 5,059,394 A | 10/1991 | Phillips | 422/68.1 |
| 5,059,789 A | 10/1991 | Salcudean | 250/206.1 |
| 5,060,174 A | 10/1991 | Gross | 702/139 |
| 5,062,898 A | 11/1991 | McDermott | 134/7 |
| 5,064,411 A | 11/1991 | Gordon, III | 604/48 |
| 5,070,874 A | 12/1991 | Barnes | 128/633 |
| 5,070,886 A | 12/1991 | Mitchen | 128/771 |
| 5,074,872 A | 12/1991 | Brown | 606/182 |
| 5,077,017 A | 12/1991 | Gorin | 422/100 |
| 5,077,199 A | 12/1991 | Basagni | 435/14 |
| 5,080,865 A | 1/1992 | Leiner | 422/68.1 |
| 5,086,229 A | 2/1992 | Rosenthal | 250/341 |
| 5,089,112 A | 2/1992 | Skotheim | 204/403 |
| 5,092,842 A | 3/1992 | Bechtold | 604/135 |
| 5,094,943 A | 3/1992 | Siedel | 435/25 |
| 5,096,669 A | 3/1992 | Lauks | 204/403.02 |
| 5,097,810 A | 3/1992 | Fishman | 600/556 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,382 A | 4/1992 | Brinkerhoff et al. | 604/164.12 |
| 5,104,619 A | 4/1992 | Castro | 422/56 |
| 5,104,813 A | 4/1992 | Besemer | 436/179 |
| 5,107,764 A | 4/1992 | Gasparrini | 101/425 |
| 5,108,564 A | 4/1992 | Szuminsky | 204/153.12 |
| 5,108,889 A | 4/1992 | Smith | 435/4 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,132,801 A | 7/1992 | Yamano | 358/213 |
| 5,133,730 A | 7/1992 | Biro | 606/182 |
| 5,135,719 A | 8/1992 | Hillman | 422/101 |
| 5,139,685 A | 8/1992 | Castro | 210/767 |
| 5,140,161 A | 8/1992 | Hillman | 250/341 |
| 5,141,868 A | 8/1992 | Shanks | 435/288 |
| 5,144,139 A | 9/1992 | Hillman | 250/341 |
| 5,145,565 A | 9/1992 | Kater | 600/341 |
| 5,146,091 A | 9/1992 | Knudson | 250/341.6 |
| 5,152,296 A | 10/1992 | Simons | 128/670 |
| 5,152,775 A | 10/1992 | Ruppert | 606/182 |
| 5,153,671 A | 10/1992 | Miles | 356/301 |
| 5,156,611 A | 10/1992 | Haynes | 606/181 |
| 5,162,525 A | 11/1992 | Masilamani | 549/352 |
| 5,163,442 A | 11/1992 | Ono | 128/760 |
| 5,164,598 A | 11/1992 | Hillman | 250/341 |
| 5,167,619 A | 12/1992 | Wuchinich | 604/22 |
| 5,170,364 A | 12/1992 | Gross | 702/139 |
| 5,174,726 A | 12/1992 | Findlay | 417/205 |
| D332,490 S | 1/1993 | Brown | D24/146 |
| 5,178,142 A | 1/1993 | Harjunmaa | 128/633 |
| 5,179,005 A | 1/1993 | Phillips | 435/14 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,188,118 A | 2/1993 | Terwilliger | 600/566 |
| 5,189,751 A | 3/1993 | Giuliani | 15/22.1 |
| 5,192,415 A | 3/1993 | Yoshioka | 204/403 |
| 5,194,391 A | 3/1993 | Mauze | 436/166 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,209,028 A | 5/1993 | McDermott | 51/426 |
| 5,211,652 A | 5/1993 | Derbyshire | 606/182 |
| 5,212,879 A | 5/1993 | Biro | 29/437 |
| 5,215,587 A | 6/1993 | McConnellogue | 118/699 |
| 5,216,597 A | 6/1993 | Beckers | 364/413.02 |
| 5,217,476 A | 6/1993 | Wishinsky | 606/167 |
| 5,217,480 A | 6/1993 | Haber | 606/182 |
| 5,218,966 A | 6/1993 | Yamasawa | 600/499 |
| 5,222,504 A | 6/1993 | Solomon | 600/557 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,241,969 A | 9/1993 | Carson | 600/566 |
| 5,247,932 A | 9/1993 | Chung | 128/633 |
| 5,249,583 A | 10/1993 | Mallaby | 600/567 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |

| Patent No. | Date | Inventor | Class |
|---|---|---|---|
| 5,266,179 A | 11/1993 | Nankai | 204/401 |
| 5,266,359 A | 11/1993 | Spielvogel | 427/388.4 |
| D342,573 S | 12/1993 | Cerola | D24/147 |
| 5,267,974 A | 12/1993 | Lambert | 604/195 |
| 5,272,087 A | 12/1993 | El Murr | 435/291 |
| 5,277,181 A | 1/1994 | Mendelson | 128/633 |
| 5,279,294 A | 1/1994 | Anderson | 600/322 |
| 5,279,791 A | 1/1994 | Aldrich | 422/58 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollmann | 435/288 |
| 5,294,261 A | 3/1994 | McDermott | 134/7 |
| 5,296,378 A | 3/1994 | Sakata | 436/63 |
| 5,300,779 A | 4/1994 | Hillman | 250/341 |
| 5,304,192 A | 4/1994 | Crouse | 606/181 |
| 5,304,193 A | 4/1994 | Zhadanov | 606/182 |
| 5,304,347 A | 4/1994 | Mann | 422/67 |
| 5,304,468 A | 4/1994 | Phillips | 435/14 |
| 5,306,623 A | 4/1994 | Kiser | 435/14 |
| 5,307,263 A | 4/1994 | Brown | 600/301 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,315,793 A | 5/1994 | Peterson | 451/2 |
| 5,316,012 A | 5/1994 | Siegal | 128/744 |
| 5,318,583 A | 6/1994 | Rabenau | 606/182 |
| 5,318,584 A | 6/1994 | Lange | 606/182 |
| 5,320,607 A | 6/1994 | Ishibashi | 604/115 |
| 5,320,808 A | 6/1994 | Holen | 422/64 |
| 5,324,302 A | 6/1994 | Crouse | 606/181 |
| 5,324,303 A | 6/1994 | Strong | 606/181 |
| 5,330,634 A | 7/1994 | Wong | 205/777.5 |
| 5,332,479 A | 7/1994 | Uenoyama | 204/153.1 |
| 5,341,206 A | 8/1994 | Pittaro | 356/301 |
| 5,342,382 A | 8/1994 | Brinkerhoff | 606/184 |
| 5,344,703 A | 9/1994 | Kovar | 428/312.6 |
| 5,350,392 A | 9/1994 | Purcell | 606/182 |
| 5,352,351 A | 10/1994 | White | 204/406 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,365,699 A | 11/1994 | Armstrong | 451/7 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki | 600/578 |
| 5,370,509 A | 12/1994 | Golding | 417/423.1 |
| 5,371,687 A | 12/1994 | Holmes | 364/514 |
| 5,372,135 A | 12/1994 | Mendelson | 600/322 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentezkow | 435/180 |
| 5,390,450 A | 2/1995 | Goenka | 451/39 |
| 5,393,903 A | 2/1995 | Graetzel | 556/137 |
| 5,395,339 A | 3/1995 | Talonn | 604/111 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,283 A | 4/1995 | Goenka | 451/39 |
| 5,405,510 A | 4/1995 | Betts | 205/782 |
| 5,405,511 A | 4/1995 | White | 204/153.1 |
| 5,407,545 A | 4/1995 | Hirose | 204/153.12 |
| 5,407,554 A | 4/1995 | Saurer | 204/403 |
| 5,407,818 A | 4/1995 | Gentezkow | 435/180 |
| 5,409,583 A | 4/1995 | Yoshioka | 204/153.12 |
| 5,409,664 A | 4/1995 | Allen | 422/56 |
| 5,410,059 A | 4/1995 | Fraser | 546/10 |
| 5,415,169 A | 5/1995 | Siczek | 600/427 |
| 5,418,142 A | 5/1995 | Kiser | 435/14 |
| 5,423,847 A | 6/1995 | Strong et al. | 606/182 |
| 5,424,545 A | 6/1995 | Block | 350/343 |
| 5,426,032 A | 6/1995 | Phillips | 435/14 |
| 5,436,161 A | 7/1995 | Bergstrom | 435/291 |
| 5,437,999 A | 8/1995 | Diebold | 435/288 |
| 5,438,271 A | 8/1995 | White | 324/444 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,453,360 A | 9/1995 | Yu | 435/28 |
| 5,454,828 A | 10/1995 | Schraga | 606/181 |
| 5,456,875 A | 10/1995 | Lambert | 264/328.1 |
| 5,459,325 A | 10/1995 | Hueton | 250/458.1 |
| 5,460,182 A | 10/1995 | Goodman | 600/342 |
| 5,462,533 A | 10/1995 | Daugherty | 435/14 |
| 5,464,418 A | 11/1995 | Schraga | 606/182 |
| 5,465,722 A | 11/1995 | Fort | 600/447 |
| 5,471,102 A | 11/1995 | Becker | 310/50 |
| 5,472,427 A | 12/1995 | Rammler | 604/164.01 |
| 5,474,084 A | 12/1995 | Cunniff | 600/557 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| D367,109 S | 2/1996 | Ryner | D24/224 |
| 5,490,505 A | 2/1996 | Diab | 600/323 |
| 5,496,274 A | 3/1996 | Graves | 604/86 |
| 5,496,453 A | 3/1996 | Uenoyama | 205/777.5 |
| 5,498,542 A | 3/1996 | Corey | 435/283.1 |
| 5,501,836 A | 3/1996 | Myerson | 42/57 |
| 5,501,893 A | 3/1996 | Laermer | 428/161 |
| 5,507,288 A | 4/1996 | Bocker | 128/633 |
| 5,507,629 A | 4/1996 | Jarvik | 417/423.3 |
| 5,508,171 A | 4/1996 | Walling | 205/777.5 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith | 606/182 |
| 5,515,170 A | 5/1996 | Matzinger | 356/423 |
| 5,518,006 A | 5/1996 | Mawhirt | 128/770 |
| D371,198 S | 6/1996 | Savage | D24/169 |
| 5,524,636 A | 6/1996 | Sarvazyan | 128/774 |
| 5,525,511 A | 6/1996 | D'Costa | 435/287.9 |
| 5,525,518 A | 6/1996 | Lundsgaard | 436/68 |
| 5,526,120 A | 6/1996 | Jina | 356/446 |
| 5,527,333 A | 6/1996 | Nikkels | 606/182 |
| 5,527,334 A | 6/1996 | Kanner | 606/182 |
| 5,529,074 A | 6/1996 | Greenfield | 600/557 |
| 5,540,676 A | 7/1996 | Freiberg | 606/3 |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,545,291 A | 8/1996 | Smith | 438/107 |
| 5,547,702 A | 8/1996 | Gleisner | 427/2.13 |
| D373,419 S | 9/1996 | Muramatsu | D24/165 |
| 5,554,153 A | 9/1996 | Costello | 606/9 |
| 5,554,166 A | 9/1996 | Lange | 606/182 |
| 5,558,834 A | 9/1996 | Chu | 422/55 |
| 5,562,384 A | 10/1996 | Alvite | 414/226.01 |
| 5,562,696 A | 10/1996 | Nobles | 606/185 |
| 5,563,031 A | 10/1996 | Yu | 435/4 |
| 5,563,042 A | 10/1996 | Phillips | 435/14 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,284 A | 11/1996 | Athan | 600/323 |
| 5,575,403 A | 11/1996 | Charlton | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,591,139 A | 1/1997 | Lin | 604/264 |
| 5,593,852 A | 1/1997 | Heller | 435/14 |
| 5,599,501 A | 2/1997 | Carey | 422/64 |
| 5,605,837 A | 2/1997 | Karimi | 436/14 |
| D378,612 S | 3/1997 | Clark | D24/169 |
| 5,608,006 A | 3/1997 | Myerson | 525/54.1 |
| 5,609,749 A | 3/1997 | Yamauchi | 205/777.5 |
| 5,611,809 A | 3/1997 | Marshall | 606/181 |
| 5,611,810 A | 3/1997 | Arnold | 606/185 |
| 5,613,978 A | 3/1997 | Harding | 606/181 |
| 5,616,135 A | 4/1997 | Thorne | 604/192 |
| 5,617,851 A | 4/1997 | Lipkovker | 600/573 |
| 5,618,297 A | 4/1997 | Hart | 606/185 |
| 5,620,579 A | 4/1997 | Genshaw | 204/402 |
| 5,620,863 A | 4/1997 | Tomasco | 435/14 |

| Patent No. | Kind | Date | Name | Class |
|---|---|---|---|---|
| 5,624,458 | A | 4/1997 | Lipscher | 606/181 |
| 5,624,459 | A | 4/1997 | Kortenbach | 606/185 |
| 5,624,537 | A | 4/1997 | Turner | 204/403 |
| D379,516 | S | 5/1997 | Rutter | D24/146 |
| 5,628,764 | A | 5/1997 | Schraga | 606/182 |
| 5,628,765 | A | 5/1997 | Morita | 606/182 |
| 5,628,890 | A | 5/1997 | Carter | 204/403 |
| 5,628,961 | A | 5/1997 | Davis | 422/63 |
| 5,630,828 | A | 5/1997 | Mawhirt | 606/187 |
| 5,630,986 | A | 5/1997 | Charlton | 422/64 |
| 5,632,410 | A | 5/1997 | Moulton | 221/79 |
| 5,640,954 | A | 6/1997 | Pfeiffer | 128/635 |
| D381,591 | S | 7/1997 | Rice | D10/81 |
| 5,643,306 | A | 7/1997 | Schraga | 606/182 |
| 5,643,308 | A | 7/1997 | Markman | 606/187 |
| 5,645,555 | A | 7/1997 | Davis | 606/182 |
| 5,647,851 | A | 7/1997 | Pokras | 604/131 |
| 5,650,062 | A | 7/1997 | Ikeda | 205/778 |
| 5,653,863 | A | 8/1997 | Genshaw | 205/777.5 |
| 5,657,760 | A | 8/1997 | Ying et al. | 128/660.03 |
| 5,658,444 | A | 8/1997 | Black | 204/415 |
| 5,660,791 | A | 8/1997 | Brenneman | 422/58 |
| D383,550 | S | 9/1997 | Larson | D24/225 |
| 5,662,127 | A | 9/1997 | De Vaughn | 128/765 |
| 5,662,672 | A | 9/1997 | Pambianchi | 606/181 |
| 5,666,966 | A | 9/1997 | Horie | 128/760 |
| 5,676,143 | A | 10/1997 | Simonsen | 128/633 |
| 5,678,306 | A | 10/1997 | Bozeman | 29/888.025 |
| 5,680,858 | A | 10/1997 | Hansen | 128/635 |
| 5,680,872 | A | 10/1997 | Sesekura | 128/760 |
| 5,682,233 | A | 10/1997 | Brinda | 356/246 |
| 5,682,884 | A | 11/1997 | Hill | 128/637 |
| 5,683,562 | A | 11/1997 | Schaffar | 204/403 |
| 5,691,898 | A | 11/1997 | Rosenberg | 700/85 |
| 5,692,514 | A | 12/1997 | Bowman | 600/504 |
| 5,695,947 | A | 12/1997 | Guo | 435/11 |
| 5,700,695 | A | 12/1997 | Yassinzadeh | 436/180 |
| 5,705,045 | A | 1/1998 | Park | 204/403 |
| 5,707,384 | A | 1/1998 | Kim | 606/181 |
| 5,708,247 | A | 1/1998 | McAleer | 204/403 |
| 5,709,668 | A | 1/1998 | Wacks | 604/232 |
| 5,709,699 | A | 1/1998 | Warner | 606/181 |
| 5,710,011 | A | 1/1998 | Forrow | 435/25 |
| 5,714,123 | A | 2/1998 | Sohrab | 422/99 |
| 5,714,390 | A | 2/1998 | Hallowitz | 436/526 |
| 5,719,034 | A | 2/1998 | Kiser | 435/14 |
| 5,720,862 | A | 2/1998 | Hamamoto | 204/403 |
| 5,720,924 | A | 2/1998 | Eikmeier | 422/102 |
| D392,391 | S | 3/1998 | Douglas | D24/225 |
| D392,740 | S | 3/1998 | Yung | D24/169 |
| 5,723,284 | A | 3/1998 | Ye | 435/4 |
| 5,727,548 | A | 3/1998 | Hill | 128/637 |
| 5,729,905 | A | 3/1998 | Mathiasmeier | 33/3 R |
| 5,730,753 | A | 3/1998 | Morita | 606/181 |
| 5,733,085 | A | 3/1998 | Shida | 411/442 |
| 5,733,300 | A | 3/1998 | Pambianchi | 606/181 |
| D393,716 | S | 4/1998 | Brenneman | D24/147 |
| D393,717 | S | 4/1998 | Brenneman | D24/147 |
| 5,735,868 | A | 4/1998 | Lee | 606/189 |
| 5,736,103 | A | 4/1998 | Pugh | 422/68.1 |
| 5,738,244 | A | 4/1998 | Charlton | 221/26 |
| 5,741,228 | A | 4/1998 | Lambrecht | 604/93 |
| 5,741,634 | A | 4/1998 | Nozoe | 435/4 |
| RE35,803 | E | 5/1998 | Lange | 606/182 |
| 5,746,217 | A | 5/1998 | Erickson | 128/760 |
| 5,746,761 | A | 5/1998 | Turchin | 606/181 |
| 5,746,898 | A | 5/1998 | Preidel | 204/403 |
| 5,753,429 | A | 5/1998 | Pugh | 435/4 |
| 5,753,452 | A | 5/1998 | Smith | 435/14 |
| 5,755,228 | A | 5/1998 | Wilson | 600/459 |
| 5,755,733 | A | 5/1998 | Morita | 606/182 |
| 5,758,643 | A | 6/1998 | Wong | 600/309 |
| 5,759,364 | A | 6/1998 | Charlton | 204/403 |
| 5,762,770 | A | 6/1998 | Pritchard | 204/403 |
| 5,770,086 | A | 6/1998 | Indriksons | 210/643 |
| 5,770,369 | A | 6/1998 | Meade | 435/6 |
| 5,772,586 | A | 6/1998 | Heinonen | 600/300 |
| 5,772,677 | A | 6/1998 | Mawhirt | 606/181 |
| 5,773,270 | A | 6/1998 | D'Orazio | 435/177 |
| 5,776,157 | A | 7/1998 | Thorne | 606/182 |
| 5,776,719 | A | 7/1998 | Douglas | 435/28 |
| 5,779,365 | A | 7/1998 | Takaki | 374/161 |
| 5,780,304 | A | 7/1998 | Matzinger | 436/169 |
| 5,782,770 | A | 7/1998 | Mooradian | 600/476 |
| 5,782,852 | A | 7/1998 | Foggia | 606/182 |
| 5,788,651 | A | 8/1998 | Weilandt | 600/567 |
| 5,788,652 | A | 8/1998 | Rahn | 600/577 |
| 5,789,255 | A | 8/1998 | Yu | 536/95 |
| 5,794,219 | A | 8/1998 | Brown | 705/37 |
| 5,795,725 | A | 8/1998 | Buechler | 435/7.1 |
| 5,795,774 | A | 8/1998 | Matsumoto | 435/287.9 |
| 5,797,940 | A | 8/1998 | Mawhirt | 606/167 |
| 5,797,942 | A | 8/1998 | Schraga | 606/182 |
| 5,798,030 | A | 8/1998 | Raguse | 204/403 |
| 5,798,031 | A | 8/1998 | Charlton | 204/403 |
| 5,800,781 | A | 9/1998 | Gavin | 422/73 |
| 5,801,057 | A | 9/1998 | Smart | 436/68 |
| 5,807,375 | A | 9/1998 | Gross | 604/890.1 |
| 5,810,199 | A | 9/1998 | Charlton | 221/31 |
| D399,566 | S | 10/1998 | Sohrab | D24/169 |
| 5,820,551 | A | 10/1998 | Hill | 600/347 |
| 5,822,715 | A | 10/1998 | Worthington | 702/19 |
| 5,823,973 | A | 10/1998 | Racchini | 600/573 |
| 5,824,491 | A | 10/1998 | Priest | 435/28 |
| 5,827,181 | A | 10/1998 | Dias | 600/322 |
| 5,828,943 | A | 10/1998 | Brown | 434/258 |
| 5,829,589 | A | 11/1998 | Nguyen | 206/366 |
| 5,830,219 | A | 11/1998 | Bird | 606/130 |
| 5,832,448 | A | 11/1998 | Brown | 705/2 |
| 5,840,020 | A | 11/1998 | Heinonen | 600/309 |
| 5,840,171 | A | 11/1998 | Birch | 205/335 |
| 5,843,691 | A | 12/1998 | Douglas | 435/14 |
| 5,843,692 | A | 12/1998 | Phillips | 435/14 |
| 5,846,216 | A | 12/1998 | Gonzales | 604/2 |
| 5,846,486 | A | 12/1998 | Pugh | 422/56 |
| 5,846,490 | A | 12/1998 | Yokota | 422/66 |
| 5,849,174 | A | 12/1998 | Sanghera | 205/775 |
| 5,853,373 | A | 12/1998 | Griffith | 600/554 |
| 5,854,074 | A | 12/1998 | Charlton | 436/46 |
| D403,975 | S | 1/1999 | Douglas | D10/81 |
| 5,855,377 | A | 1/1999 | Murphy | 279/50 |
| 5,855,801 | A | 1/1999 | Lin | 216/2 |
| 5,856,174 | A | 1/1999 | Lipshutz | 435/286.5 |
| 5,856,195 | A | 1/1999 | Charlton | 436/50 |
| 5,857,967 | A | 1/1999 | Frid | 600/301 |
| 5,857,983 | A | 1/1999 | Douglas | 600/538 |
| 5,858,804 | A | 1/1999 | Zanzucchi | 506/9 |
| 5,860,922 | A | 1/1999 | Gordon et al. | 600/431 |
| 5,863,800 | A | 1/1999 | Eikmeier | 436/48 |
| 5,866,353 | A | 2/1999 | Berneth | 435/26 |
| 5,868,135 | A | 2/1999 | Kaufman | 128/630 |
| 5,868,772 | A | 2/1999 | LeVaughn | 606/181 |
| 5,869,972 | A | 2/1999 | Birch | 324/439 |
| 5,871,494 | A | 2/1999 | Simons | 606/181 |
| 5,872,713 | A | 2/1999 | Douglas | 702/85 |
| 5,873,887 | A | 2/1999 | King | 606/182 |
| 5,876,351 | A | 3/1999 | Rohde | 600/523 |
| 5,876,957 | A | 3/1999 | Douglas | 435/28 |
| 5,879,163 | A | 3/1999 | Brown | 434/236 |
| 5,879,310 | A | 3/1999 | Sopp | 600/578 |
| 5,879,311 | A | 3/1999 | Duchon | 600/583 |
| 5,879,373 | A | 3/1999 | Roper | 606/344 |
| 5,880,829 | A | 3/1999 | Kauhaniemi | 356/246 |
| 5,882,494 | A | 3/1999 | van Antwerp | 204/403 |
| 5,885,211 | A | 3/1999 | Eppstein | 600/309 |
| 5,886,056 | A | 3/1999 | Hershkowitz | 518/703 |
| 5,887,133 | A | 3/1999 | Brown | 395/200.3 |
| 5,890,128 | A | 3/1999 | Diaz | 705/2 |
| RE36,191 | E | 4/1999 | Solomon | 395/308 |
| 5,891,053 | A | 4/1999 | Sesekura | 600/583 |
| 5,892,569 | A | 4/1999 | Van de Velde | 351/221 |
| 5,893,848 | A | 4/1999 | Negus | 606/41 |
| 5,893,870 | A | 4/1999 | Talen | 606/201 |
| 5,897,493 | A | 4/1999 | Brown | 600/300 |
| 5,897,569 | A | 4/1999 | Kellogg | 606/169 |
| 5,899,855 | A | 5/1999 | Brown | 600/301 |
| 5,899,915 | A | 5/1999 | Saadat | 606/170 |
| 5,900,130 | A | 5/1999 | Benvegnu | 204/453 |

| | | | |
|---|---|---|---|
| 5,902,731 A | 5/1999 | Ouyang .................... 435/26 |
| 5,906,921 A | 5/1999 | Ikeda ...................... 435/25 |
| D411,619 S | 6/1999 | Duchon ................. D24/146 |
| 5,908,416 A | 6/1999 | Costello ..................... 606/9 |
| 5,911,937 A | 6/1999 | Hekal ..................... 264/255 |
| 5,912,134 A | 6/1999 | Shartle ................... 435/7.24 |
| 5,913,310 A | 6/1999 | Brown .................... 128/897 |
| 5,916,156 A | 6/1999 | Hildenbrand ............ 600/347 |
| 5,916,229 A | 6/1999 | Evans ..................... 606/171 |
| 5,916,230 A | 6/1999 | Brenneman .............. 606/172 |
| 5,918,603 A | 7/1999 | Brown .................... 128/897 |
| 5,919,711 A | 7/1999 | Boyd ...................... 436/178 |
| 5,921,963 A | 7/1999 | Erez ....................... 604/192 |
| 5,922,188 A | 7/1999 | Ikeda ................... 204/777.5 |
| 5,922,530 A | 7/1999 | Yu ............................ 435/4 |
| 5,922,591 A | 7/1999 | Anderson ............... 435/287.2 |
| RE36,268 E | 8/1999 | Szuminsky ............. 205/777.5 |
| 5,931,794 A | 8/1999 | Pitesky ................... 600/556 |
| 5,933,136 A | 8/1999 | Brown .................... 345/327 |
| 5,935,075 A | 8/1999 | Casscells ................. 600/474 |
| 5,938,635 A | 8/1999 | Kuhle ..................... 604/506 |
| 5,938,679 A | 8/1999 | Freeman ................. 606/181 |
| 5,940,153 A | 8/1999 | Castaneda ................. 349/58 |
| 5,942,102 A | 8/1999 | Hodges .................... 205/775 |
| 5,942,189 A | 8/1999 | Wolfbeis ................ 422/82.08 |
| 5,947,957 A | 9/1999 | Morris ...................... 606/13 |
| 5,951,300 A | 9/1999 | Brown .................... 434/236 |
| 5,951,492 A | 9/1999 | Douglas .................. 600/583 |
| 5,951,493 A | 9/1999 | Douglas .................. 600/583 |
| 5,951,582 A | 9/1999 | Thorne .................... 606/172 |
| 5,951,836 A | 9/1999 | McAleer ................... 204/403 |
| 5,954,738 A | 9/1999 | LeVaughn ............... 606/181 |
| 5,956,501 A | 9/1999 | Brown ................. 395/500.32 |
| 5,957,846 A | 9/1999 | Chiang ................... 600/447 |
| 5,958,199 A | 9/1999 | Miyamoto ............... 204/403 |
| 5,959,098 A | 9/1999 | Goldberg ................ 536/25.3 |
| 5,960,403 A | 9/1999 | Brown ....................... 705/2 |
| 5,961,451 A | 10/1999 | Reber ..................... 600/322 |
| 5,964,718 A | 10/1999 | Duchon ................... 600/583 |
| 5,965,380 A | 10/1999 | Heller ....................... 435/14 |
| 5,968,063 A | 10/1999 | Chu ........................ 606/185 |
| 5,968,760 A | 10/1999 | Phillips .................... 435/14 |
| 5,968,836 A | 10/1999 | Matzinger ............... 436/169 |
| 5,971,941 A | 10/1999 | Simons ................... 606/573 |
| 5,972,199 A | 10/1999 | Heller .................... 205/777.5 |
| 5,972,294 A | 10/1999 | Smith ....................... 422/58 |
| 5,972,715 A | 10/1999 | Celentano ............... 436/164 |
| 5,974,124 A | 10/1999 | Schlueter ............ 379/106.02 |
| 5,976,085 A | 11/1999 | Kimball .................. 600/309 |
| 5,983,193 A | 11/1999 | Heinonen ................... 705/2 |
| 5,985,116 A | 11/1999 | Ikeda ..................... 204/403 |
| 5,985,559 A | 11/1999 | Brown ....................... 435/6 |
| 5,986,754 A | 11/1999 | Harding ................... 356/246 |
| 5,993,400 A | 11/1999 | Rincoe .................... 600/595 |
| 5,993,434 A | 11/1999 | Dev ........................ 604/501 |
| D417,504 S | 12/1999 | Love ..................... D24/169 |
| 5,997,476 A | 12/1999 | Brown .................... 600/300 |
| 5,997,561 A | 12/1999 | Bocker .................... 606/182 |
| 5,997,817 A | 12/1999 | Crismore ................... 422/58 |
| 5,997,818 A | 12/1999 | Hackner .................. 422/681 |
| 6,001,067 A | 12/1999 | Shults .................... 600/584 |
| 6,007,497 A | 12/1999 | Huitema .................. 600/567 |
| D418,602 S | 1/2000 | Prokop ................. D24/169 |
| 6,014,577 A | 1/2000 | Henning ................. 600/345 |
| 6,015,392 A | 1/2000 | Douglas .................. 600/583 |
| 6,018,289 A | 1/2000 | Sekura .................. 340/309.4 |
| 6,020,110 A | 2/2000 | Williams ................. 430/315 |
| 6,022,324 A | 2/2000 | Skinner .................. 600/566 |
| 6,022,366 A | 2/2000 | Schraga .................. 606/181 |
| 6,022,748 A | 2/2000 | Charych .................. 436/527 |
| 6,023,629 A | 2/2000 | Tamada .................. 600/347 |
| 6,023,686 A | 2/2000 | Brown ...................... 705/37 |
| 6,027,459 A | 2/2000 | Shain ..................... 600/573 |
| 6,030,399 A | 2/2000 | Ignotz ..................... 606/167 |
| 6,030,827 A | 2/2000 | Davis ...................... 435/287 |
| 6,030,967 A | 2/2000 | Marui ..................... 514/215 |
| 6,032,059 A | 2/2000 | Henning ................. 600/345 |
| 6,032,119 A | 2/2000 | Brown ....................... 705/2 |
| 6,033,421 A | 3/2000 | Theiss .................... 606/186 |
| 6,033,866 A | 3/2000 | Guo ......................... 435/14 |
| 6,036,924 A | 3/2000 | Simons ................... 422/100 |
| 6,037,178 A | 3/2000 | Leiner ..................... 436/50 |
| 6,041,253 A | 3/2000 | Kost ........................ 604/20 |
| 6,045,567 A | 4/2000 | Taylor .................... 606/181 |
| 6,046,055 A | 4/2000 | Wolfbeis ................. 436/172 |
| 6,048,352 A | 4/2000 | Douglas ................... 606/181 |
| D424,696 S | 5/2000 | Ray ...................... D24/169 |
| 6,056,701 A | 5/2000 | Duchon ................... 600/583 |
| 6,059,815 A | 5/2000 | Lee ........................ 606/209 |
| 6,060,327 A | 5/2000 | Keen ...................... 436/518 |
| 6,061,128 A | 5/2000 | Zweig ................... 356/243.4 |
| 6,063,039 A | 5/2000 | Cunningham ........... 600/573 |
| 6,066,103 A | 5/2000 | Duchon ................... 600/583 |
| 6,066,243 A | 5/2000 | Anderson ............... 422/82.01 |
| 6,066,296 A | 5/2000 | Brady ....................... 422/63 |
| 6,067,463 A | 5/2000 | Jeng ....................... 600/336 |
| 6,068,615 A | 5/2000 | Brown .................... 604/207 |
| D426,638 S | 6/2000 | Ray ...................... D24/169 |
| 6,070,761 A | 6/2000 | Bloom ...................... 222/81 |
| 6,071,249 A | 6/2000 | Cunningham ........... 600/578 |
| 6,071,250 A | 6/2000 | Douglas ................... 600/583 |
| 6,071,251 A | 6/2000 | Cunningham ........... 600/584 |
| 6,071,294 A | 6/2000 | Simons ................... 606/181 |
| 6,071,391 A | 6/2000 | Gotoh .................... 204/403 |
| 6,074,360 A | 6/2000 | Haar ........................ 604/57 |
| 6,077,408 A | 6/2000 | Miyamoto ............... 204/403 |
| 6,080,106 A | 6/2000 | Lloyd ..................... 600/300 |
| 6,080,172 A | 6/2000 | Fujiwara ................. 606/166 |
| D428,150 S | 7/2000 | Ruf ....................... D24/146 |
| 6,083,196 A | 7/2000 | Trautman ................. 604/46 |
| 6,083,710 A | 7/2000 | Heller ....................... 435/14 |
| 6,084,660 A | 7/2000 | Shartle ..................... 356/39 |
| 6,085,576 A | 7/2000 | Sunshine ............... 73/29.01 |
| 6,086,544 A | 7/2000 | Hibner .................... 600/568 |
| 6,086,545 A | 7/2000 | Roe ....................... 600/570 |
| 6,086,562 A | 7/2000 | Jacobsen ................. 604/156 |
| 6,090,078 A | 7/2000 | Erskine ................... 604/198 |
| 6,091,975 A | 7/2000 | Daddona ................. 600/345 |
| 6,093,146 A | 7/2000 | Filangeri ................. 600/300 |
| 6,093,156 A | 7/2000 | Cunningham ........... 600/573 |
| D428,993 S | 8/2000 | Lubs ..................... D24/165 |
| 6,099,484 A | 8/2000 | Douglas ................... 600/583 |
| 6,099,802 A | 8/2000 | Pugh ........................ 422/58 |
| 6,100,107 A | 8/2000 | Lei ........................... 438/50 |
| 6,101,478 A | 8/2000 | Brown ....................... 705/2 |
| 6,102,933 A | 8/2000 | Lee ........................ 606/209 |
| 6,103,033 A | 8/2000 | Say ....................... 156/73.1 |
| 6,103,509 A | 8/2000 | Sode ....................... 435/190 |
| 6,104,940 A | 8/2000 | Watanabe ................ 600/345 |
| 6,106,751 A | 8/2000 | Talbot ...................... 264/81 |
| 6,107,083 A | 8/2000 | Collins ................... 435/288 |
| 6,113,578 A | 9/2000 | Brown .................... 604/207 |
| 6,117,155 A | 9/2000 | Lee ........................ 606/189 |
| 6,117,630 A | 9/2000 | Reber ......................... 435/4 |
| 6,118,126 A | 9/2000 | Zanzucchi ............... 250/458.1 |
| 6,119,033 A | 9/2000 | Spigelman .............. 600/426 |
| 6,120,462 A | 9/2000 | Hibner .................... 600/566 |
| 6,120,676 A | 9/2000 | Heller .................... 205/777.5 |
| 6,121,009 A | 9/2000 | Heller ....................... 435/14 |
| 6,122,536 A | 9/2000 | Sun ....................... 600/341 |
| 6,126,804 A | 10/2000 | Andresen ................ 204/601 |
| 6,126,899 A | 10/2000 | Woudenberg ............ 422/50 |
| 6,129,823 A | 10/2000 | Hughes ............... 204/403.01 |
| 6,132,449 A | 10/2000 | Lum ...................... 606/181 |
| 6,133,837 A | 10/2000 | Riley .................... 340/573.1 |
| 6,134,461 A | 10/2000 | Say ....................... 600/345 |
| 6,136,013 A | 10/2000 | Marshall ................. 606/167 |
| 6,139,562 A | 10/2000 | Mauze .................... 606/171 |
| 6,143,164 A | 11/2000 | Heller .................... 600/583 |
| 6,144,837 A | 11/2000 | Quy ..................... 434/307 R |
| 6,144,976 A | 11/2000 | Silva et al. .............. 708/100 |
| 6,149,203 A | 11/2000 | Hanlon .................... 283/72 |
| 6,151,586 A | 11/2000 | Brown ...................... 705/14 |
| 6,152,875 A | 11/2000 | Hakamata ................ 600/319 |
| 6,152,942 A | 11/2000 | Brenneman ............. 606/181 |
| 6,153,069 A | 11/2000 | Pottgen ................... 204/403 |
| RE36,991 E | 12/2000 | Yamamoto ............... 204/403 |
| 6,155,267 A | 12/2000 | Nelson .................... 128/899 |

| Patent | Kind | Date | Name | Class |
|---|---|---|---|---|
| 6,155,992 | A | 12/2000 | Henning et al. | 600/583 |
| 6,156,051 | A | 12/2000 | Schraga | 606/181 |
| 6,157,442 | A | 12/2000 | Raskas | 356/39 |
| 6,159,147 | A | 12/2000 | Lichter | 600/300 |
| 6,159,424 | A | 12/2000 | Kauhaniemi | 422/63 |
| 6,161,095 | A | 12/2000 | Brown | 705/2 |
| 6,162,397 | A | 12/2000 | Jurik | 422/56 |
| 6,162,611 | A | 12/2000 | Heller | 435/14 |
| 6,167,362 | A | 12/2000 | Brown | 703/11 |
| 6,167,386 | A | 12/2000 | Brown | 705/37 |
| 6,168,563 | B1 | 1/2001 | Brown | 600/301 |
| 6,168,957 | B1 | 1/2001 | Matzinger | 436/518 |
| 6,171,325 | B1 | 1/2001 | Mauze | 606/171 |
| 6,172,743 | B1 | 1/2001 | Kley | 356/39 |
| 6,175,752 | B1 | 1/2001 | Say | 600/345 |
| 6,176,847 | B1 | 1/2001 | Humphreys | 604/264 |
| 6,176,865 | B1 | 1/2001 | Mauze | 606/171 |
| 6,177,000 | B1 | 1/2001 | Peterson | 205/777.5 |
| 6,177,931 | B1 | 1/2001 | Alexander | 725/52 |
| 6,183,489 | B1 | 2/2001 | Douglas | 606/181 |
| 6,186,145 | B1 | 2/2001 | Brown | 128/897 |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,193,673 | B1 | 2/2001 | Viola | 600/568 |
| 6,193,873 | B1 | 2/2001 | Ohara | 205/792 |
| 6,194,900 | B1 | 2/2001 | Freeman | 324/321 |
| 6,197,040 | B1 | 3/2001 | LeVaughn | 606/182 |
| 6,197,257 | B1 | 3/2001 | Raskas | 422/82.05 |
| 6,200,773 | B1 | 3/2001 | Ouyang | 435/26 |
| 6,203,504 | B1 | 3/2001 | Latterell | 600/576 |
| 6,206,841 | B1 | 3/2001 | Cunningham et al. | 600/584 |
| 6,210,133 | B1 | 4/2001 | Aboul-Hosn | 417/423.1 |
| 6,210,272 | B1 | 4/2001 | Brown | 463/1 |
| 6,210,369 | B1 | 4/2001 | Wilmot | 604/157 |
| 6,210,420 | B1 | 4/2001 | Mauze | 606/182 |
| 6,210,421 | B1 | 4/2001 | Bocker | 606/182 |
| 6,212,417 | B1 | 4/2001 | Ikeda | 204/403.14 |
| 6,214,626 | B1 | 4/2001 | Meller | 436/165 |
| 6,214,804 | B1 | 4/2001 | Felgner | 514/44 |
| 6,218,571 | B1 | 4/2001 | Zheng | 562/61 |
| 6,219,574 | B1 | 4/2001 | Cormier | 604/20 |
| 6,221,023 | B1 | 4/2001 | Matsuba | 600/486 |
| 6,221,238 | B1 | 4/2001 | Grundig | 205/777.5 |
| 6,225,078 | B1 | 5/2001 | Ikeda | 435/25 |
| 6,228,100 | B1 | 5/2001 | Schraga | 606/183 |
| 6,230,051 | B1 | 5/2001 | Cormier | 604/20 |
| 6,230,501 | B1 | 5/2001 | Bailey | 62/51.1 |
| 6,231,531 | B1 | 5/2001 | Lum | 601/46 |
| 6,233,471 | B1 | 5/2001 | Berner | 600/345 |
| 6,233,539 | B1 | 5/2001 | Brown | 703/11 |
| 6,234,772 | B1 | 5/2001 | Wampler | 417/423.12 |
| 6,240,393 | B1 | 5/2001 | Brown | 705/1 |
| D444,235 | S | 6/2001 | Roberts | D24/169 |
| 6,241,862 | B1 | 6/2001 | McAleer | 204/403 |
| 6,242,207 | B1 | 6/2001 | Douglas | 435/25 |
| 6,245,060 | B1 | 6/2001 | Loomis | 606/9 |
| 6,245,215 | B1 | 6/2001 | Douglas | 205/775 |
| 6,246,992 | B1 | 6/2001 | Brown | 705/2 |
| 6,248,065 | B1 | 6/2001 | Brown | 600/300 |
| 6,251,083 | B1 | 6/2001 | Yum | 600/584 |
| 6,251,121 | B1 | 6/2001 | Saadat | 606/181 |
| 6,251,260 | B1 | 6/2001 | Heller | 205/777.5 |
| 6,251,344 | B1 | 6/2001 | Goldstein | 422/123 |
| D444,557 | S | 7/2001 | Levaughn | D24/146 |
| 6,254,831 | B1 | 7/2001 | Barnard | 422/82.08 |
| 6,256,533 | B1 | 7/2001 | Vuzhakov | 604/21 |
| 6,258,111 | B1 | 7/2001 | Ross | 606/171 |
| 6,258,229 | B1 | 7/2001 | Winarta | 204/403 |
| 6,258,254 | B1 | 7/2001 | Miyamoto | 205/777.5 |
| 6,261,241 | B1 | 7/2001 | Burbank | 600/564 |
| 6,261,245 | B1 | 7/2001 | Kawai | 600/576 |
| 6,261,519 | B1 | 7/2001 | Harding | 422/58 |
| 6,264,635 | B1 | 7/2001 | Wampler | 604/151 |
| 6,268,161 | B1 | 7/2001 | Han | 435/14 |
| 6,268,162 | B1 | 7/2001 | Phillips | 435/14 |
| 6,269,314 | B1 | 7/2001 | Iitawaki | 702/23 |
| 6,270,455 | B1 | 8/2001 | Brown | 600/300 |
| 6,270,637 | B1 | 8/2001 | Crismore | 204/403 |
| 6,272,359 | B1 | 8/2001 | Kivela | 455/567 |
| 6,272,364 | B1 | 8/2001 | Kurnik | 600/345 |
| 6,275,717 | B1 | 8/2001 | Gross | 600/345 |
| 6,280,254 | B1 | 8/2001 | Wu | 439/630 |
| 6,281,006 | B1 | 8/2001 | Heller | 435/287.9 |
| 6,283,926 | B1 | 9/2001 | Cunningham | 600/573 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |
| 6,285,454 | B1 | 9/2001 | Douglas | 356/446 |
| 6,289,254 | B1 | 9/2001 | Shimizu | 700/96 |
| 6,290,683 | B1 | 9/2001 | Erez | 604/273 |
| 6,294,897 | B1 | 9/2001 | Champlin | 320/153 |
| 6,295,506 | B1 | 9/2001 | Heinonen | 702/104 |
| 6,299,578 | B1 | 10/2001 | Kurnik | 600/309 |
| 6,299,596 | B1 | 10/2001 | Ding | 604/96.01 |
| 6,299,757 | B1 | 10/2001 | Feldman | 205/775 |
| 6,302,844 | B1 | 10/2001 | Walker | 600/300 |
| 6,302,855 | B1 | 10/2001 | Lav | 600/584 |
| 6,305,804 | B1 | 10/2001 | Rice | 351/221 |
| 6,306,104 | B1 | 10/2001 | Cunningham | 600/573 |
| 6,306,152 | B1 | 10/2001 | Verdonk | 606/182 |
| 6,306,347 | B1 | 10/2001 | Mason | 422/58 |
| 6,309,351 | B1 | 10/2001 | Kurnik | 600/309 |
| 6,309,535 | B1 | 10/2001 | Williams | 205/777.5 |
| 6,312,612 | B1 | 11/2001 | Sherman | 216/2 |
| 6,315,738 | B1 | 11/2001 | Nishikawa | 600/583 |
| 6,318,970 | B1 | 11/2001 | Backhouse | 417/92 |
| 6,319,210 | B1 | 11/2001 | Douglas | 600/583 |
| 6,322,574 | B1 | 11/2001 | Lloyd | 606/181 |
| 6,322,808 | B1 | 11/2001 | Trautman | 424/448 |
| 6,322,963 | B1 | 11/2001 | Bauer | 435/4 |
| 6,329,161 | B1 | 12/2001 | Heller | 435/14 |
| 6,330,426 | B2 | 12/2001 | Brown | 434/307 R |
| 6,331,163 | B1 | 12/2001 | Kaplan | 600/486 |
| 6,332,871 | B1 | 12/2001 | Douglas | 600/583 |
| 6,334,363 | B1 | 1/2002 | Testud | 73/862 |
| 6,334,778 | B1 | 1/2002 | Brown | 434/258 |
| 6,334,856 | B1 | 1/2002 | Allen | 604/191 |
| 6,335,203 | B1 | 1/2002 | Patel | 436/169 |
| 6,336,900 | B1 | 1/2002 | Alleckson | 600/485 |
| 6,338,790 | B1 | 1/2002 | Feldman | 205/777.5 |
| 6,346,120 | B1 | 2/2002 | Yamazaki | 623/3.13 |
| 6,349,229 | B1 | 2/2002 | Watanabe | 600/345 |
| 6,350,273 | B1 | 2/2002 | Minagawa | 606/186 |
| 6,350,451 | B1 | 2/2002 | Horn | 424/184.1 |
| 6,352,514 | B1 | 3/2002 | Douglas | 600/583 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri | 606/181 |
| 6,364,890 | B1 | 4/2002 | Lum | 606/181 |
| 6,368,273 | B1 | 4/2002 | Brown | 600/300 |
| 6,375,469 | B1 | 4/2002 | Brown | 434/236 |
| 6,375,627 | B1 | 4/2002 | Mauze | 600/584 |
| 6,379,301 | B1 | 4/2002 | Worthington | 600/309 |
| 6,379,317 | B1 | 4/2002 | Kintzig | 600/573 |
| 6,379,324 | B1 | 4/2002 | Gartstein | 604/22 |
| 6,379,969 | B1 | 4/2002 | Mauze | 436/68 |
| 6,381,577 | B1 | 4/2002 | Brown | 705/2 |
| D456,910 | S | 5/2002 | Clark | D24/225 |
| 6,387,709 | B1 | 5/2002 | Mason | 436/164 |
| 6,391,005 | B1 | 5/2002 | Lum | 604/117 |
| 6,395,227 | B1 | 5/2002 | Kiser | 422/56 |
| 6,398,522 | B2 | 6/2002 | Skill | 417/410.3 |
| 6,398,562 | B1 | 6/2002 | Butler | 439/91 |
| 6,399,394 | B1 | 6/2002 | Dahm | 436/180 |
| 6,402,701 | B1 | 6/2002 | Kaplan | 600/567 |
| 6,402,704 | B1 | 6/2002 | Mcmorrow | 600/576 |
| 6,409,740 | B1 | 6/2002 | Kuhr | 606/182 |
| 6,413,410 | B1 | 7/2002 | Hodges | 205/775 |
| 6,413,411 | B1 | 7/2002 | Pottgen | 205/777.5 |
| 6,415,821 | B2 | 7/2002 | Kamholz | 137/827 |
| 6,420,128 | B1 | 7/2002 | Ouyang | 435/14 |
| 6,421,633 | B1 | 7/2002 | Heinonen | 703/11 |
| 6,423,014 | B1 | 7/2002 | Churchill | 600/587 |
| 6,428,664 | B1 | 8/2002 | Bhullar | 204/403.03 |
| 6,436,055 | B1 | 8/2002 | Roe | 600/584 |
| 6,436,256 | B1 | 8/2002 | Williams | 204/403.06 |
| 6,436,721 | B1 | 8/2002 | Kuo | 436/514 |

| Patent No. | Date | Name | Ref. |
|---|---|---|---|
| 6,440,645 B1 | 8/2002 | Yon-Hin | 430/322 |
| 6,444,115 B1 | 9/2002 | Hodges | 205/792 |
| 6,447,119 B1 | 9/2002 | Stewart et al. | 351/212 |
| 6,447,265 B1 | 9/2002 | Antaki | 417/354 |
| 6,451,040 B1 | 9/2002 | Purcell | 606/181 |
| 6,453,810 B1 | 9/2002 | Rossmeisl | 101/123 |
| 6,458,258 B2 | 10/2002 | Taniike | 204/403 |
| 6,461,496 B1 | 10/2002 | Feldman | 205/777.5 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,472,220 B1 | 10/2002 | Simons | 436/63 |
| 6,475,360 B1 | 11/2002 | Hodges | 204/403.14 |
| 6,475,372 B1 | 11/2002 | Ohara | 205/777.5 |
| 6,475,436 B1 | 11/2002 | Schabbach | 422/64 |
| 6,475,750 B1 | 11/2002 | Han | 435/14 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,488,827 B1 | 12/2002 | Shartle | 204/403 |
| 6,488,891 B2 | 12/2002 | Mason | 422/58 |
| 6,489,133 B1 | 12/2002 | Phillips | 435/14 |
| 6,491,709 B2 | 12/2002 | Sharma | 606/181 |
| 6,491,870 B2 | 12/2002 | Patel | 422/58 |
| 6,494,830 B1 | 12/2002 | Wessel | 600/300 |
| 6,497,845 B1 | 12/2002 | Sacherer | 422/104 |
| 6,501,404 B2 | 12/2002 | Walker | 341/143 |
| 6,501,976 B1 | 12/2002 | Sohrab | 600/347 |
| 6,503,209 B2 | 1/2003 | Hakky et al. | |
| 6,503,210 B1 | 1/2003 | Hirao | 600/576 |
| 6,503,231 B1 | 1/2003 | Praunsnitz | 604/272 |
| 6,503,290 B1 | 1/2003 | Jarosinski | 75/252 |
| 6,503,381 B1 | 1/2003 | Gotoh | 204/403.14 |
| 6,506,165 B1 | 1/2003 | Sweeney | 600/562 |
| 6,506,168 B1 | 1/2003 | Fathallah | 600/578 |
| 6,506,575 B1 | 1/2003 | Knappe | 435/14 |
| 6,508,785 B1 | 1/2003 | Eppstein | 604/113 |
| 6,512,986 B1 | 1/2003 | Harmon | 702/84 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,521,110 B1 | 2/2003 | Hodges | 204/403.14 |
| 6,521,182 B1 | 2/2003 | Shartle | 422/58 |
| 6,527,521 B2 | 3/2003 | Noda | 417/355 |
| 6,527,716 B1 | 3/2003 | Eppstein | 600/309 |
| 6,527,778 B2 | 3/2003 | Athanasiou | 606/80 |
| 6,529,377 B1 | 3/2003 | Nelson | 361/699 |
| 6,530,892 B1 | 3/2003 | Kelly | 600/583 |
| 6,530,937 B1 | 3/2003 | Schraga | 606/182 |
| 6,531,322 B1 | 3/2003 | Jurik | 436/95 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,264 B1 | 3/2003 | Cormier et al. | 604/506 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,553,244 B2 | 4/2003 | Lesho | 600/347 |
| 6,554,381 B2 | 4/2003 | Locher | 347/7 |
| 6,555,061 B1 | 4/2003 | Leong | 422/58 |
| D475,136 S | 5/2003 | Taniguchi | D24/165 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,572,822 B2 | 6/2003 | Jurik | 422/56 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Iketaki | 205/777.5 |
| 6,576,416 B2 | 6/2003 | Haviland | 435/4 |
| 6,579,690 B1 | 6/2003 | Bonnecaze | 435/14 |
| 6,582,573 B2 | 6/2003 | Douglas | 204/403.1 |
| 6,584,338 B1 | 6/2003 | Van Muiswinkel | 600/419 |
| D477,670 S | 7/2003 | Jurik | D24/225 |
| 6,586,199 B2 | 7/2003 | Ouyang | 435/26 |
| 6,587,705 B1 | 7/2003 | Kim | 600/347 |
| 6,589,260 B1 | 7/2003 | Schmelzeisen-Redeker | 606/181 |
| 6,589,261 B1 | 7/2003 | Abulhaj | 606/181 |
| 6,591,124 B2 | 7/2003 | Sherman | 600/345 |
| 6,591,125 B1 | 7/2003 | Buse | 600/347 |
| 6,592,744 B1 | 7/2003 | Hodges | 205/775 |
| 6,592,745 B1 | 7/2003 | Feldman | 205/777.5 |
| 6,595,919 B2 | 7/2003 | Berner | 600/365 |
| 6,599,407 B2 | 7/2003 | Taniike | 204/403.1 |
| 6,599,693 B1 | 7/2003 | Webb | 435/4 |
| 6,599,769 B2 | 7/2003 | Kondo | 438/28 |
| 6,601,534 B2 | 8/2003 | Hebrank | 119/6.8 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,362 B2 | 8/2003 | Lum | 417/53 |
| 6,607,494 B1 | 8/2003 | Fowler | 600/570 |
| 6,607,658 B1 | 8/2003 | Heller | 205/777.5 |
| 6,612,111 B1 | 9/2003 | Hodges | 60/593 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,620,310 B1 | 9/2003 | Ohara | 205/792 |
| 6,623,501 B2 | 9/2003 | Heller | 606/181 |
| 6,626,851 B2 | 9/2003 | Hirao | 600/576 |
| 6,632,349 B1 | 10/2003 | Hodges | 205/792 |
| 6,635,222 B2 | 10/2003 | Kent | 422/22 |
| 6,638,415 B1 | 10/2003 | Hodges | 205/775 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beatty | 205/792 |
| 6,649,416 B1 | 11/2003 | Kauer | 436/164 |
| 6,650,915 B2 | 11/2003 | Routt | 600/319 |
| 6,652,720 B1 | 11/2003 | Mansouri | 204/403.11 |
| 6,652,734 B1 | 11/2003 | Hodges | 205/777.5 |
| 6,652,814 B1 | 11/2003 | House | 422/104 |
| D484,600 S | 12/2003 | Kaar | D24/169 |
| 6,656,428 B1 | 12/2003 | Clark et al. | 422/404 |
| 6,656,697 B1 | 12/2003 | Ouyang | 435/7.9 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,662,439 B1 | 12/2003 | Bhullar | 29/825 |
| 6,669,669 B2 | 12/2003 | Flaherty | 604/132 |
| 6,671,527 B2 | 12/2003 | Peterson | 600/316 |
| D484,980 S | 1/2004 | Hartwein | D24/165 |
| 6,673,617 B2 | 1/2004 | Patel | 436/8 |
| 6,676,995 B2 | 1/2004 | Dick | 427/286 |
| 6,679,841 B2 | 1/2004 | Bojan | 600/309 |
| 6,679,852 B1 | 1/2004 | Schmelzeisen-Redeker | 600/583 |
| 6,682,933 B2 | 1/2004 | Patel | 436/8 |
| 6,689,411 B2 | 2/2004 | Dick | 427/2.13 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,709,692 B2 | 3/2004 | Sudor | 427/2.1 |
| 6,713,660 B1 | 3/2004 | Roe | 604/361 |
| 6,716,577 B1 | 4/2004 | Yu | 435/6 |

| | | | |
|---|---|---|---|
| 6,719,887 B2 | 4/2004 | Hasegawa ............... 204/403.09 |
| 6,719,923 B2 | 4/2004 | Stiene ........................ 252/511 |
| 6,721,586 B2 | 4/2004 | Kiser ......................... 600/345 |
| 6,723,046 B2 | 4/2004 | Lichtenstein ............... 600/300 |
| 6,723,111 B2 | 4/2004 | Abulhaj ..................... 606/181 |
| 6,723,371 B2 | 4/2004 | Chih-hui .................... 472/2.13 |
| 6,723,500 B2 | 4/2004 | Yu ................................ 435/4 |
| 6,726,818 B2 | 4/2004 | Cui ........................ 204/403.01 |
| 6,729,546 B2 | 5/2004 | Roustaei ................ 235/462.45 |
| 6,730,494 B1 | 5/2004 | Toranto ......................... 435/28 |
| 6,731,966 B1 | 5/2004 | Spigelman .................. 600/407 |
| 6,733,493 B2 | 5/2004 | Gruzdev ......................... 606/9 |
| 6,736,777 B2 | 5/2004 | Kim ............................ 600/365 |
| 6,738,654 B2 | 5/2004 | Sohrab ....................... 600/345 |
| 6,740,215 B1 | 5/2004 | Nakaminami .......... 204/403.14 |
| 6,743,211 B1 | 6/2004 | Prausnitz ................... 604/239 |
| 6,743,597 B1 | 6/2004 | Guo ............................. 435/14 |
| 6,743,635 B2 | 6/2004 | Neel ........................... 436/95 |
| 6,746,872 B2 | 6/2004 | Zheng .......................... 436/16 |
| 6,749,618 B2 | 6/2004 | Levaughn ................... 606/182 |
| 6,749,740 B2 | 6/2004 | Liamos ....................... 205/792 |
| 6,749,792 B2 | 6/2004 | Olsen ........................ 264/328.1 |
| 6,749,887 B1 | 6/2004 | Dick .......................... 427/2.13 |
| 6,751,491 B2 | 6/2004 | Lew ............................ 600/345 |
| 6,752,817 B2 | 6/2004 | Flora .......................... 606/181 |
| 6,753,187 B2 | 6/2004 | Cizdziel ..................... 436/169 |
| 6,759,190 B2 | 7/2004 | Lin ................................ 435/4 |
| 6,764,496 B2 | 7/2004 | Schraga ...................... 606/182 |
| 6,764,581 B1 | 7/2004 | Forrow ....................... 204/403 |
| 6,767,441 B1 | 7/2004 | Cai ......................... 204/403.03 |
| 6,773,671 B1 | 8/2004 | Lewis ........................... 422/58 |
| 6,776,888 B2 | 8/2004 | Yamamoto ............. 204/403.06 |
| 6,780,645 B2 | 8/2004 | Hayter ............................ 436/8 |
| 6,780,647 B2 | 8/2004 | Fujiwara ...................... 436/169 |
| 6,783,502 B2 | 8/2004 | Orloff ......................... 600/583 |
| 6,783,537 B1 | 8/2004 | Kuhr ........................... 606/182 |
| 6,784,274 B2 | 8/2004 | van Antwerp ................. 528/77 |
| 6,786,874 B2 | 9/2004 | Grace ......................... 600/573 |
| 6,787,013 B2 | 9/2004 | Chang ........................ 204/412 |
| 6,787,109 B2 | 9/2004 | Haar ......................... 422/82.05 |
| 6,790,327 B2 | 9/2004 | Ideda ........................ 204/403.1 |
| 6,790,599 B1 | 9/2004 | Madou ........................ 430/320 |
| 6,792,791 B2 | 9/2004 | Sato ............................ 73/1.02 |
| 6,793,632 B2 | 9/2004 | Sohrab ....................... 600/573 |
| 6,793,633 B2 | 9/2004 | Douglas ...................... 600/583 |
| 6,793,802 B2 | 9/2004 | Lee .......................... 205/777.5 |
| 6,797,150 B2 | 9/2004 | Kermani .................... 205/777.5 |
| 6,800,488 B2 | 10/2004 | Khan ........................... 436/166 |
| 6,801,041 B2 | 10/2004 | Karinka ....................... 324/444 |
| 6,801,804 B2 | 10/2004 | Miller ........................... 604/20 |
| 6,802,199 B2 | 10/2004 | Hilgers ...................... 72/370.1 |
| 6,802,811 B1 | 10/2004 | Slepian ....................... 600/309 |
| 6,802,957 B2 | 10/2004 | Jung ........................ 205/777.5 |
| 6,805,780 B1 | 10/2004 | Ryu ........................ 204/403.01 |
| 6,808,499 B1 | 10/2004 | Churchill .................... 600/587 |
| 6,808,908 B2 | 10/2004 | Yao ............................ 435/181 |
| 6,808,937 B2 | 10/2004 | Ligler ......................... 436/518 |
| 6,809,807 B1 | 10/2004 | Erickson ..................... 356/213 |
| 6,811,406 B2 | 11/2004 | Grube ........................... 439/66 |
| 6,811,557 B2 | 11/2004 | Schraga ..................... 606/182 |
| 6,811,659 B2 | 11/2004 | Vachon ...................... 204/224 |
| 6,811,753 B2 | 11/2004 | Hirao .......................... 422/101 |
| 6,811,792 B2 | 11/2004 | Roser ......................... 424/423 |
| 6,812,031 B1 | 11/2004 | Carlsson ...................... 436/52 |
| 6,814,843 B1 | 11/2004 | Bhullar ................... 204/403.01 |
| 6,814,844 B2 | 11/2004 | Bhullar .................... 204/403.1 |
| 6,814,845 B2 | 11/2004 | Wilson ....................... 204/486 |
| 6,815,186 B2 | 11/2004 | Clark .......................... 435/183 |
| 6,816,742 B2 | 11/2004 | Kim ............................ 600/345 |
| 6,818,180 B2 | 11/2004 | Douglas ....................... 422/58 |
| 6,821,483 B2 | 11/2004 | Phillips ......................... 422/58 |
| 6,823,750 B2 | 11/2004 | Hodges ................... 73/864.72 |
| 6,825,047 B1 | 11/2004 | Woudenberg .............. 436/518 |
| 6,827,250 B2 | 12/2004 | Uhland ...................... 228/110.1 |
| 6,827,829 B2 | 12/2004 | Kawanaka ............... 204/403.02 |
| 6,829,507 B1 | 12/2004 | Lidman ........................ 607/19 |
| 6,830,551 B1 | 12/2004 | Uchigaki .................... 600/584 |
| 6,830,668 B2 | 12/2004 | Musho ....................... 204/400 |
| 6,830,669 B2 | 12/2004 | Miyazaki .................... 204/409 |
| 6,830,934 B1 | 12/2004 | Harding ...................... 436/166 |
| 6,833,540 B2 | 12/2004 | MacKenzie ................. 250/214 |
| 6,835,184 B1 | 12/2004 | Sage ............................. 604/46 |
| 6,835,553 B2 | 12/2004 | Han ............................. 435/14 |
| 6,835,570 B2 | 12/2004 | Patel ............................ 436/8 |
| 6,837,858 B2 | 1/2005 | Cunningham ............... 600/573 |
| 6,837,976 B2 | 1/2005 | Cai ........................ 204/403.14 |
| 6,837,988 B2 | 1/2005 | Leong ......................... 205/792 |
| 6,840,912 B2 | 1/2005 | Kloepfer ..................... 600/583 |
| 6,841,052 B2 | 1/2005 | Musho ........................ 204/401 |
| 6,843,254 B2 | 1/2005 | Tapper ........................ 128/898 |
| 6,843,902 B1 | 1/2005 | Penner ......................... 205/76 |
| 6,844,149 B2 | 1/2005 | Goldman ....................... 435/4 |
| 6,847,451 B2 | 1/2005 | Pugh ........................... 356/436 |
| 6,849,052 B2 | 2/2005 | Uchigaki .................... 600/584 |
| 6,849,168 B2 | 2/2005 | Crumly ....................... 204/416 |
| 6,849,216 B2 | 2/2005 | Rappin ........................ 264/134 |
| 6,849,456 B2 | 2/2005 | Patel ............................. 436/8 |
| 6,850,790 B2 | 2/2005 | Berner ........................ 600/347 |
| 6,852,119 B1 | 2/2005 | Abulhaj ...................... 606/182 |
| 6,852,212 B2 | 2/2005 | Maxwell ..................... 205/775 |
| 6,852,500 B1 | 2/2005 | Hoss ............................ 435/14 |
| 6,853,854 B1 | 2/2005 | Proniewiez ................. 600/319 |
| 6,855,243 B2 | 2/2005 | Khan ........................ 205/777.5 |
| 6,856,125 B2 | 2/2005 | Kermani .................... 324/71.1 |
| 6,856,928 B2 | 2/2005 | Harmon ........................ 702/84 |
| 6,858,015 B2 | 2/2005 | List ............................. 600/583 |
| 6,858,401 B2 | 2/2005 | Phillips ........................ 435/14 |
| 6,859,738 B2 | 2/2005 | Bush ............................ 702/25 |
| 6,862,466 B2 | 3/2005 | Ackerman .................. 600/347 |
| 6,862,534 B2 | 3/2005 | Sterling ....................... 702/23 |
| 6,863,800 B2 | 3/2005 | Karinka .................... 205/777.5 |
| 6,863,801 B2 | 3/2005 | Hodges ...................... 205/792 |
| 6,865,408 B1 | 3/2005 | Abbink ....................... 600/310 |
| 6,866,641 B2 | 3/2005 | Marshall ..................... 600/583 |
| 6,866,675 B2 | 3/2005 | Perez ........................... 606/181 |
| 6,866,758 B2 | 3/2005 | Bhullar .................... 204/403.2 |
| 6,866,822 B1 | 3/2005 | House ....................... 422/82.05 |
| 6,869,418 B2 | 3/2005 | Marano-Ford .............. 604/192 |
| 6,872,200 B2 | 3/2005 | Mann ......................... 604/890.1 |
| 6,872,297 B2 | 3/2005 | Mansouri ................... 205/775 |
| 6,872,298 B2 | 3/2005 | Kermani .................... 205/777.5 |
| 6,872,299 B2 | 3/2005 | Kermani .................... 205/777.5 |
| 6,872,358 B2 | 3/2005 | Hagen ........................... 422/61 |
| 6,875,208 B2 | 4/2005 | Santini ...................... 604/890.1 |
| 6,875,327 B1 | 4/2005 | Miyazaki ................ 204/403.14 |
| 6,875,613 B2 | 4/2005 | Shartle ......................... 436/63 |
| 6,878,120 B2 | 4/2005 | Roe ............................ 600/583 |
| 6,878,251 B2 | 4/2005 | Hodges ................... 204/403.14 |
| 6,878,255 B1 | 4/2005 | Wang .......................... 204/452 |
| 6,878,262 B2 | 4/2005 | Taniike ..................... 205/777.5 |
| 6,880,968 B1 | 4/2005 | Haar ........................... 374/131 |
| 6,881,203 B2 | 4/2005 | Delmore ..................... 604/272 |
| 6,881,322 B2 | 4/2005 | Tokunaga ................... 205/775 |
| 6,881,378 B1 | 4/2005 | Zimmer ........................ 422/58 |
| 6,881,541 B2 | 4/2005 | Petersen ........................ 435/6 |
| 6,881,550 B2 | 4/2005 | Phillips ........................ 435/14 |
| 6,881,551 B2 | 4/2005 | Heller .......................... 435/14 |
| 6,881,578 B2 | 4/2005 | Otake .......................... 436/44 |
| 6,882,940 B2 | 4/2005 | Potts ............................ 702/23 |
| 6,884,592 B2 | 4/2005 | Matzinger .................... 435/7.1 |
| 6,885,196 B2 | 4/2005 | Taniike ....................... 324/444 |
| 6,885,883 B2 | 4/2005 | Parris ......................... 600/347 |
| 8,752,233 | 4/2005 | Argauer ..................... 606/181 |
| 6,887,202 B2 | 5/2005 | Currie ......................... 600/309 |
| 6,887,239 B2 | 5/2005 | Elstrom ........................ 606/41 |
| 6,887,253 B2 | 5/2005 | Schraga ..................... 606/181 |
| 6,887,254 B1 | 5/2005 | Curie .......................... 606/181 |
| 6,887,426 B2 | 5/2005 | Phillips ......................... 422/56 |
| 6,887,709 B2 | 5/2005 | Leong ........................... 436/8 |
| 6,889,069 B2 | 5/2005 | Routt .......................... 600/319 |
| 6,890,319 B2 | 5/2005 | Crocker ...................... 604/131 |
| 6,890,421 B2 | 5/2005 | Ohara ....................... 205/777.5 |
| 6,890,484 B2 | 5/2005 | Bautista ........................ 422/58 |
| 6,891,936 B2 | 5/2005 | Kai .......................... 379/106.02 |
| 6,892,085 B2 | 5/2005 | McIvor ....................... 600/347 |
| 6,893,396 B2 | 5/2005 | Schulze ...................... 600/300 |
| 6,893,545 B2 | 5/2005 | Gotoh ...................... 204/403.5 |
| 6,893,552 B1 | 5/2005 | Wang ....................... 205/777.5 |

| Patent | Date | Name | Class |
|---|---|---|---|
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,911,937 B1 | 6/2005 | Sparrow | 342/188 |
| 6,913,210 B2 | 7/2005 | Baasch | 239/407 |
| 6,913,668 B2 | 7/2005 | Matzinger | 156/256 |
| 6,916,410 B2 | 7/2005 | Katsuki | 204/403 |
| 6,918,874 B1 | 7/2005 | Hatch | 600/365 |
| 6,918,901 B1 | 7/2005 | Theeuwes | 604/500 |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,960,323 B2 | 11/2005 | Guo | 422/60 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/573 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,977,722 B2 | 12/2005 | Wohlstadter et al. | 356/246 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin | 250/573 |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,210 B2 | 5/2006 | Hodges | 205/792 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,043,821 B2 | 5/2006 | Hodges | 29/594 |
| 7,044,911 B2 | 5/2006 | Drinan | 600/300 |
| 7,045,046 B2 | 5/2006 | Chambers | 204/400 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,087 B2 | 5/2006 | Jenny | 435/13 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |

| Patent Number | Kind | Date | Inventor | Class |
|---|---|---|---|---|
| 7,052,591 | B2 | 5/2006 | Gao | 204/490 |
| 7,052,652 | B2 | 5/2006 | Zanzucchi | 422/82.05 |
| 7,052,864 | B2 | 5/2006 | Durkop | 435/25 |
| 7,054,682 | B2 | 5/2006 | Young | 604/20 |
| 7,054,759 | B2 | 5/2006 | Fukunaga | 702/23 |
| D522,656 | S | 6/2006 | Orr | D24/169 |
| D523,555 | S | 6/2006 | Loerwald | D24/146 |
| 7,056,425 | B2 | 6/2006 | Hasegawa | 204/403.04 |
| 7,056,495 | B2 | 6/2006 | Roser | 424/45 |
| 7,058,437 | B2 | 6/2006 | Buse | 600/347 |
| 7,059,352 | B2 | 6/2006 | Bohm | 137/828 |
| 7,060,059 | B2 | 6/2006 | Keith | 604/504 |
| 7,060,168 | B2 | 6/2006 | Taniike | 204/403.04 |
| 7,060,192 | B2 | 6/2006 | Yuzhakov | 216/11 |
| 7,061,593 | B2 | 6/2006 | Braig | 356/39 |
| 7,063,234 | B2 | 6/2006 | Giraud | 221/271 |
| 7,063,774 | B2 | 6/2006 | Bhullar | 204/403.02 |
| 7,063,775 | B2 | 6/2006 | Yamaoka | 204/403.06 |
| 7,063,776 | B2 | 6/2006 | Huang | 204/403.14 |
| 7,066,884 | B2 | 6/2006 | Custer | 600/309 |
| 7,066,885 | B2 | 6/2006 | Erickson | 600/309 |
| 7,070,564 | B2 | 7/2006 | Matzinger | 600/300 |
| 7,070,680 | B2 | 7/2006 | Bae | 204/403.04 |
| 7,073,246 | B2 | 7/2006 | Bhullar | 29/595 |
| 7,074,307 | B2 | 7/2006 | Simpson | 204/403.04 |
| 7,074,308 | B2 | 7/2006 | Mao | 204/403.14 |
| 7,077,328 | B2 | 7/2006 | Krishnaswamy | 235/472.01 |
| 7,077,828 | B2 | 7/2006 | Kuhr | 604/207 |
| 7,078,480 | B2 | 7/2006 | Nagel | 530/322 |
| 7,079,252 | B1 | 7/2006 | Debreezeny | 356/432 |
| 7,081,188 | B1 | 7/2006 | Cho | 204/403.04 |
| 7,083,712 | B2 | 8/2006 | Morita | 205/775 |
| 7,086,277 | B2 | 8/2006 | Tess | 73/53.01 |
| 7,087,149 | B1 | 8/2006 | Muguruma | 205/778 |
| 7,090,764 | B2 | 8/2006 | Iyengar | 205/775 |
| 7,096,053 | B2 | 8/2006 | Loeb | 600/317 |
| 7,096,124 | B2 | 8/2006 | Sterling | 702/23 |
| 7,097,631 | B2 | 8/2006 | Trautman | 604/46 |
| 7,098,038 | B2 | 8/2006 | Fukuoka | 436/164 |
| 7,103,578 | B2 | 9/2006 | Beck | 705/75 |
| 7,105,006 | B2 | 9/2006 | Schraga | 606/182 |
| 7,107,253 | B1 | 9/2006 | Sumner | 706/45 |
| 7,108,680 | B2 | 9/2006 | Rohr | 604/151 |
| 7,108,778 | B2 | 9/2006 | Simpson | 205/775 |
| 7,109,271 | B2 | 9/2006 | Liu | 525/283 |
| 7,110,112 | B2 | 9/2006 | Uchida | 356/364 |
| 7,110,803 | B2 | 9/2006 | Shults | 600/347 |
| 7,112,265 | B1 | 9/2006 | McAleer | 204/403.09 |
| 7,112,451 | B2 | 9/2006 | Takahashi | 436/514 |
| 7,113,172 | B2 | 9/2006 | Hohl | 345/168 |
| 7,115,362 | B2 | 10/2006 | Douglas | 435/4 |
| 7,118,351 | B2 | 10/2006 | Effenhauser | 417/208 |
| 7,118,667 | B2 | 10/2006 | Lee | 205/777.5 |
| 7,118,668 | B1 | 10/2006 | Edelbrock | 205/777.5 |
| 7,118,916 | B2 | 10/2006 | Matzinger | 436/34 |
| 7,118,919 | B2 | 10/2006 | Yatscoff | 436/56 |
| 7,120,483 | B2 | 10/2006 | Russell | 600/345 |
| 7,122,102 | B2 | 10/2006 | Wogoman | 204/400 |
| 7,122,110 | B2 | 10/2006 | Deng | 205/777.5 |
| 7,122,111 | B2 | 10/2006 | Tokunaga | 205/792 |
| 7,125,481 | B2 | 10/2006 | Musho | 205/775 |
| 7,129,038 | B2 | 10/2006 | Gopalan | 435/4 |
| RE39,390 | E | 11/2006 | Hasegawa | 204/403.09 |
| D531,725 | S | 11/2006 | Loerwald | D24/146 |
| 7,131,342 | B2 | 11/2006 | Hodges | 73/864.72 |
| 7,131,984 | B2 | 11/2006 | Sato | 606/182 |
| 7,132,041 | B2 | 11/2006 | Deng | 205/777.5 |
| 7,133,710 | B2 | 11/2006 | Acosta | 600/316 |
| 7,134,550 | B2 | 11/2006 | Groth | 206/366 |
| 7,134,999 | B2 | 11/2006 | Brauker | 600/309 |
| 7,135,100 | B1 | 11/2006 | Lau | 204/403.14 |
| 7,137,957 | B2 | 11/2006 | Erickson | 600/573 |
| 7,138,041 | B2 | 11/2006 | Su | 204/403.04 |
| 7,138,089 | B2 | 11/2006 | Aitken | 422/82.01 |
| 7,141,034 | B2 | 11/2006 | Eppstein | 604/22 |
| 7,141,058 | B2 | 11/2006 | Briggs | 606/181 |
| 7,144,404 | B2 | 12/2006 | Whitson | 606/181 |
| 7,144,485 | B2 | 12/2006 | Hsu | 204/403.02 |
| 7,144,495 | B2 | 12/2006 | Teodorczyk | 205/792 |
| 7,144,496 | B2 | 12/2006 | Meserol | 205/792 |
| 7,144,709 | B2 | 12/2006 | Ouyang | 435/7.9 |
| 7,147,825 | B2 | 12/2006 | Matsuda | 422/58 |
| 7,150,755 | B2 | 12/2006 | Levaughn | 606/181 |
| 7,150,975 | B2 | 12/2006 | Tamada | 435/14 |
| 7,150,995 | B2 | 12/2006 | Xie | 436/67 |
| 7,153,696 | B2 | 12/2006 | Fukuoka | 436/164 |
| 7,155,371 | B2 | 12/2006 | Kawatahara | 702/187 |
| 7,156,117 | B2 | 1/2007 | Bohm | 137/14 |
| 7,156,810 | B2 | 1/2007 | Cho et al. | 600/365 |
| 7,157,723 | B2 | 1/2007 | Colvin | 250/458.1 |
| 7,160,251 | B2 | 1/2007 | Neel | 600/365 |
| 7,160,313 | B2 | 1/2007 | Galloway | 606/167 |
| 7,160,678 | B1 | 1/2007 | Kayyem | 435/6 |
| 7,162,289 | B2 | 1/2007 | Shah | 600/345 |
| 7,163,616 | B2 | 1/2007 | Vreeke | 205/777.5 |
| 7,166,074 | B2 | 1/2007 | Reghabi | 600/365 |
| 7,166,208 | B2 | 1/2007 | Zweig | 205/777.5 |
| 7,167,734 | B2 | 1/2007 | Khalil | 600/310 |
| 7,167,735 | B2 | 1/2007 | Uchida | 600/310 |
| 7,167,818 | B2 | 1/2007 | Brown | 703/11 |
| 7,169,116 | B2 | 1/2007 | Day | 600/583 |
| 7,169,117 | B2 | 1/2007 | Allen | 600/584 |
| 7,169,289 | B2 | 1/2007 | Schulein | 205/777.5 |
| 7,169,600 | B2 | 1/2007 | Hoss | 435/287.1 |
| 7,172,728 | B2 | 2/2007 | Otake | 422/58 |
| 7,174,199 | B2 | 2/2007 | Berner | 600/347 |
| 7,175,641 | B1 | 2/2007 | Schraga | 606/181 |
| 7,175,642 | B2 | 2/2007 | Briggs | 606/181 |
| 7,179,233 | B2 | 2/2007 | Chang | 600/584 |
| 7,182,910 | B2 | 2/2007 | Allen | 422/50 |
| 7,183,068 | B2 | 2/2007 | Burson | 435/14 |
| 7,183,102 | B2 | 2/2007 | Monfre | 200/51.09 |
| 7,188,034 | B2 | 3/2007 | Staib | 702/22 |
| 7,189,576 | B2 | 3/2007 | Fukuoka | 436/170 |
| 7,190,988 | B2 | 3/2007 | Say | 600/345 |
| 7,192,405 | B2 | 3/2007 | DeNuzzio | 600/583 |
| 7,192,450 | B2 | 3/2007 | Brauker | 623/23.76 |
| 7,195,704 | B2 | 3/2007 | Kermani | 205/777.5 |
| 7,198,606 | B2 | 4/2007 | Boecker | 600/583 |
| 7,199,594 | B2 | 4/2007 | Kermani | 324/663 |
| 7,202,854 | B2 | 4/2007 | Hohl | 345/168 |
| 7,206,620 | B2 | 4/2007 | Erickson | 600/310 |
| 7,206,623 | B2 | 4/2007 | Blank | 600/344 |
| D542,681 | S | 5/2007 | Young | D10/80 |
| 7,211,052 | B2 | 5/2007 | Roe | 600/584 |
| 7,211,096 | B2 | 5/2007 | Kuhr | 606/182 |
| 7,212,925 | B2 | 5/2007 | Genshaw | 702/23 |
| 7,213,720 | B2 | 5/2007 | Giraud | 220/839 |
| 7,215,982 | B2 | 5/2007 | Oshima | 600/310 |
| 7,215,983 | B2 | 5/2007 | Cho | 600/316 |
| 7,223,248 | B2 | 5/2007 | Erikson | 600/584 |
| 7,225,008 | B1 | 5/2007 | Ward | 600/345 |
| D543,878 | S | 6/2007 | Castillo | D10/81 |
| D545,438 | S | 6/2007 | Huang | D24/186 |
| 7,225,535 | B2 | 6/2007 | Feldman | 29/831 |
| 7,226,414 | B2 | 6/2007 | Ballerstadt | 600/365 |
| 7,226,461 | B2 | 6/2007 | Boecker | 606/181 |
| 7,226,978 | B2 | 6/2007 | Tapsak | 525/296 |
| 7,227,156 | B2 | 6/2007 | Colvin | 250/458.1 |
| 7,228,159 | B2 | 6/2007 | Petersson | 600/316 |
| 7,228,162 | B2 | 6/2007 | Ward | 600/345 |
| 7,228,163 | B2 | 6/2007 | Ackerman | 600/347 |
| 7,229,458 | B2 | 6/2007 | Freeman | 606/181 |
| 7,232,451 | B2 | 6/2007 | Boecker | 606/181 |
| 7,232,510 | B2 | 6/2007 | Miyazaki | 204/403.1 |
| 7,233,816 | B2 | 6/2007 | Blank | 600/310 |
| 7,235,056 | B2 | 6/2007 | Duchon | 600/583 |
| 7,235,170 | B2 | 6/2007 | Watanabe | 205/777.5 |
| 7,235,378 | B2 | 6/2007 | Yonehara | 435/14 |
| 7,236,812 | B1 | 6/2007 | Ballerstadt | 600/316 |
| 7,236,814 | B2 | 6/2007 | Shioi | 600/344 |
| D545,705 | S | 7/2007 | Voege | D10/81 |
| D546,216 | S | 7/2007 | Bolognesi | D10/81 |
| D546,218 | S | 7/2007 | Grasso | D10/81 |
| 2,747,138 | A1 | 7/2007 | Reohabi | 600/365 |
| 7,238,192 | B2 | 7/2007 | List | 606/182 |
| 7,238,534 | B1 | 7/2007 | Zimmer | 436/169 |
| 7,241,265 | B2 | 7/2007 | Cummings | 600/300 |

| Patent No. | Date | Name | Class |
|---|---|---|---|
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,513 B2 | 7/2007 | Kondoh | 600/310 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin | 600/316 |
| 7,291,117 B2 | 11/2007 | Boecker | 600/583 |
| 7,291,159 B2 | 11/2007 | Schmelzeisen-Redeker | 606/181 |
| 7,291,256 B2 | 11/2007 | Teodorezyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |
| 7,297,122 B2 | 11/2007 | Boecker | 600/583 |
| 7,297,151 B2 | 11/2007 | Boecker | 606/181 |
| 7,297,152 B2 | 11/2007 | Fukuzawa | 606/181 |
| 7,297,241 B2 | 11/2007 | Kontschieder | 204/403.01 |
| 7,297,248 B2 | 11/2007 | Bae | 205/777.5 |
| 7,297,627 B2 | 11/2007 | Shah | 438/622 |
| 7,299,079 B2 | 11/2007 | Rebec | 600/316 |
| 7,299,080 B2 | 11/2007 | Acosta | 600/316 |
| 7,299,081 B2 | 11/2007 | Mace | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/316 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,320,412 B2 | 1/2008 | Fitzgerald | 340/870.07 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/345 |
| 7,344,500 B2 | 3/2008 | Talbot | 600/365 |
| 7,344,507 B2 | 3/2008 | Briggs | 600/583 |
| 7,344,626 B2 | 3/2008 | Harding | 204/403.03 |
| 7,347,925 B2 | 3/2008 | Hsieh | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | 205/777.5 |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Schartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,270 B2 | 5/2008 | Azarnia | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/792 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/81 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |

| Patent No. | Date | Name | Class |
|---|---|---|---|
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 7,833,172 B2 | 11/2010 | Hein et al. | 600/583 |
| 7,901,365 B2 | 3/2011 | Freeman et al. | 600/583 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0018353 A1 | 8/2001 | Ishigaki | 455/566 |
| 2001/0027328 A1 | 10/2001 | Lum | 606/186 |
| 2001/0031931 A1 | 10/2001 | Cunningham | 600/573 |
| 2001/0037355 A1 | 11/2001 | Britt | 709/201 |
| 2001/0042004 A1 | 11/2001 | Taub | 705/11 |
| 2001/0045355 A1 | 11/2001 | Gephart | 204/400 |
| 2001/0054319 A1 | 12/2001 | Heller | 73/849 |
| 2002/0002326 A1 | 1/2002 | Causey | 600/300 |
| 2002/0002344 A1 | 1/2002 | Douglas | 600/583 |
| 2002/0004196 A1 | 1/2002 | Whitson | 600/573 |
| 2002/0016568 A1 | 2/2002 | Lebel | 604/131 |
| 2002/0016606 A1 | 2/2002 | Moerman | 606/181 |
| 2002/0016923 A1 | 2/2002 | Knaus | 713/200 |
| 2002/0019726 A1 | 2/2002 | Lebel | 604/66 |
| 2002/0019747 A1 | 2/2002 | Ware | 705/2 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040208 A1 | 4/2002 | Flaherty | 604/288.01 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum | 604/117 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0058902 A1 | 5/2002 | Kollias et al. | 604/20 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan | 600/573 |
| 2002/0103499 A1 | 8/2002 | Perez | 606/182 |
| 2002/0120216 A1 | 8/2002 | Fritz | 600/583 |
| 2002/0120261 A1 | 8/2002 | Morris | 606/41 |
| 2002/0123335 A1 | 9/2002 | Luna | 455/419 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0156355 A1 | 10/2002 | Gough | 600/345 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0169393 A1 | 11/2002 | Cunningham | 600/573 |
| 2002/0169394 A1 | 11/2002 | Eppstein | 600/573 |
| 2002/0176984 A1 | 11/2002 | Smart | 428/336 |
| 2002/0177761 A1 | 11/2002 | Orloff | 600/309 |
| 2002/0177763 A1 | 11/2002 | Burns | 600/345 |
| 2002/0188224 A1 | 12/2002 | Roe | 600/584 |
| 2003/0014010 A1 | 1/2003 | Carpenter | 604/117 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0032077 A1 | 2/2003 | Itoh | 435/14 |
| 2003/0038047 A1 | 2/2003 | Sleva | 206/370 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0057391 A1 | 3/2003 | Krulevitch | 251/11 |
| 2003/0060730 A1 | 3/2003 | Perez | 600/576 |
| 2003/0069509 A1 | 4/2003 | Matzinger et al. | 600/504 |
| 2003/0069753 A1 | 4/2003 | Brown | 705/2 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | 606/10 |
| 2003/0111357 A1 | 6/2003 | Black | 205/775 |
| 2003/0113827 A1 | 6/2003 | Burkoth | 435/14 |
| 2003/0116447 A1 | 6/2003 | Surridge | 205/777.5 |
| 2003/0120297 A1 | 6/2003 | Beyerlein | 606/185 |
| 2003/0135333 A1 | 7/2003 | Aceti | 702/31 |
| 2003/0136189 A1 | 7/2003 | Lauman | 73/304 C |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191376 A1 | 10/2003 | Samuels | 600/309 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |

| Pub. No. | Date | Inventor | Class |
|---|---|---|---|
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0210811 A1* | 11/2003 | Dubowsky et al. | 382/128 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0026244 A1 | 2/2004 | Hodges | 204/409 |
| 2004/0030353 A1 | 2/2004 | Schmelzeisen-Redeker | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0069657 A1 | 4/2004 | Hodges | 205/787 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107117 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Kheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |

| Pub. No. | Date | Name | Class |
|---|---|---|---|
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231983 A1* | 11/2004 | Shen et al. | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403.01 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/504 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode, Jr. | 600/365 |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049472 A1 | 3/2005 | Manda | 600/345 |
| 2005/0050859 A1 | 3/2005 | Coppeta | 53/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman | 204/403.01 |
| 2005/0064528 A1 | 3/2005 | Kwon | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0494473 | 3/2005 | Desai | 600/347 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |

| Pub. No. | Date | Name | Class |
|---|---|---|---|
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Prausnitz | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0149090 A1 | 7/2005 | Morita | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169810 A1 | 8/2005 | Hagen | 422/102 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0176153 A1 | 8/2005 | O'hara | 436/70 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205136 A1 | 9/2005 | Freeman | 137/554 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/174 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029029 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030050 A1 | 2/2006 | Milne | 436/67 |
| 2006/0030761 A1 | 2/2006 | Raskas | 600/316 |
| 2006/0030788 A1 | 2/2006 | Wong | 600/583 |
| 2006/0034728 A1 | 2/2006 | Kloepfer | 422/68.1 |
| 2006/0037859 A1 | 2/2006 | Hodges | 204/400 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |

| Pub. No. | Date | Inventor | Class |
|---|---|---|---|
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094985 A1 | 5/2006 | Aceti | 600/575 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0160100 A1 | 7/2006 | Gao | 435/6 |
| 2006/0161078 A1 | 7/2006 | Schraga | 600/583 |
| 2006/0161194 A1 | 7/2006 | Freeman | 606/185 |
| 2006/0163061 A1 | 7/2006 | Hodges | 204/401 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184065 A1 | 8/2006 | Deshmukh | 600/583 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0201804 A1 | 9/2006 | Chambers | 204/400 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222566 A1 | 10/2006 | Brauker et al. | 422/68.1 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0231442 A1 | 10/2006 | Windus-Smith | 206/438 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234263 A1 | 10/2006 | Light, II | |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247154 A1 | 11/2006 | Palmieri | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0254932 A1 | 11/2006 | Hodges | 205/775 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0266644 A1 | 11/2006 | Pugh | 205/775 |
| 2006/0266765 A1 | 11/2006 | Pugh | 222/1 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0279431 A1 | 12/2006 | Bakarania | 340/870.02 |
| 2006/0281187 A1 | 12/2006 | Emery | 436/189 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |

| Publication No. | Date | Name | Class |
|---|---|---|---|
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman | 606/181 |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Moore | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/181 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0129618 A1 | 6/2007 | Goldberger | 600/345 |
| 2007/0129650 A1 | 6/2007 | Freeman | 606/181 |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Freeman | 600/604 |
| 2007/0142776 A9 | 6/2007 | Kovelman | 604/136 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | 604/187 |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Boecker | 600/583 |
| 2007/0173742 A1 | 7/2007 | Freeman | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Attaran Rezaei | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 606/181 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 600/310 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/183 |
| 2007/0225741 A1 | 9/2007 | Ikeda | 606/182 |
| 2007/0225742 A1 | 9/2007 | Abe | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/182 |
| 2007/0233167 A1 | 10/2007 | Weiss | 606/182 |
| 2007/0233395 A1 | 10/2007 | Neel | 702/19 |
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |

| Pub. No. | Date | Inventor | Class |
|---|---|---|---|
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio | 606/185 |
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker | 600/583 |
| 2007/0276425 A1 | 11/2007 | Kim | 606/186 |
| 2007/0276621 A1 | 11/2007 | Davies | 702/104 |
| 2007/0278097 A1 | 12/2007 | Bhullar | 204/403.01 |
| 2007/0282186 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | 606/181 |
| 2007/0295616 A1 | 12/2007 | Harding | 205/777.5 |
| 2008/0004651 A1 | 1/2008 | Nicholls | 606/182 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen-Redeker | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |
| 2008/0033319 A1 | 2/2008 | Kloepfer | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee | |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 600/365 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/347 |
| 2008/0114228 A1 | 5/2008 | McCluskey | 600/365 |
| 2008/0118026 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 614/181 |
| 2008/0125815 A1 | 5/2008 | List | 606/182 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | 600/583 |
| 2008/0194989 A1 | 8/2008 | Briggs | 600/583 |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |

| Pub. No. | Kind | Date | Inventor | Class |
|---|---|---|---|---|
| 2008/0249435 | A1 | 10/2008 | Haar | 600/583 |
| 2008/0249554 | A1 | 10/2008 | Freeman | 606/181 |
| 2008/0255598 | A1 | 10/2008 | LeVaughn et al. | 606/183 |
| 2008/0262387 | A1 | 10/2008 | List | 600/583 |
| 2008/0262388 | A1 | 10/2008 | List | 600/583 |
| 2008/0267822 | A1 | 10/2008 | List | 422/68.1 |
| 2008/0269723 | A1 | 10/2008 | Mastrototaro | 604/890.1 |
| 2008/0269791 | A1 | 10/2008 | Hoenes | 606/181 |
| 2008/0275365 | A1 | 11/2008 | Guthrie | 600/584 |
| 2008/0275384 | A1 | 11/2008 | Mastrototaro | 604/66 |
| 2008/0277291 | A1 | 11/2008 | Heller | 205/777.5 |
| 2008/0277292 | A1 | 11/2008 | Heller | 205/777.5 |
| 2008/0277293 | A1 | 11/2008 | Heller | 205/777.5 |
| 2008/0277294 | A1 | 11/2008 | Heller | 205/777.5 |
| 2008/0286149 | A1 | 11/2008 | Roe | 422/58 |
| 2008/0294068 | A1 | 11/2008 | Briggs | 600/583 |
| 2008/0300614 | A1 | 12/2008 | Freeman | 606/181 |
| 2008/0318193 | A1 | 12/2008 | Alvarez-Icaza | 434/262 |
| 2008/0319284 | A1 | 12/2008 | Alvarez-Icaza | 600/309 |
| 2008/0319291 | A1 | 12/2008 | Freeman | 600/347 |
| 2009/0005664 | A1 | 1/2009 | Freeman | 600/347 |
| 2009/0020438 | A1 | 1/2009 | Hodges | 205/782 |
| 2009/0024009 | A1 | 1/2009 | Freeman | 600/309 |
| 2009/0024059 | A1 | 1/2009 | Hoerauf | 600/583 |
| 2009/0026075 | A1 | 1/2009 | Harding | 204/403.14 |
| 2009/0026091 | A1 | 1/2009 | Harding | 205/777.5 |
| 2009/0027040 | A1 | 1/2009 | Kermani | 324/123 |
| 2009/0029479 | A1 | 1/2009 | Docherty | 436/149 |
| 2009/0043177 | A1 | 2/2009 | Milledge | 600/309 |
| 2009/0043183 | A1 | 2/2009 | Kermani | 600/309 |
| 2009/0048536 | A1 | 2/2009 | Freeman | 600/583 |
| 2009/0054813 | A1 | 2/2009 | Freeman | 600/584 |
| 2009/0057146 | A1 | 3/2009 | Teodorezyk | 204/403.01 |
| 2009/0069716 | A1 | 3/2009 | Freeman | 600/583 |
| 2009/0084687 | A1 | 4/2009 | Chatelier | 205/792 |
| 2009/0105572 | A1 | 4/2009 | Malecha | 600/365 |
| 2009/0105573 | A1 | 4/2009 | Malecha | 600/365 |
| 2009/0112123 | A1 | 4/2009 | Freeman | 600/365 |
| 2009/0112155 | A1 | 4/2009 | Zhao | 604/67 |
| 2009/0112180 | A1 | 4/2009 | Krulevitch | 604/506 |
| 2009/0112185 | A1 | 4/2009 | Krulevitch | 604/523 |
| 2009/0124932 | A1 | 5/2009 | Freeman | 606/181 |
| 2009/0131829 | A1 | 5/2009 | Freeman | 600/583 |
| 2009/0131830 | A1 | 5/2009 | Freeman | 600/583 |
| 2009/0131964 | A1 | 5/2009 | Freeman | 606/181 |
| 2009/0131965 | A1 | 5/2009 | Freeman | 606/181 |
| 2009/0137930 | A1 | 5/2009 | Freeman | 600/583 |
| 2009/0138032 | A1 | 5/2009 | Freeman | 606/181 |
| 2009/0139300 | A1 | 6/2009 | Pugh | 73/1.36 |
| 2009/0184004 | A1 | 7/2009 | Chatelier | 205/777.5 |
| 2009/0187351 | A1 | 7/2009 | Orr | 702/19 |
| 2009/0192410 | A1 | 7/2009 | Freeman | 600/583 |
| 2009/0192411 | A1 | 7/2009 | Freeman | 600/583 |
| 2009/0196580 | A1 | 8/2009 | Freeman | 386/124 |
| 2009/0204025 | A1 | 8/2009 | Marsot | 600/573 |
| 2009/0216100 | A1 | 8/2009 | Ebner | 600/347 |
| 2009/0237262 | A1 | 9/2009 | Smith | 340/634 |
| 2009/0240127 | A1 | 9/2009 | Ray | 600/365 |
| 2009/0247838 | A1 | 10/2009 | Cummings | 600/309 |
| 2009/0247982 | A1 | 10/2009 | Krulevitch | 604/500 |
| 2009/0259146 | A1 | 10/2009 | Freeman | 600/583 |
| 2009/0280551 | A1 | 11/2009 | Cardosi | 435/190 |
| 2009/0281457 | A1 | 11/2009 | Faulkner | 600/583 |
| 2009/0281458 | A1 | 11/2009 | Faulkner | 600/583 |
| 2009/0281459 | A1 | 11/2009 | Faulkner | 600/583 |
| 2009/0301899 | A1 | 12/2009 | Hodges | 205/777.5 |
| 2009/0302715 | A1 | 12/2009 | Haggett | 324/715 |
| 2009/0302873 | A1 | 12/2009 | Haggett | 324/724 |
| 2009/0322630 | A1 | 12/2009 | Friman | 343/720 |
| 2009/0325307 | A1 | 12/2009 | Haggett | 436/150 |
| 2010/0016700 | A1 | 1/2010 | Sieh | 600/365 |
| 2010/0018782 | A1 | 1/2010 | Davies | 205/778 |
| 2010/0030110 | A1 | 2/2010 | Choi | 600/583 |
| 2010/0041084 | A1 | 2/2010 | Stephens | 435/14 |

FOREIGN PATENT DOCUMENTS

| | | |
|---|---|---|
| DE | 29824204 | 10/2000 |
| DE | 10053974 | 12/2000 |
| DE | 10032042 | 1/2002 |
| DE | 10057832 | 2/2002 |
| DE | 10057832 C1 | 2/2002 |
| DE | 10142232 | 3/2003 |
| DE | 10208575 C1 | 8/2003 |
| DE | 10245721 | 12/2003 |
| DE | 10361560 A1 | 7/2005 |
| EP | 0199484 A2 | 10/1986 |
| EP | 0289 269 | 11/1988 |
| EP | 0320109 | 6/1989 |
| EP | 0 364 208 A1 | 4/1990 |
| EP | 0170375 | 5/1990 |
| EP | 0136362 | 12/1990 |
| EP | 0453283 | 10/1991 |
| EP | 0263948 | 2/1992 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0560336 | 5/1998 |
| EP | 0878 708 | 11/1998 |
| EP | 0 898 936 A2 | 3/1999 |
| EP | 0505475 | 3/1999 |
| EP | 0901018 | 3/1999 |
| EP | 0470649 | 6/1999 |
| EP | 0 951 939 A2 | 10/1999 |
| EP | 0847447 | 11/1999 |
| EP | 0964059 | 12/1999 |
| EP | 0969097 | 1/2000 |
| EP | 1021950 | 7/2000 |
| EP | 0894869 | 2/2001 |
| EP | 1074832 | 2/2001 |
| EP | 1093854 | 4/2001 |
| EP | 1101443 | 5/2001 |
| EP | 1114995 | 7/2001 |
| EP | 0736607 | 8/2001 |
| EP | 0874984 | 11/2001 |
| EP | 0730037 | 12/2001 |
| EP | 0636879 | 1/2002 |
| EP | 01174083 | 1/2002 |
| EP | 0851224 | 3/2002 |
| EP | 0759553 | 5/2002 |
| EP | 0856586 | 5/2002 |
| EP | 0817809 | 7/2002 |
| EP | 0872728 | 7/2002 |
| EP | 0795748 | 8/2002 |
| EP | 0685737 | 9/2002 |
| EP | 0958495 | 11/2002 |
| EP | 0937249 | 12/2002 |
| EP | 0880692 | 1/2004 |
| EP | 01374770 | 1/2004 |
| EP | 1246688 | 5/2004 |
| EP | 1502614 | 2/2005 |
| EP | 1790288 A1 | 5/2007 |
| EP | 2039294 A1 | 3/2009 |
| GB | 2168815 | 6/1986 |
| GB | 233936 A | 6/1999 |
| GB | 2335860 A | 10/1999 |
| GB | 2335990 A | 10/1999 |
| WO | WO 80/01389 | 7/1980 |
| WO | WO 85/04089 | 9/1985 |
| WO | WO 86/07632 | 12/1985 |
| WO | WO 91/09139 | 6/1991 |
| WO | WO 93/06979 | 4/1993 |
| WO | WO 93/25898 | 12/1993 |
| WO | WO 94/27140 | 11/1994 |

| | | | | | | |
|---|---|---|---|---|---|---|
| WO | WO 94/29703 | 12/1994 | | WO | WO 02/08753 | 1/2002 |
| WO | WO 94/29704 | 12/1994 | | WO | WO 02/08950 | 1/2002 |
| WO | WO 94/29731 | 12/1994 | | WO | WO 02/18940 | 3/2002 |
| WO | WO 95/00662 | 1/1995 | | WO | WO 02/21317 | 3/2002 |
| WO | WO 95/06240 | 3/1995 | | WO | WO 02/25551 | 3/2002 |
| WO | WO 95/10223 | 4/1995 | | WO | WO 02/32559 | 4/2002 |
| WO | WO 95/22597 | 8/1995 | | WO | WO 02/41227 | 5/2002 |
| WO | WO 96/30431 | 10/1996 | | WO | WO 02/41779 | 5/2002 |
| WO | WO 97/02359 | 1/1997 | | WO | WO 02/44948 | 6/2002 |
| WO | WO 97/02487 | 1/1997 | | WO | WO/0249507 | 6/2002 |
| WO | WO 97/11883 A1 | 4/1997 | | WO | WO 02/059734 | 8/2002 |
| WO | WO 97/18464 | 5/1997 | | WO | WO 02/069791 | 9/2002 |
| WO | WO 97/30344 | 8/1997 | | WO | WO 02/077638 | 10/2002 |
| WO | WO 97/42882 | 11/1997 | | WO | WO 02/100251 | 12/2002 |
| WO | WO 97/45720 | 12/1997 | | WO | WO 02/100252 | 12/2002 |
| WO | WO 98/03431 | 1/1998 | | WO | WO 02/100253 | 12/2002 |
| WO | WO 98/19159 | 5/1998 | | WO | WO 02/100254 | 12/2002 |
| WO | WO 98/20332 | 5/1998 | | WO | WO 02/100460 | 12/2002 |
| WO | WO 98/20348 | 5/1998 | | WO | WO 02/100461 | 12/2002 |
| WO | WO 98/24366 | 6/1998 | | WO | WO 02/101343 | 12/2002 |
| WO | WO 98/24373 | 6/1998 | | WO | WO 02/101359 | 12/2002 |
| WO | WO 98/35225 | 8/1998 | | WO | WO 03/000321 | 1/2003 |
| WO | WO 99/03584 | 1/1999 | | WO | WO 03/023389 | 3/2003 |
| WO | WO 99/05966 | 2/1999 | | WO | WO 03/042691 | 5/2003 |
| WO | WO 99/07431 A1 | 2/1999 | | WO | WO 03/045557 | 6/2003 |
| WO | WO 99/13100 | 3/1999 | | WO | WO 03/046542 | 6/2003 |
| WO | WO 99/17854 | 4/1999 | | WO | WO 03/049609 | 6/2003 |
| WO | WO 99/18532 | 4/1999 | | WO | WO 03/050534 | 6/2003 |
| WO | WO 99/19507 | 4/1999 | | WO | WO 03/066128 | 8/2003 |
| WO | WO 99/19717 | 4/1999 | | WO | WO 03/070099 | 8/2003 |
| WO | WO 99/27483 | 6/1999 | | WO | WO 03/071940 | 9/2003 |
| WO | WO 99/27852 | 6/1999 | | WO | WO 03/082091 A2 | 10/2003 |
| WO | WO 99/62576 | 12/1999 | | WO | WO 03/088851 A1 | 10/2003 |
| WO | WO 99/64580 | 12/1999 | | WO | WO/03088834 | 10/2003 |
| WO | WO 00/06024 | 2/2000 | | WO | WO 03/094752 | 11/2003 |
| WO | WO 00/09184 | 2/2000 | | WO | WO 03/101297 | 12/2003 |
| WO | WO 00/11578 | 3/2000 | | WO | WO 2004/008130 | 1/2004 |
| WO | WO 00/15103 | 3/2000 | | WO | WO 2004/022133 | 3/2004 |
| WO | WO 00/17799 | 3/2000 | | WO | WO 2004/026130 | 4/2004 |
| WO | WO 00/17800 | 3/2000 | | WO | WO 2004/040285 A2 | 5/2004 |
| WO | WO 00/18293 | 4/2000 | | WO | WO 2004/040287 A1 | 5/2004 |
| WO | WO 00/19346 | 4/2000 | | WO | WO 2004/040948 | 5/2004 |
| WO | WO 00/30186 | 5/2000 | | WO | WO 2004/041082 | 5/2004 |
| WO | WO 00/32097 | 6/2000 | | WO | WO 2004/054455 | 7/2004 |
| WO | WO 00/32098 | 6/2000 | | WO | WO 2004/060174 | 7/2004 |
| WO | WO 00/33236 | 6/2000 | | WO | WO 2004/060446 | 7/2004 |
| WO | WO 00/39914 | 7/2000 | | WO | WO 2004/091693 | 10/2004 |
| WO | WO 00/42422 | 7/2000 | | WO | WO 2004/098405 | 11/2004 |
| WO | WO 00/44084 | 7/2000 | | WO | WO 2004/003147 | 12/2004 |
| WO | WO 00/50771 | 8/2000 | | WO | WO 2004/107964 | 12/2004 |
| WO | WO 00/60340 | 10/2000 | | WO | WO 2004/107975 | 12/2004 |
| WO | WO 00/64022 | 10/2000 | | WO | WO 2004/112602 | 12/2004 |
| WO | WO 00/67245 | 11/2000 | | WO | WO 2004/112612 A1 | 12/2004 |
| WO | WO 00/67268 | 11/2000 | | WO | WO 2005/001418 | 1/2005 |
| WO | WO 00/72452 | 11/2000 | | WO | WO 2005/006939 | 1/2005 |
| WO | WO 01/00090 | 1/2001 | | WO | WO 2005/011774 | 2/2005 |
| WO | WO 01/15807 | 3/2001 | | WO | WO 2005/016125 | 2/2005 |
| WO | WO 01/16578 A1 | 3/2001 | | WO | WO 2005/018425 | 3/2005 |
| WO | WO 01/75433 | 3/2001 | | WO | WO 2005/018430 | 3/2005 |
| WO | WO 01/23885 | 4/2001 | | WO | WO 2005/018454 | 3/2005 |
| WO | WO 01/25775 | 4/2001 | | WO | WO 2005/018709 | 3/2005 |
| WO | WO 01/26813 | 4/2001 | | WO | WO 2005/018710 | 3/2005 |
| WO | WO 01/33216 | 5/2001 | | WO | WO 2005/018711 | 3/2005 |
| WO | WO 01/34029 | 5/2001 | | WO | WO 2005/022143 | 3/2005 |
| WO | WO 01/36955 | 5/2001 | | WO | WO 2005/023088 | 3/2005 |
| WO | WO 01/37174 | 5/2001 | | WO | WO 2005/033659 | 4/2005 |
| WO | WO 01/45014 A1 | 6/2001 | | WO | WO 2005/034720 | 4/2005 |
| WO | WO 01/40788 | 7/2001 | | WO | WO 2005/034721 | 4/2005 |
| WO | WO 01/57510 | 8/2001 | | WO | WO 2005/034741 | 4/2005 |
| WO | WO 01/64105 | 9/2001 | | WO | WO 2005/034778 | 4/2005 |
| WO | WO 01/66010 | 9/2001 | | WO | WO 2005/035017 | 4/2005 |
| WO | WO 01/69505 | 9/2001 | | WO | WO 2005/035018 | 4/2005 |
| WO | WO 01/72225 | 10/2001 | | WO | WO 2005/037095 | 4/2005 |
| WO | WO 01/73124 | 10/2001 | | WO | WO 2005/046477 | 5/2005 |
| WO | WO 01/73395 | 10/2001 | | WO | WO 2005/065399 | 7/2005 |
| WO | WO 01/89691 | 11/2001 | | WO | WO 2005/065414 | 7/2005 |
| WO | WO 02/00101 | 1/2002 | | WO | WO 2005/065415 | 7/2005 |
| WO | WO 02/02796 | 1/2002 | | WO | WO 2006005545 A2 | 7/2005 |
| WO | WO 02/08750 | 1/2002 | | WO | WO 2005/072604 | 8/2005 |

| | | |
|---|---|---|
| WO | WO 2005/084557 | 9/2005 |
| WO | WO 2005/104948 A1 | 11/2005 |
| WO | WO 2005/116622 | 12/2005 |
| WO | WO 2005/119234 | 12/2005 |
| WO | WO 2005/120365 A1 | 12/2005 |
| WO | WO 2005/121759 | 12/2005 |
| WO | WO 2006/001973 | 1/2006 |
| WO | WO 2006/011062 | 2/2006 |
| WO | WO 2006/013045 | 2/2006 |
| WO | WO 2006/027702 A2 | 3/2006 |
| WO | WO 2006/032391 | 3/2006 |
| WO | WO 2006/072004 | 7/2006 |
| WO | WO 2007/088905 A1 | 8/2007 |

OTHER PUBLICATIONS

Machine translation of De 10053974 pp. 1-4, provided by epo.org.

* cited by examiner

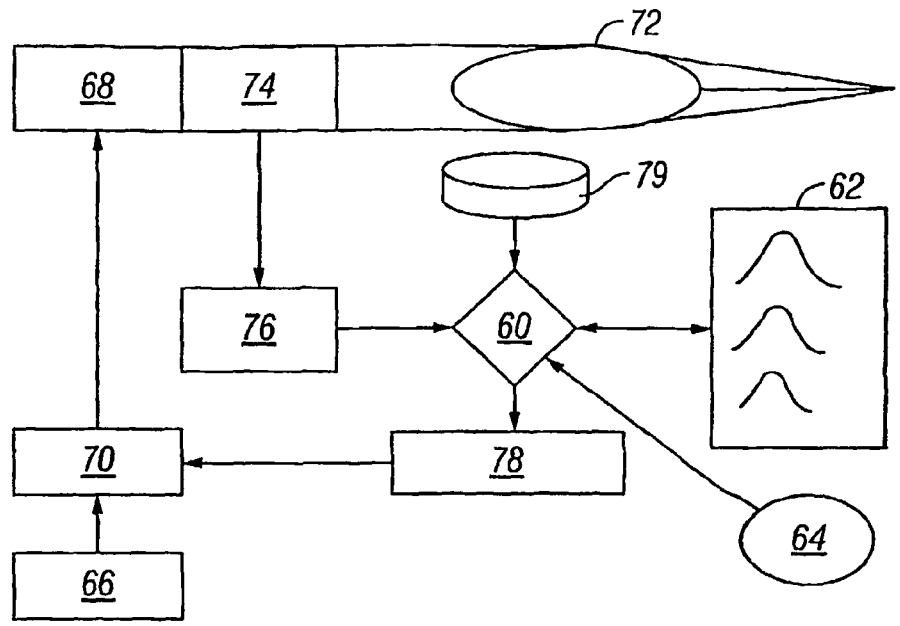
FIG. 26
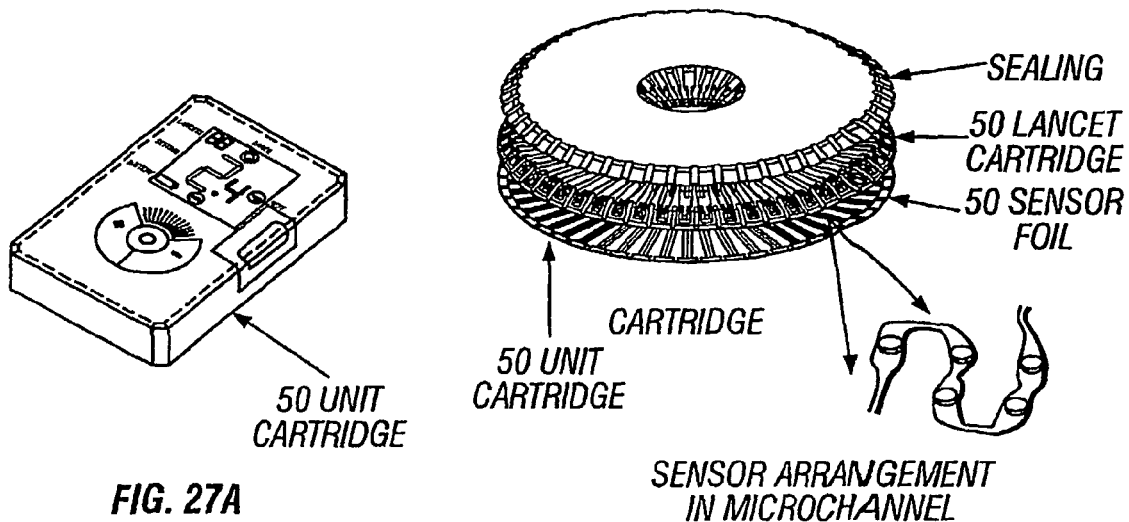
FIG. 27A
FIG. 27B

METHOD AND APPARATUS FOR AN IMPROVED SAMPLE CAPTURE DEVICE

BACKGROUND OF THE INVENTION

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

When using existing methods, blood often flows from the cut blood vessels but is then trapped below the surface of the skin, forming a hematoma. In other instances, a wound is created, but no blood flows from the wound. In either case, the lancing process cannot be combined with the sample acquisition and testing step. Spontaneous blood droplet generation with current mechanical launching system varies between launcher types but on average it is about 50% of lancet strikes, which would be spontaneous. Otherwise milking is required to yield blood. Mechanical launchers are unlikely to provide the means for integrated sample acquisition and testing if one out of every two strikes does not yield a spontaneous blood sample. It would be desirable to find improved methods to actuate the lancet.

As lancing devices have become more advanced, so have the sensors used to measure the glucose levels in the blood samples. These analyte sensors now operate using increasing lower volumes of blood sample. Some of these analyte sensors are designed for use with lancing devices that create smaller wounds, which is beneficial in that there is less pain and tissue damage, but also provide less blood to work with. As the required amount of blood decreases, it becomes increasing important to guide the ever shrinking volumes of blood towards the sensor in an efficient manner that does not waste the small volumes of blood. At low volumes, it is desirable to regulate fluid flow so that the small amounts of fluid are not wasted on surfaces that do not provide an analyte measurement.

A still further problem concerns the possible inability to guarantee blood flow from the finger lancet wound to the sensor port located on the disposable cartridge. The problem might be the invariability of the blood volume from the lancet wound, otherwise known as the shape and size of the droplet. There have been stated solutions such as the delivery of the lancet to the finger with a deeper penetration depth or a programmed controlled "lancet-in-the-finger" dwell time to sustain the size of the wound, which allows more blood to be produced from the wound. However, each might possibly result in a compromise on the degree of pain or sensation felt by the patient.

In some embodiments, a capillary may be co-located with the lancet. In order to get the blood into the capillary, several variables (lateral movement or other variation) come into play. Unless the blood droplet is directly centered on the capillary, there may be difficulty transporting enough blood to the analyte detecting member. For example, if there is any type of lateral movement or if the blood does not fall into the capillary tube, it can smear on the side wall. With an integrated sampling configuration where it may be difficult to visualize where the blood or body fluid is going, there may be no way for the subject to rectify the situation by milking the finger to get a larger droplet and increase the potential of getting the blood in.

The design of these improved medical devices has also challenged engineers to come up with more efficient methods of design. With macroscopic devices, such as conventional blood chemistry analyzers or flow cytometers, it is usually possible during the development phase to mount flow sensors, temperature probes, and optical detectors at various positions along the instrument pathway to experimentally determine the optimum operational parameters for the device. However, this approach often fails for microdevices because standard sensors and probes are typically of the same scale as the microdevice and interfere so much with device behavior that the measured data do not represent actual device performance. Thus it would be desirable to come up with design models where the most useful experimental data tend to be external measurements from which the internal physics of the microdevice should be deduced.

SUMMARY OF THE INVENTION

The present invention provides solutions for at least some of the drawbacks discussed above. The technical field relates to guiding a fluid sample obtained from the body for analysis. Because of the low fluid volumes envisioned for improved sensing devices, the ability to efficiently guide the small sample volumes to a targeted area is of interest. Specifically, some embodiments of the present invention provide a body fluid sampling device with improved fluid control. Preferably, the improved fluid control is easy to use. At least some of these and other objectives described herein will be met by embodiments of the present invention.

In one aspect, the present invention provides surface texturing that corrals or guides fluid in areas that desire to receive the fluid sample. The texturing may also be used in combination with other surface treatments such as coatings. Texturing, however, it a more permanent solution.

In one embodiment, a radial cartridge is provided that has a plurality of penetrating members and a plurality of analyte detecting members where texturing near the detecting members guides the fluid to the members. The texturing may be formed by a variety of techniques as known in the art and can be formed in various geometries. The present invention allows very small volumes of fluid to be guided by restricting its flow due to surface texturing.

In another aspect of the present invention, the invention relates to using an electronic tissue penetration device to drive a penetrating member into tissue, sample the body fluid, and measure analyte levels in the body fluid using a sensor cartridge. The invention uses various techniques to draw body fluid towards an analyte detecting device on the cartridge.

Embodiments of the present invention provide solutions to a problem, which concerns the possible inability to guaranteed a stable blood volume from a finger lancet wound to a sensor port located on a disposable cartridge. The problem might be due to shallowness of the lancet penetration depth, skin surface tension issues, or the patient's vascular conditions resulting in the invariability in achieving an adequate blood droplet shape and size. There have been other stated solutions such as the delivery of the lancet to the finger with a deeper penetration depth or a control method to increase the amount of blood to be produced from the wound.

In one embodiment, this invention produces a concept of a capillary need for the blood to travel directly from the wound to the sensor port on the cartridge. Thus the volume of blood produced at the wound site irregardless of its droplet geometry can be completely transported to the analyte detecting member.

In a still further aspect, the present invention provides solutions for at least some of the drawbacks discussed above. Specifically, some embodiments of the present invention provide an improved, integrated fluid sampling device. To improve device integration, devices and methods for connecting sensor regions to contact pad regions may be provided. One of the problems involves getting electrical contact with the leads connected to electrodes coupled to the sensor regions. At least some of these and other objectives described herein will be met by embodiments of the present invention.

In yet another aspect, the technical field of the invention relates to thick film conductor depositions for the purpose of providing sensory device placement, signal conduction, and isolation from environments detrimental to the sensory device storage and integrity prior to utilization.

In one embodiment, the present invention provides solutions for at least some of the drawbacks discussed above. The invention relates to the electronically controlled actuation of a lancet to create a wound for the collection of a blood sample for analysis. Specifically, some embodiments of the present invention provide an improved fluid sampling device. Because of the obtain spontaneous blood generation in a relatively painless manner, the ability to move the penetrating member at a high, yet controllable velocity is of interest. At least some of these and other objectives described herein will be met by embodiments of the present invention.

In another aspect of the present invention, the invention relates to using the electronic tissue penetration device to drive a penetrating member into tissue, wherein a elastomeric portion actuated by the electronic device to drive the penetrating member. More specifically, the invention relates to the electronic actuation of a lancet through the use of an elastomeric capacitor that can be made to change length with the application of voltage across the capacitor plates.

In one embodiment, a method of body fluid sampling is provided. The method comprises moving a penetrating member at conforming to a selectable velocity profile or motion waveform by using electricity to actuate and elastomeric device and measuring the position of the penetrating member. In some embodiments, the device will use the position data to create a feedback loop wherein the actuator will move the penetrating member at velocities that follow a desired trajectory.

Still further, the present invention provides solutions for at least some of the drawbacks in designing medical devices. The technical field relates to methods for designing microscale devices. Because the difficulty of building such sensors for testing, the ability of the present invention to accurately model the microscale device is of interest. Specifically, some embodiments of the present invention provide an improved method and model for developing such microscale devices. At least some of these and other objectives described herein will be met by embodiments of the present invention.

Embodiments of the present invention disclosed herein comprise the use of a mathematical modeling algorithm to develop a list of design rules for dispersed-phase-based biosensors. Furthermore, various pieces of hardware as well as embodiments of a glucose detecting member are disclosed.

The system may further comprise means for coupling the force generator with one of the penetrating members.

The system may further comprise a penetrating member sensor positioned to monitor a penetrating member coupled to the force generator, the penetrating member sensor configured to provide information relative to a depth of penetration of a penetrating member through a skin surface.

The depth of penetration may be about 100 to 2500 microns.

The depth of penetration may be about 500 to 750 microns.

The depth of penetration may be, in this nonlimiting example, no more than about 1000 microns beyond a stratum corneum thickness of a skin surface.

The depth of penetration may be no more than about 500 microns beyond a stratum corneum thickness of a skin surface.

The depth of penetration may be no more than about 300 microns beyond a stratum corneum thickness of a skin surface.

The depth of penetration may be less than a sum of a stratum corneum thickness of a skin surface and 400 microns.

The penetrating member sensor may be further configured to control velocity of a penetrating member.

The active penetrating member may move along a substantially linear path into the tissue.

The active penetrating member may move along an at least partially curved path into the tissue.

The driver may be a voice coil drive force generator.

The driver may be a rotary voice coil drive force generator.

The penetrating member sensor may be coupled to a processor with control instructions for the penetrating member driver.

The processor may include a memory for storage and retrieval of a set of penetrating member profiles utilized with the penetrating member driver.

The processor may be utilized to monitor position and speed of a penetrating member as the penetrating member moves in a first direction.

The processor may be utilized to adjust an application of force to a penetrating member to achieve a desired speed of the penetrating member.

The processor may be utilized to adjust an application of force to a penetrating member when the penetrating member contacts a target tissue so that the penetrating member penetrates the target tissue within a desired range of speed.

The processor may be utilized to monitor position and speed of a penetrating member as the penetrating member moves in the first direction toward a target tissue, wherein the application of a launching force to the penetrating member is controlled based on position and speed of the penetrating member.

The processor may be utilized to control a withdraw force to the penetrating member so that the penetrating member moves in a second direction away from the target tissue.

In the first direction, the penetrating member may move toward the target tissue at a speed that is different than a speed at which the penetrating member moves away from the target tissue.

In the first direction the penetrating member may move toward the target tissue at a speed that is greater than a speed at which the penetrating member moves away from the target tissue.

The speed of a penetrating member in the first direction may be the range of about 2.0 to 10.0 m/sec.

The average velocity of the penetrating member during a tissue penetration stroke in the first direction may be about 100 to about 1000 times greater than the average velocity of the penetrating member during a withdrawal stroke in a second direction.

A further understanding of the nature and advantages of the invention will become apparent by reference to the remaining portions of the specification and drawings.

BRIEF DESCRIPTION OF THE DRAWINGS

FIG. 26 is a schematic showing one embodiment of feedback control for a penetrating member.

FIGS. 27A and 27B are perspective views of a fluid sampling device and a cartridge for use with such a device.

DESCRIPTION OF THE SPECIFIC EMBODIMENTS

The present invention provides a multiple analyte detecting member solution for body fluid sampling. Specifically, some embodiments of the present invention provides a multiple analyte detecting member and multiple penetrating member solution to measuring analyte levels in the body. The invention may use a high density design. It may use penetrating members of smaller size, such as but not limited to diameter or length, than known lancets. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It must be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

Figure 1:
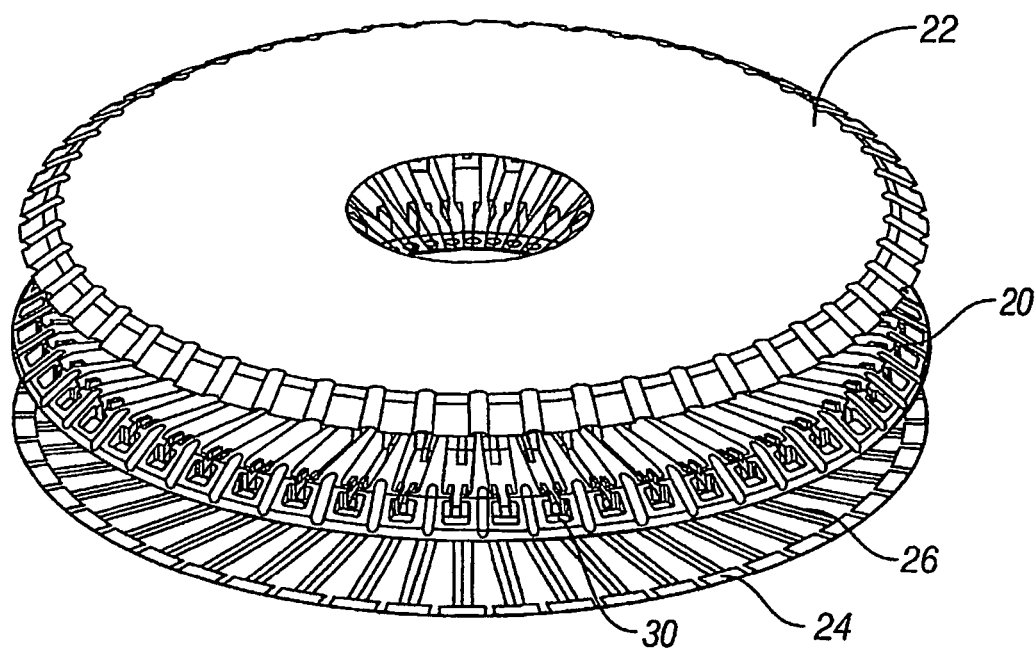
FIG. 1 is an exploded view of one embodiment of a cartridge with sealing layer and analyte detecting layer according to the present invention.

FIG. 1 shows one embodiment of a radial cartridge 20. The cartridge 20 may include a sterility barrier 22 and a substrate 24 having a plurality of analyte detecting members 26. In this embodiment, the cartridge 20 is designed so that blood will enter the fluid chamber 30 and be held there for analysis.

Figure 2:
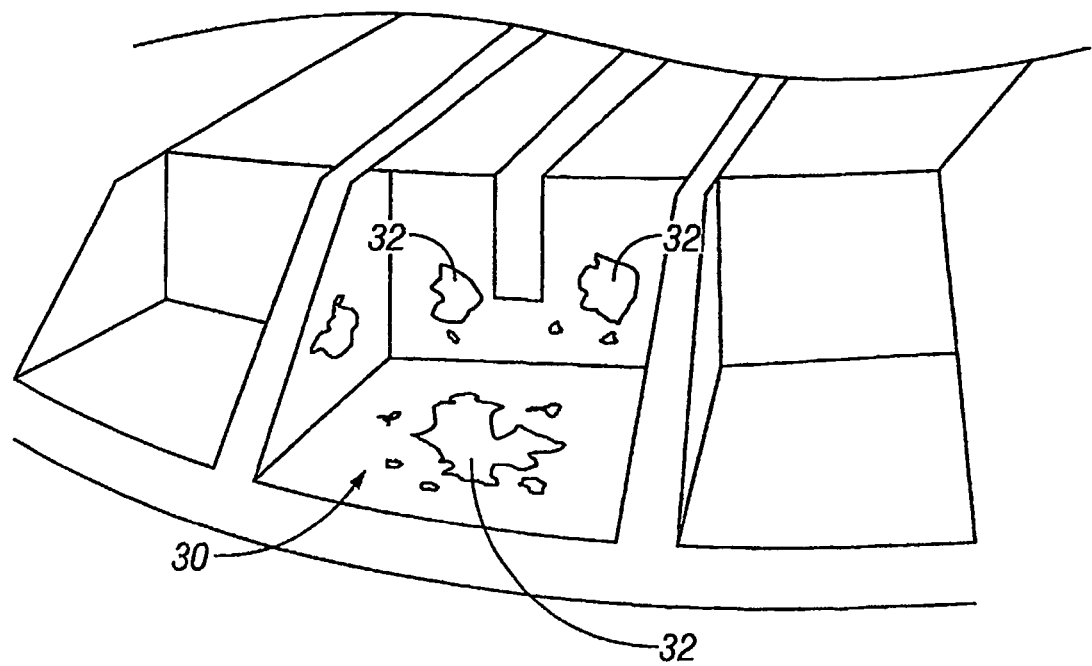
FIG. 2 shows a close-up view of one portion of the cartridge of FIG. 1.

Referring now to FIG. 2, a close up view of one embodiment of the sample chamber 30 is shown. As discussed, it is often desirable to have a hydrophilic surface in certain areas when trying to create fluid flow. However, as seen in FIG. 2, having a flat surface that is hydrophilic may cause the fluid sample 32 to spread all over the sample chamber 30.

In one embodiment of the present invention, surface texturing may be used to address the issue. Although not limited to the following, texturing may also be combined with chemical surface treatments or other surface treatments. To design the texture, one may need to account for the surface tension (contact angle), the bulk properties (density, etc.) and surface flow. Since the volumes that the present invention deals with may be, as a nonlimiting example, in the area of about 250-500 nl, just having blood flow around, is something that the device cannot afford. It is desired that the fluid flow be a shaped flow, because at low volumes, the fluid cannot be wasted on errant flows.

At low volumes, there is no conservation, and the blood goes everywhere. For one nonlimiting example where it is desired that the blood or fluid goes into a tube. However, the preferential path is the surface and until the tube fills completely and creates a pressure differential, the blood is not all going in there. The blood could try to pull but the fluid could "break" and then not all of the blood is pulled into the tube and into the device for measurement.

In one embodiment, the present invention essentially involves texturing to direct the flow. For example and not limitation, the texturing may be on the cartridge 20 or it may be along fluid paths formed by the cartridge 20. This is one solution for tubular designs (i.e. capillary tube). Playing with the flow equation allows for designing of the texturing, but meshes are different animals since they create increased surface area. The tubular problem, such as guiding fluid into a sensor area or a capillary tube involves positioning the fluid to engage the capillary. In one embodiment, a single material is used. The material may be an ideal flow material for use with a single molding. Multiple moldings/laminated moldings may be used. As a nonlimiting example, materials may have a contact angle in the area of about 20 to 5 degrees.

FIGS. 3A-3H show examples of geometries that may be used with the present invention. These are purely exemplary and are nonlimiting. Additionally, roughing or texturing the surface may improve user feedback, letting them know whether they are on target. It might help with the sensation of contact. The texturing may be dimples, raised portions, detents, depressions, cross-hatch, scoring, criss-cross, triangles, any of a variety of other surface geometries, and/or any single or multiple combinations of the above.

Figure 3A:
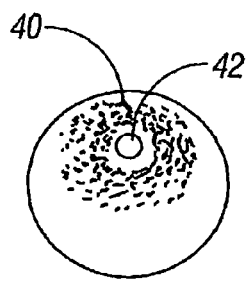
FIGS. 3A-3H show examples of geometries for texturing formations.
Figure 3E:
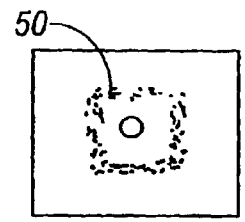
Figure 3B:
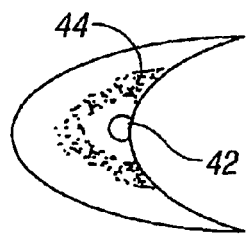
Figure 3F:
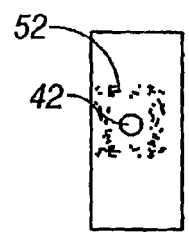
Figure 3C:
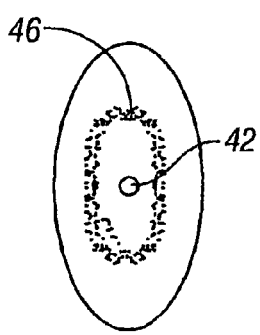
Figure 3G:
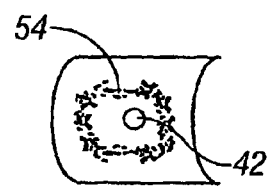
Figure 3D:
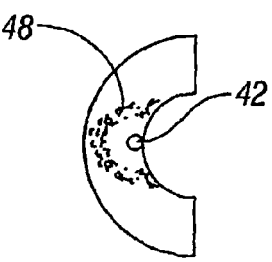
Figure 3H:
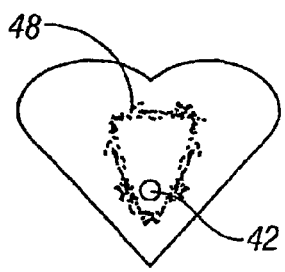

FIG. 3A shows an embodiment where the texturing 40 is in a circular structure shape around an opening 42 for receiving body fluid. In this embodiment, the texturing 40 is designed to "corral" fluid towards the opening 42. FIG. 3B show texturing 44 in a parabolic shape. As seen in FIG. 3B, the texturing does not necessarily fully surround the opening 42. FIG. 3C shows texturing 46 in an elliptical configuration. FIG. 3D shows texturing 48 in a horseshoe configuration. FIG. 3E shows texturing 50 in a box configuration. FIG. 3F shows texturing 52 in a rectangular configuration. FIG. 3G shows texturing 54 in a curved-linear configuration. FIG. 3H shows texturing 56 in a teardrop-heart shape. It should be understood that polygonal, hexagonal, triangular, or other shapes may also be used. The texturing can be placed on any surface and is not limited to being placed on the surface shapes shown. Some embodiments may have single or multiple combinations of the above shapes.

For changing surface property of Teflon and other materials, you can chemically attack it. As an example, the chemical attack may result in about 30 angstroms of surface change. By texturing, it forms and stays in that ring. But in the middle it starts to move into the sensor area (since the other areas are corralled). In some embodiments, a funnel area may be located at center of the "corral". We are affecting the surface properties by texturing.

As a nonlimiting example, the texturing may be used with a typical 300 micron diameter lancet. The blood droplet could form anywhere on the lancet. It's also a C-shaped wound created on the patient. The cutting edge creates that shape. Anywhere around this, droplet can go in the center, or anywhere around the C. That why the texturing is used to corral fluid that may hit the surface and need to be guided. In some embodiments, there could be gaps in the texturing so that fluid and directed in certain directions.

Types of texturing includes but is not limited to lumpy, bumpy (just texturing) round dots, square dots, etc. . . . . Texturing may be formed by any variety of techniques including but not limited to aiming a plasma beam to create the texturing; sacrificial foam/hot press embossing; chemical texturing, combinations of the above, and other techniques as known in the art.

Figure 4:
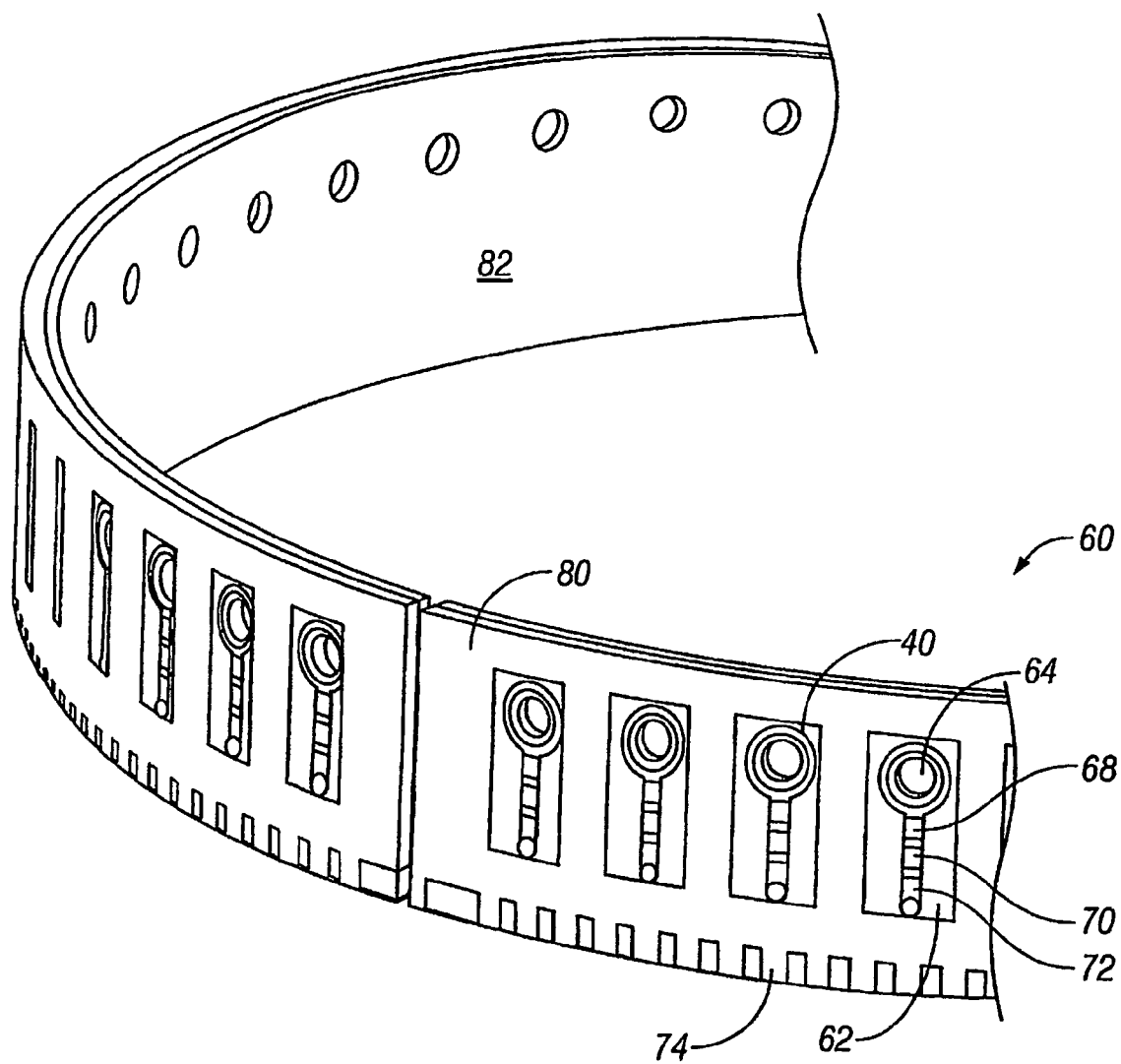
FIG. 4 shows a perspective view of a ring of analyte detecting members that may have texturing.

Referring now to FIG. 4, one embodiment of a ring 60 for use with a cartridge such as that shown in FIG. 1, will now be described. This embodiment of a ring 60 having a plurality of analyte detecting members 62 is shown. For example and not limitation, the ring 60 may be formed a linear tape of analyte detecting member 62 formed into a circular configuration. The analyte detecting member 62 may include an aperture 64 to allow for a penetrating member (not shown) to pass through to penetrate tissue. In the present embodiment, the analyte detecting member 62 may have three electrodes 68, 70, and 72. The electrodes are coupled to the appropriate electrical contacts 74. The present invention may also include texturing 40 on the analyte detecting member 62.

It should be understood that in some embodiments, the linear tape of analyte detecting members 62 may be "folded" in a reverse manner so that the outer surface 80 of the ring 62 will now be the inner surface (or inner diameter) of the ring 62. Thus the leads 74 will be on the inner surface and the plain backing 82 will now face outward. In such a configuration, the backing 82 would now have the texturing as shown in FIGS. 3A-3H. Having this reverse configuration allows the electrodes to be on the side of the analyte detecting member that first receives body fluid as indicated by arrow 1234. The embodiment of FIG. 4 may also be formed or attached to the outer circumferential surface of the cartridge.

Referring to FIG. 4, the orientation of the analyte detecting members 62 is orthogonal to the orientation of the penetrating member. The penetrating member moves through the aperture 64, through a sample capture port (not shown) to pierce into the skin or tissue and retract. In one embodiment, the blood sample may move by capillary or wicking action across the electrodes 68, 70, and/or 72. There may be wicking material used on all or part of the sample capture or transport area. The sample volume for this configuration is relatively small, less than 300 nl. In some embodiments, the amount in the analyte detecting member is about 60 to 70 nl. The required space for the capillary and electrodes is relatively small, less than 20 mm$^2$. In one embodiment, the range of the aperture 64 is about 0.5-1.0 mm.

Figure 5:
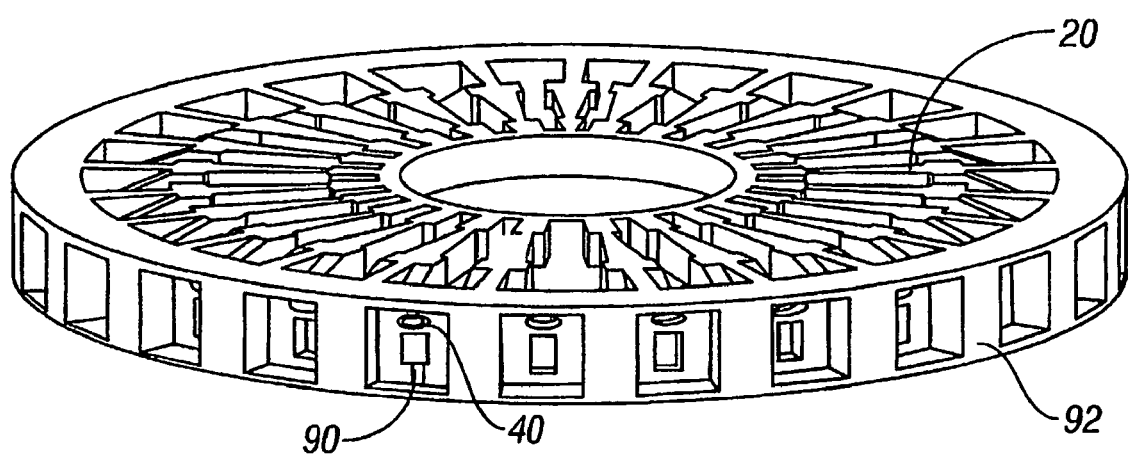
FIG. 5 shows another embodiment of the present invention with texturing.

FIG. 5 shows yet another embodiment of the present invention which may use texturing 40. This embodiment may use individual analyte detecting members 90 and mated with a cage 92 to hold them in position for use with a disc or cartridge containing a plurality of penetrating members. The cage 92 may be integrally formed with the cartridge 20 holding the plurality of penetrating members or it may be formed separately and then coupled to the cartridge. As seen in FIG. 5, some embodiments of the device may have fewer than 50 penetrating members, such as but not limited to 17, 20, 25, 30, or 40 penetrating members.

Figure 6:
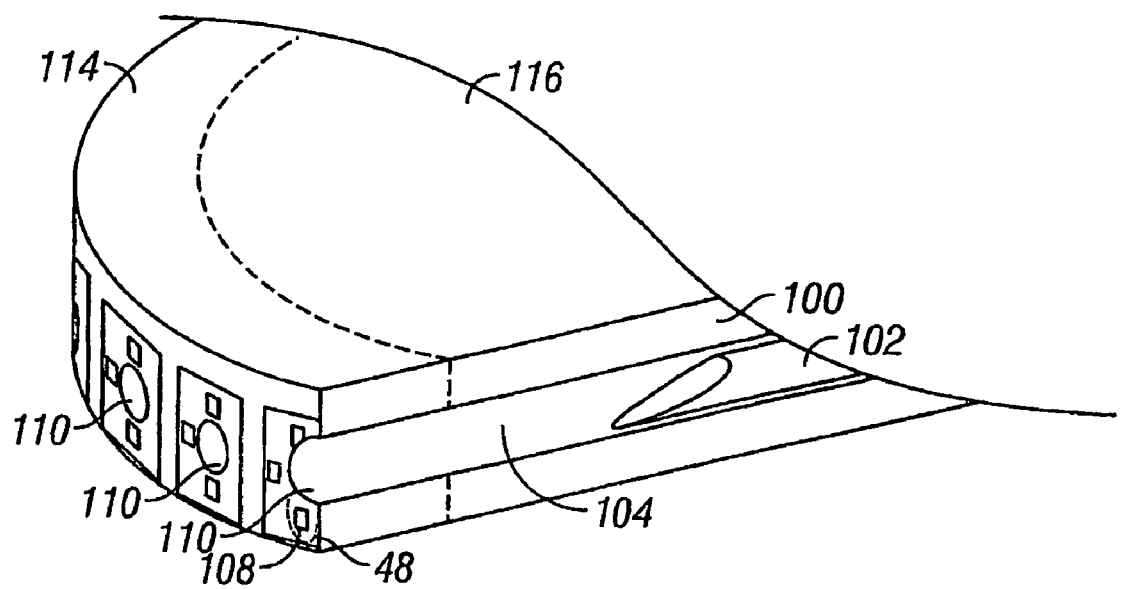
FIG. 6 shows a cross-section view of yet another embodiment of the present invention with texturing.

Referring now to FIG. 6, a cross-section of yet another embodiment of the present invention will now be described. This cross-section shows a cartridge 100 holding a penetrating member 102 in a cavity 104. From a wound created in target tissue by the penetrating member 102, body fluid will contact electrodes 108 positioned around the exit port 110 of the penetrating member 102. It should be understood that the electrodes 108 may be arranged in a variety of configurations about the exit port 110. Some embodiments may have all the electrodes 108 below the port 110. Some embodiments may have all of the electrodes 108 above the port 110. Some may have the members 108 distributed about the opening. Some embodiments may have a mesh that covers the members 108 or comes next to the members and brings body fluid to the members 108. In still other embodiments an outer ring portion 114 maybe formed separate from portion 116 and then the two portions are integrally joined to form a single integral unit. The joining may occur by adhesives, bonding, heat bonding, interlocking coupling, or other methods. This may facilitate manufacture of parts that may use different sterilization methods. A sterility seal (not shown) such as but not limited to a foil may be placed over the outer circumference of the ring and may be peeled back to open each individual port 110. In other embodiments, the sterility seal may be punched open by a device such as but not limited to a separate punch device, the penetrating member, or a combination of the two. By example and not limitation, the device may include texturing 48 around the electrodes 108 or a larger area of texturing 40 that surrounds all the electrodes at once (not shown).

Figure 7:
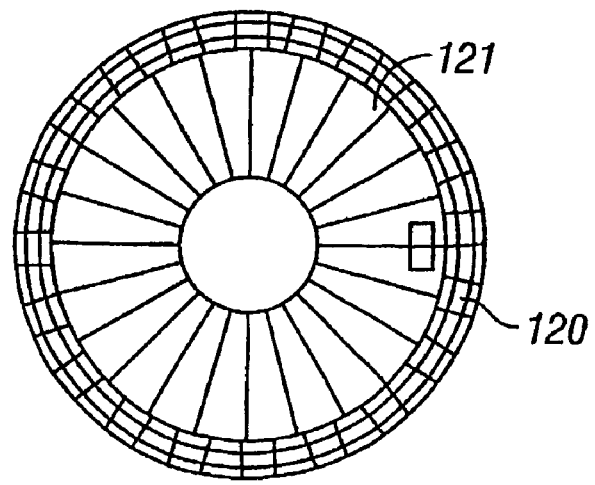
FIG. 7 shows one embodiment of a mesh for use with the present invention.

Referring now to FIG. 7, one embodiment of the present invention will now be described. Rather than let a droplet of body fluid build on the surface, one concept is to pull the droplet from the surface with, as a nonlimiting example, a fine mesh 120 that is located between the penetrating member and the finger. FIG. 7 shows a top down view of a radial cartridge 121 having the fine mesh 120. At the start position, the lancet mesh 120 may be located between the lancet tip and the foil. When cutting the foil, prior to the lancing event, the cutting instrument will spare the fragile mesh. In this embodiment, the amount of foil can be relatively limited because the mesh will be able to wick the blood down to the analyte detecting member. With the lancet tip being very sharp, the mesh 120 would be pushed to the side rather than cut. The resulting ring of capillary fibers around the wound channel would be available after the lancet was retracted to wick the blood sample into the sample channel.

Figure 8:
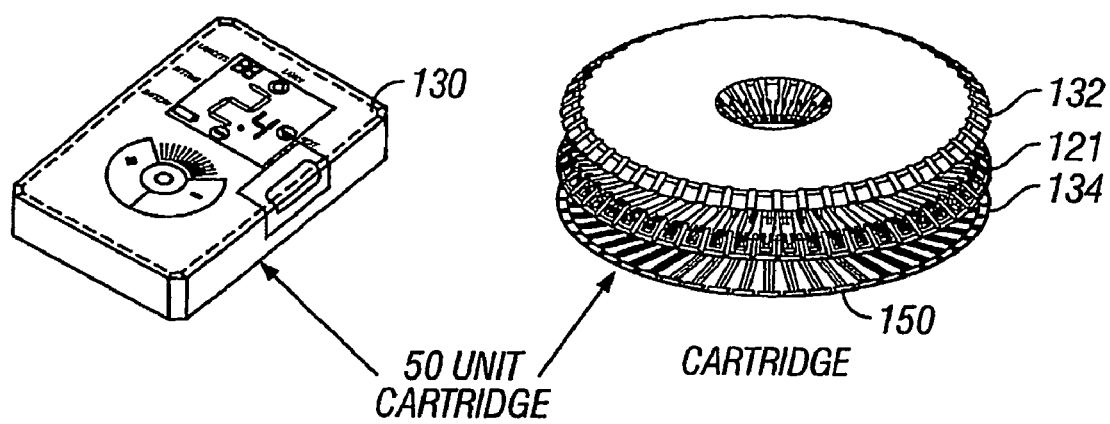
FIG. 8 shows perspective views of a fluid sampling device and a cartridge for use with such a device.

FIG. 8 shows the radial cartridge 121 for use with a lancing device 130. The radial cartridge 121 may be sealed with a sterility barrier 132 and be coupled to analyte detecting members mounted on a substrate 34. A suitable device is described in commonly assigned, copending U.S. patent application Ser. No. 10/429,196 fully incorporated herein by reference for all purposes.

Figure 9:
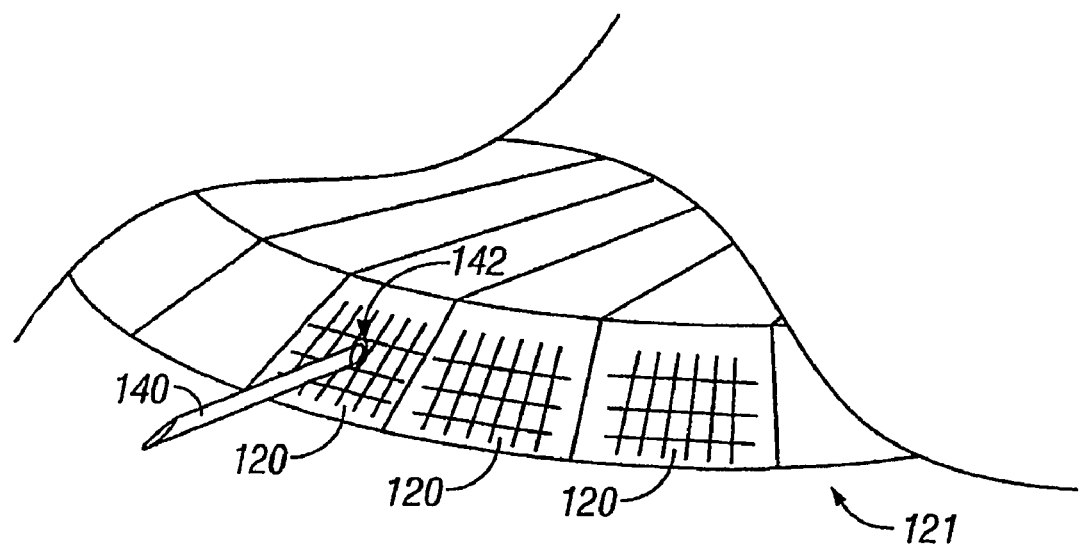
FIG. 9 shows a close-up view of one embodiment of a cartridge using mesh.

Referring now to FIG. 9, as described above, when a penetrating member 40 is actuated and extends outward from the cartridge 121, the mesh 120 is pushed aside or pierced by the exiting member 140. The resulting ring of capillary fibers 142 around the wound channel would be available after the lancet was retracted to wick the blood sample into the sample channel.

The physical characteristics of the mesh 120 is one aspect for successfully transport of blood to the analyte detecting member 150. In one embodiment, the mesh 120 could be pliable enough the allow relaxation, but maintain contact or near-contact with the skin surface. An active region could be striped on the mesh to allow the blood to only travel in the direction towards the analyte detecting member. A different gauge capillary fiber may be used on the mains versus the cross. In another embodiment, the mains may have a smaller gage and higher pitch to promote vertical movement. As an additional benefit, if the mesh assisted in distributing the force of lancet impact with the skin, the cutting efficiency of the lancet could be increased.

In another embodiment, the mesh 120 would reduce the amount of micropositioning used to assure that the droplet of body fluid gets to the analyte detecting member. The potential volume required by the analyte detecting member could be reduced by reducing the amount of blood or body fluid that spontaneously rises to the surface of the skin that is either not removed from the skin once the surface tension is released in a traditional, microfluidics methods. Traditional microfluidics could also have a higher volume required to get the blood to the sample chamber.

Figure 10:
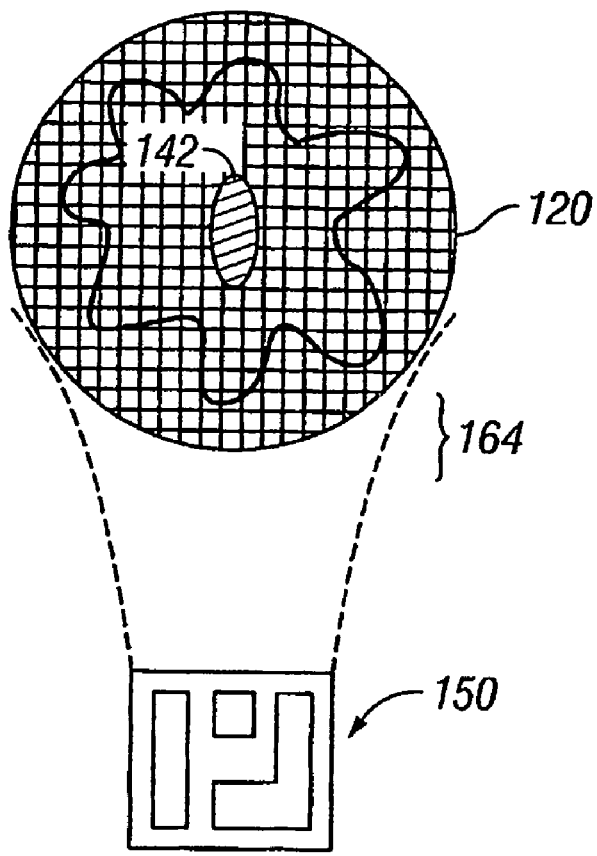
FIGS. 10-14 show other views of embodiments of mesh for use with the present invention.

Referring now to FIG. 10, it should be understood that the mesh may be configured to a variety of geometries. The mesh 120 could be fabricated as a ring as sees in FIG. 7 and then heat sealed into the analyte detecting member. The heat sealing should not effect the integrity of analyte detecting member. By example and limitation, the mesh 120 may also be used to cover at least one or more electrodes 68, 70, and 72 used in the device of FIG. 4. In some embodiments, the mesh 120 may also be used to cover the aperture 64.

Figure 11:
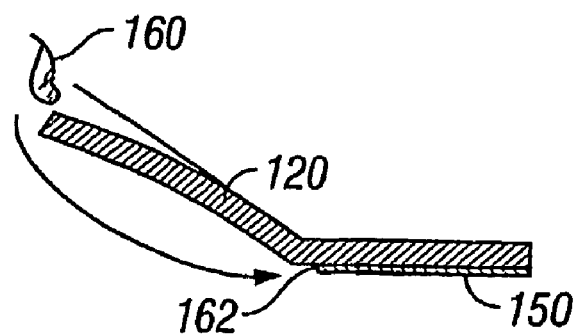

As seen in FIG. 11, the mesh 120 may be configured so that a blood droplet 160 that hits the mesh 120 will be drawn toward the analyte detecting member 150 as indicated by arrow 162, due to the length of the mesh 120 which is extended down to the member 150. As seen in FIG. 10, which is a top down view, the mesh 120 has portions 164 which may be extended down towards the member 150.

In one embodiment, a capillary mesh may be used that basically allows the lancet to fire through or the lancet can come around or through a lancet aperture in the mesh. The mesh in one embodiment may be a hydrophilic mesh that would then allow the blood to be absorbed, in this embodiment, once the droplet is built up on skin. With mesh, it does not matter where the droplet hits it. With a certain volume, there is enough blood to coat the mesh and coat the analyte detecting member, thus creating a better solution for integrated analyte detecting member.

Figure 12:
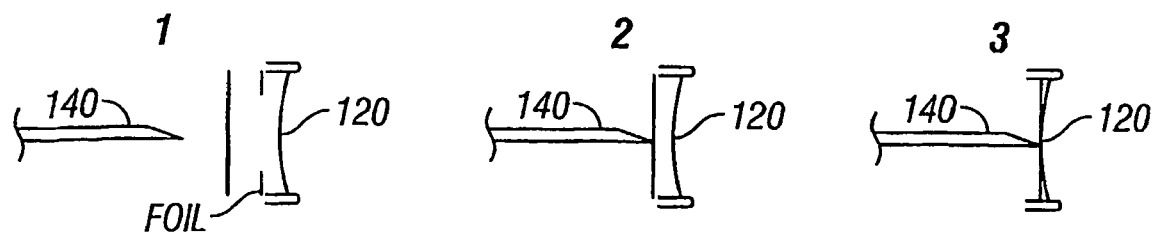

FIG. 12 shows one embodiment where the force of the penetrating member 140 impacting the mesh 120 flattens it out and pushes it against the skin. In this particular embodiment of mesh 120, the mesh 120 is pliable enough to allow relaxation.

One issue associated with the present invention may be getting the analyte detecting member close enough to the lancet. In many embodiments, the radial axis of the lancet is going to be where the droplet of body fluid is going to form. The pickup or transport is going to have to come to the droplet to acquire it.

In one embodiment, a layer of body fluid at least 50-100 microns thick is desired, and this is the thickness that the electrode needs to generate the glucose signal. So if the mesh is sandwiched on top of the electrode or if fluid is wicked along the capillary mesh, it is possible to repeatable transport blood to the analyte detecting member. Electrodes tend to be hydrophobic. But if there is a hydrophilic mesh, it will still travel to the mesh, even though the surface energy is low.

Figure 13:
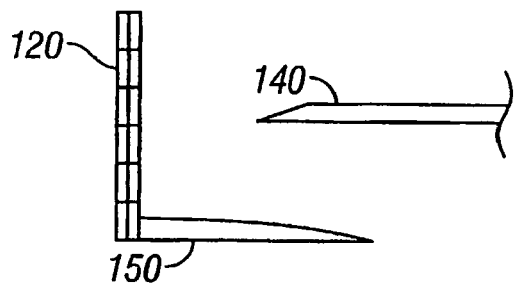

In another embodiment, a particularly high energy capillary mesh can be co-located at where the droplet is going to come which is at the axis of the lancet travel. The wicking member would be heat sealed to the electrode. Most preferable is a design where the wick is at about 90 degrees (i.e. vertical) as seen in FIG. 13.

Figure 14:
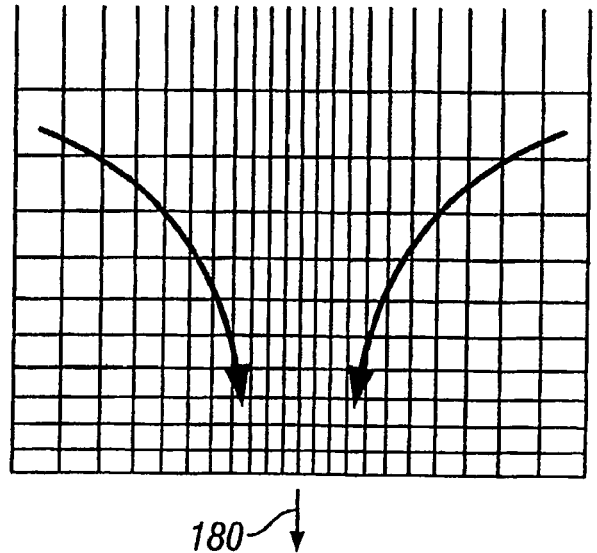

Referring now to FIG. 14, it should be understood that the mesh may be a gradient type of mesh. It may have high energy to pull one way as indicated by arrows 180. The crosses and the mains on the mesh may be designed and patterned to created a desired movement of fluid in contact with the mesh. The resulting effect is a gradient. A thinner gauge may be used in a higher energy area. With regard to the capillary size and the gaps, they are relatively proportionate. Of course, when you get down to a level below 100 microns, 70 microns for the pore size, the mesh can get into blood filtration or clogging of the blood, particulates such as the big lucocytes tend to clog and make the mesh unproductive/effective anyways. There is a limit to how much you can play with sizing of the mesh strands.

It should be understood, of course, that the present invention may operate with alternative embodiments. With the mesh, you may be able to use a hydrophilic spray. Or to create a highly texturized surface or other surface treatment, the mesh may direct the flow of fluid. In some alternative embodiments, a ribbed plastic without pores may be used. One limitation of traditional capillary structure is that when it gets too close to the skin, it tends to blanche or inhibit the movement of blood to the surface. So even if you have it perfectly located in a lateral, collateral direction. Such a capillary structure is vertically sensitive and sometimes does not get the blood as a result.

If the mesh is very compliant, then the vertical sensitivity problem/blanching is substantially resolved. The mesh could be co-located perfectly and touching the surface of the skin. And then you do not have a vertical offset or a vertical insensitivity problem that tends to blanche. Then because there is not a bearing surface there and pressure is kept at a level below that which would cause blanching.

Figure 15:
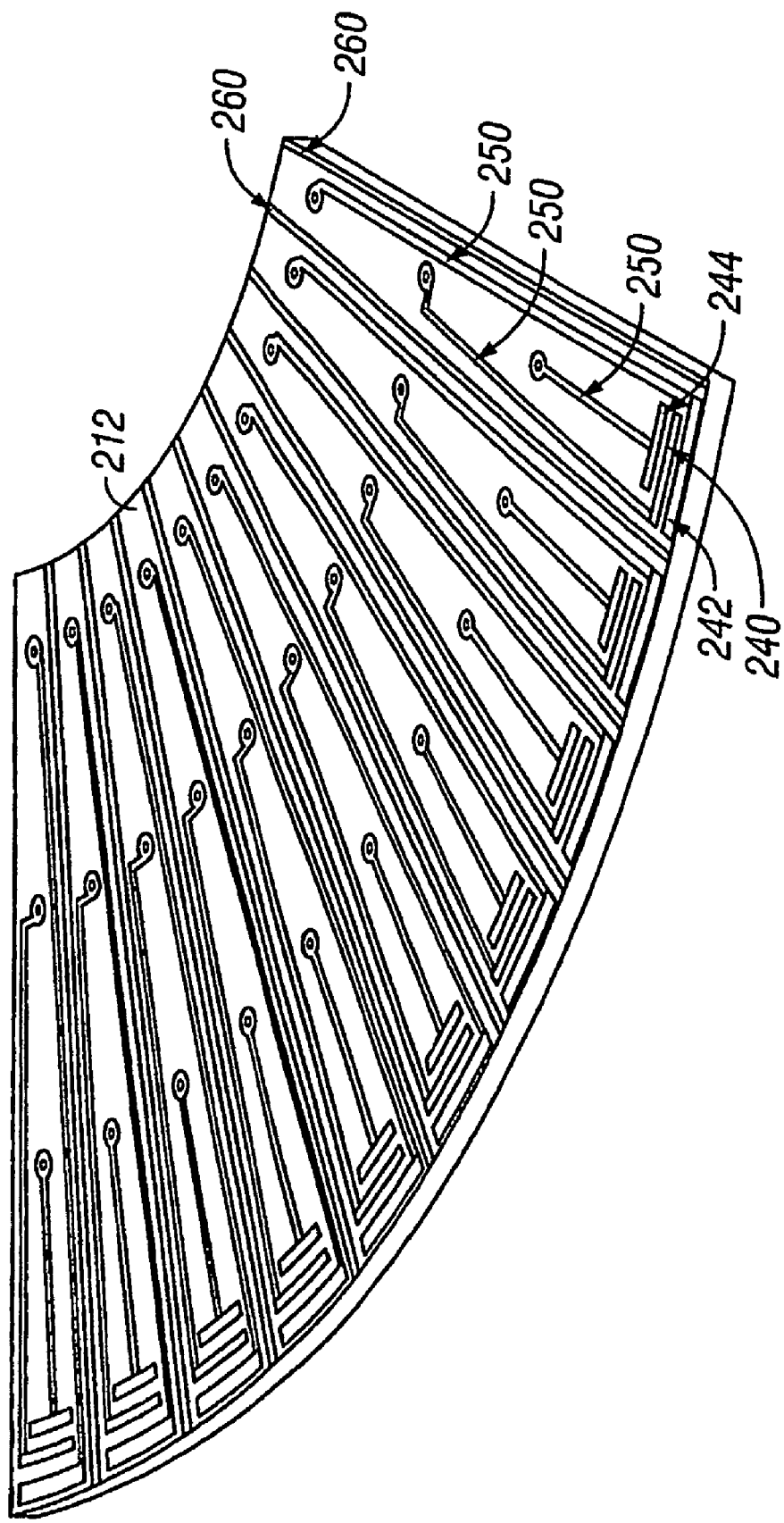
FIG. 15 shows one embodiment of electrical contacts and leads for use with the present invention.
Figure 16:
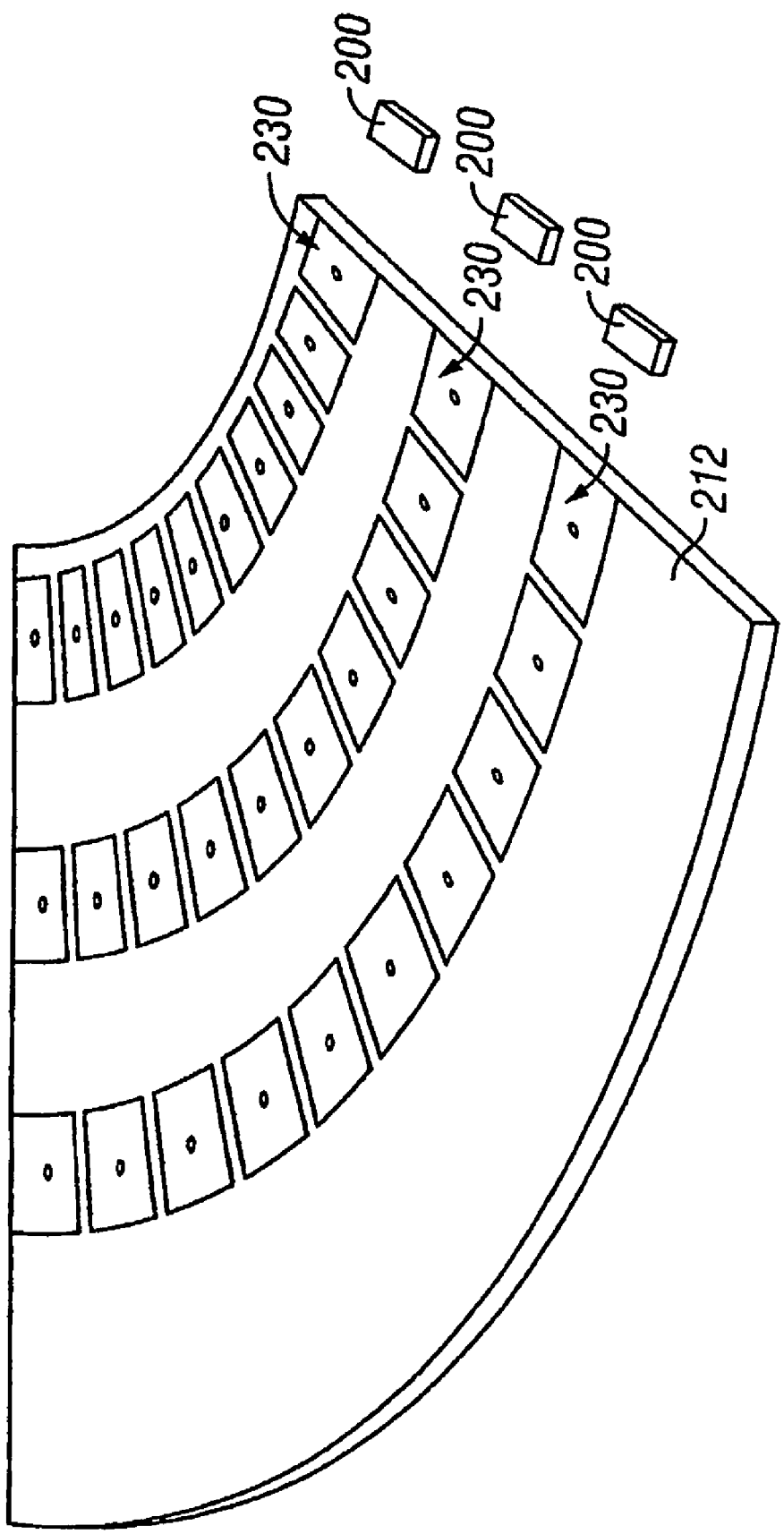
FIG. 16 shows one embodiment of the present invention with contact pads for use with commutators.

FIGS. 15 and 16 provide additional details of the line conductors, feed-throughs, and conductor pads. The embodiment shown in the FIGS. 15 and 16 may be adapted for use with a radial cartridge such as that shown in commonly assigned, co-pending U.S. patent application Ser. No. 10/429, 196 filed May 1, 2003, fully incorporated herein by reference for all purposes. For example and not limitation, FIG. 15 shows a support structure 212 that is adapted for use with a radial cartridge 20. The support 212 may include a plurality electrodes such as, but not limited to, a working electrode 240, a counter electrode 242, and a reference electrode 244. A plurality of conduction lines 250 may be used as leads to connect the electrodes having the sensory material 214 with the contact pad 230 on the other side of the support 212 (see FIG. 16). By example and not limitation, the contact pad 230 may be substantially larger in width than the conduction lines 250. This facilitates the tolerance of the pad to slight misalignments of the pad with connectors or contacts on a measurement device. The contact pads 230 are shown to be square or rectangular in geometry. It should be understood, however, that the contact pads 230 may be circular, oval, polygonal, triangular, any single combination of the geometries above, or any combination of any number of the geometries above. The via holes may also be sufficiently spaced apart such that there is sufficient space on the underside of the support structure to accommodate the larger contact pads 230.

In the present embodiment, the top side of the support 212 may include a sealing region 260. This sealing region 260 may be used to keep the sensor material 214 in a sealed environment prior to use.

Figure 17:
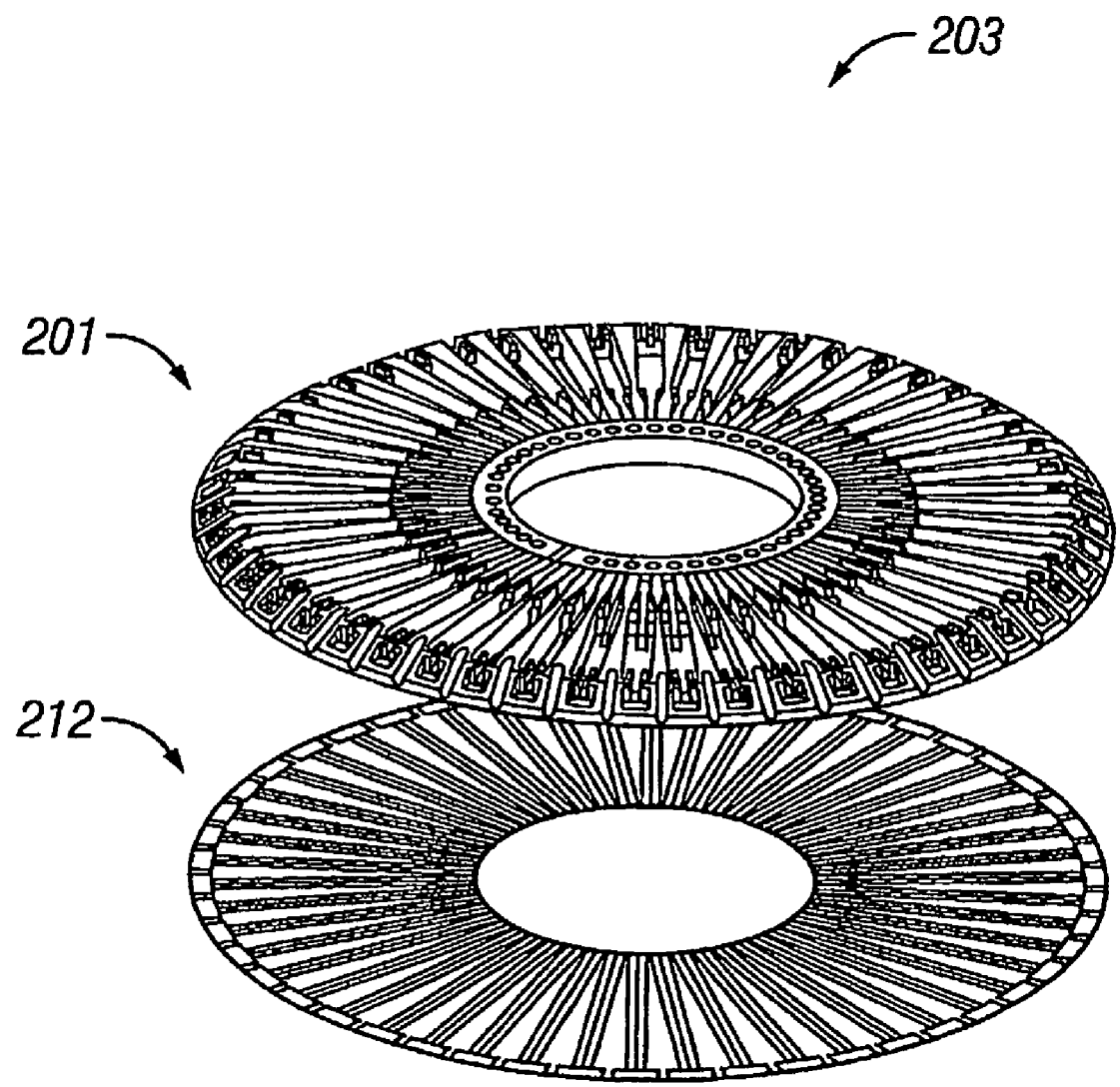
FIG. 17 shows an exploded view of a cartridge with an analyte detecting member layer.

FIG. 17 shows how one embodiment of a radial cartridge 201 may be coupled to a sterility barrier 203 and a support 212 having the sensor material 214 and contact pads 230. Of course, the support 212 of FIG. 17 may be configured to include configuration shown in FIGS. 15 and 16. The support 212 would be sealed, in one embodiment, against the underside of the radial cartridge 201. This integrates the sensory material 214 with the cartridge and also creates the sealed environment in which the material 214 may be stored until ready for use.

Embodiments of the present invention take the sensor electrode contact pad which for example and not limitation, may be located anywhere on the bottom on the package taking advantage of the disc shape. The electrode contact pads may be placed anywhere along the disc (between ID and OD). A commutator pickup may be used to make electrical contact. In one embodiment, a million insertion point probe may be used that is spring-loaded into the door or housing of the device. Other embodiments, by way of example and not limitation, may use gold plated sheet metal probes that are bent up. As the disc-shaped cartridge rotates, the next chamber rotates right in line with the contacts.

Figure 18:
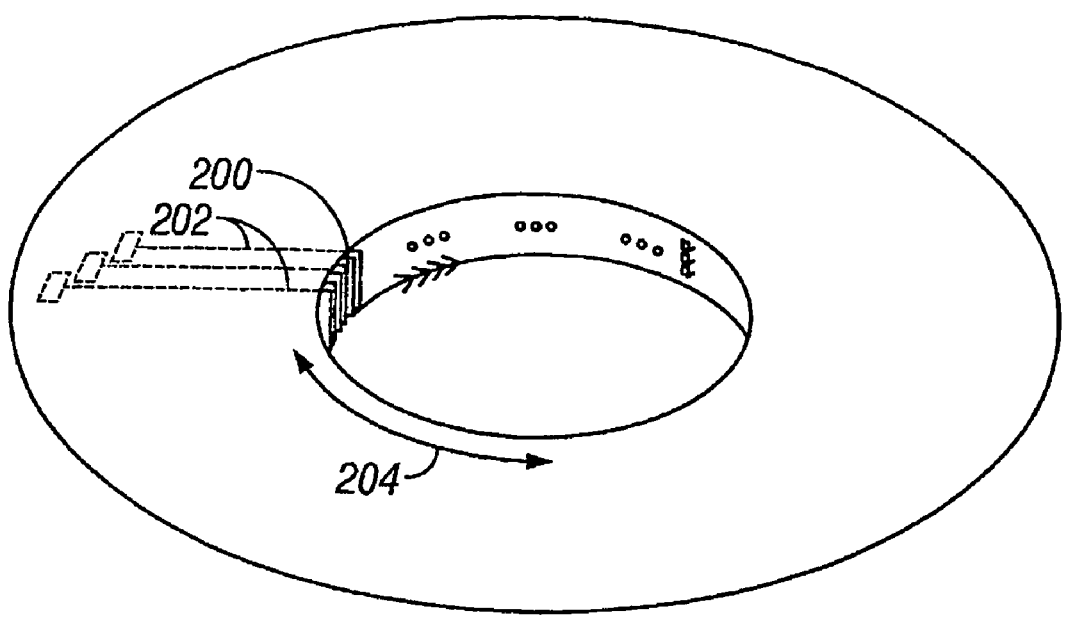
FIG. 18 shows a perspective view of one embodiment of the present invention for use with commutators on the inner diameter of the cartridge.

Referring now to FIG. 18, one embodiment of the present invention could use a commutator 200 to engage the electrode leads 202. The commutator 200 may be spring loaded to better engage the leads. As the cartridge rotates as indicated by arrows 204, those lead from electrodes in the active regions come in contact with the commutator 200. Referring back to FIG. 16, it can be sent that commutators 200 may be positioned to engage contact pads from the leads, where the pads 230 are not positioned in the inner diameter of the cartridge. The pads 230 may be on the underside, side, or somewhere along the length of the cartridge. It should be understood that a variety of commutators 200 are shown in FIG. 18. The device may have one set of commutators or it may have multiple sets. They may all have the same orientation or combinations of orientations. FIG. 18 shows side by side, vertical, and spring based versions. These are purely exemplary and are nonlimiting.

Figure 19:
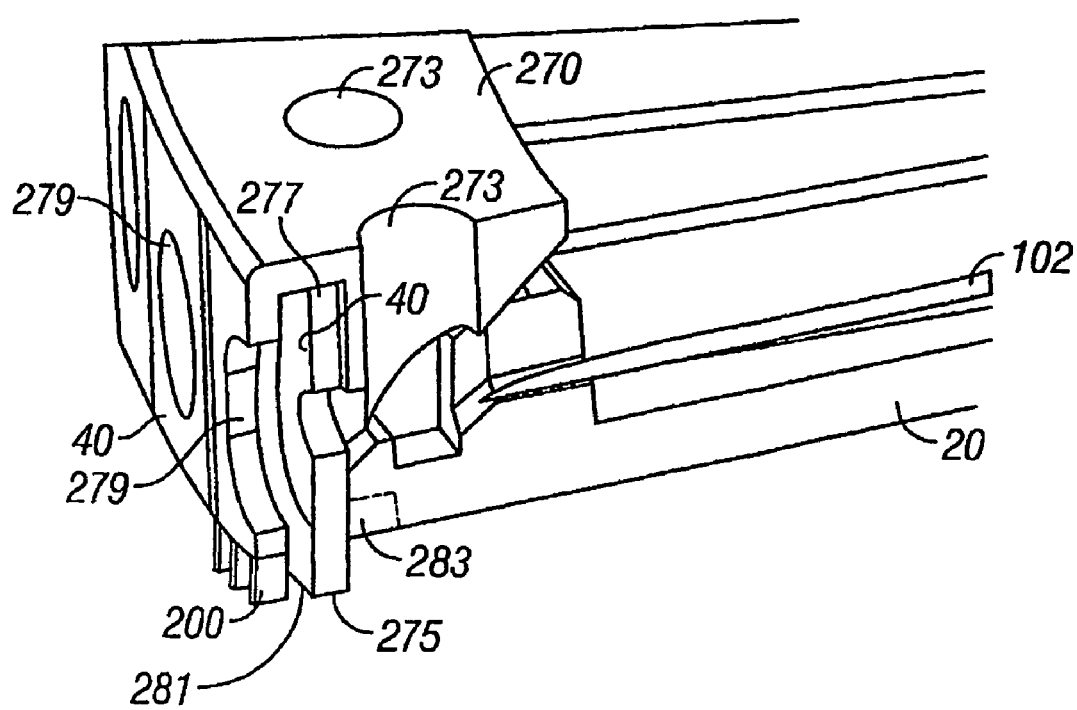
FIG. 19 shows a cross-sectional view of one embodiment of the present invention.

Referring now to FIG. 19, other embodiments may have the commutators on the outer diameter of the cartridge. FIG. 19 shows a cross-section of yet another embodiment of the present invention will now be described. FIG. 19 shows a cartridge 20 with a penetrating member 102. In one embodiment, a ring portion 270 is coupled to the cartridge 20. In some embodiments, the ring portion 270 may be integrally formed with the cartridge 20. In other embodiments, the two portions are integrally joined to form a single integral unit. The joining may occur by adhesives, bonding, heat bonding, interlocking coupling, or other methods. This may facilitate manufacture of parts that may use different sterilization methods. An opening 273 may be provided to allow any sterility seals on the cartridge 20 to be opened. A punch or other mechanism may extend down through the opening 273 to piece the seal and clear it from the path of the penetrating member 102.

As seen in FIG. 19, an analyte detecting member 275 may be housed in the portion 270. The analyte detecting member 275 may be similar to embodiments shown in FIGS. 110-112. A groove 1330 in the portion 270 may be formed to hold the member 275. A plurality of analyte detecting members 275 may also be placed on a ribbon and then placed in a groove 277 that runs around the circumference of the disc. Openings 279 allow for the penetrating member to exit. By way of example and not limitation, some embodiments may have texturing 40 around the openings 279 to control any wayward fluid flow. The texturing 40 may also be present on the detecting member 275.

FIG. 19 also shows that commutators 200 may also be used with the present invention. In some embodiments the commutators 200 may be spring loaded to press against contacts 281 to ensure a solid contact. By way example and not limitation, the contacts 281 and commutators may also be on the inner diameter of the analyte detecting member 275. Other embodiments may have the contacts 281 on the bottom of the analyte detecting member 275. Some embodiments may have the members 275 extend below the bottom surface of the cartridge 20 to facilitate engagement with the commutators 200. Other embodiments may have the bottom of the detecting member 275 substantially flush with the bottom surface of cartridge 20. The contact pad 281 may be on the bottom surface of the detecting member 275. In some embodiment, there may be a groove 283 (shown in phantom) that allows for commutators 200 to engage any contact pads on the inner diameter. In some embodiments, a similar groove may be on the outer diameter side to facilitate contact with contact pads on that side.

Figure 20:
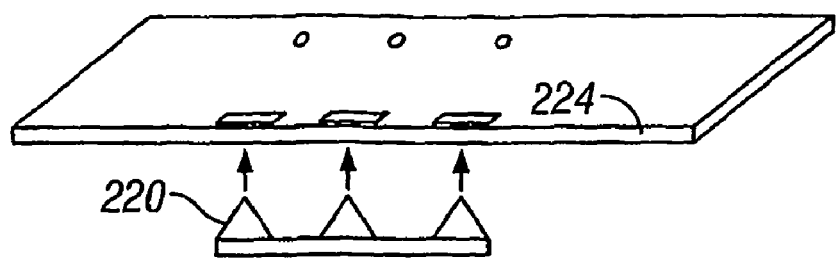
FIG. 20 shows yet another embodiment of the present invention.

Referring now to FIG. 20, a still further embodiment of the present invention will be described. In one embodiment of the lancing device, the cartridge goes in, foil-side up. If we print on sensors 218 in the chamber, you could have the probes 220 go through the printed material 224, making contact with the sensors. In this embodiment, electrodes at all. In some alternatives, cam action may be used to move the probes out of the way. They go back in, making contact with the next chamber when the cartridge is rotated into place. Thus to get rid of the electrodes, we want to make contact with the printed sensor using a needle probe which may be made by way of example and not limitation, laser etched gold. Alternative embodiments may use laminates. They use various thicknesses of materials. In some embodiments, the probes do not penetrate the sensors in a manner that contacts blood.

Figure 21:
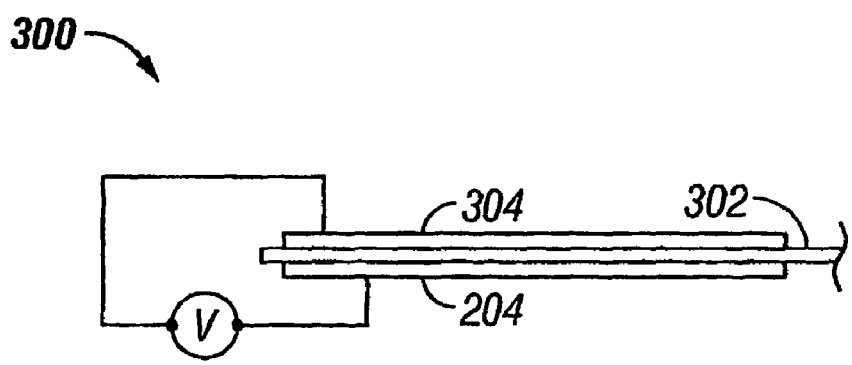
FIGS. 21-22 show side views of actuators according to the present invention.
Figure 22:
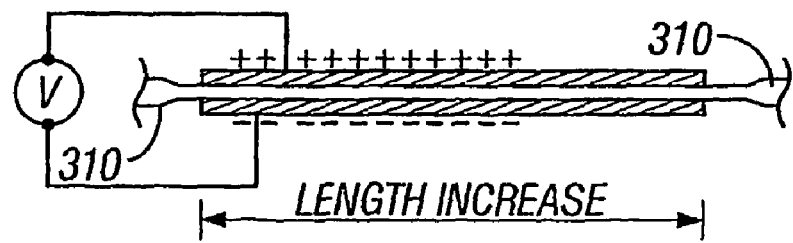

Referring now to FIG. 21, an embodiment of the present invention using an elastomeric actuator will now be described. The present invention consists of an electronic actuator 300 consisting of a soft elastomer sheet 302 with electrodes 304 applied to the opposing large surfaces. The geometry created is that of a capacitor. When electrical potential is applied to the electrodes, electrostatic forces attract the electrodes toward each other. As seen in FIG. 22, the intervening soft elastomer is displaced by the electrodes, lengthening the elastomer. This displaced material 310 acts to elongate the elastomer/electrode assembly. Because the elastomer grows in length, it is desirable in one embodiment to construct the electrodes from a compliant material, such as carbon-loaded silicone (SRI patent), so they can conform to the elongated elastomer.

Figure 23A:
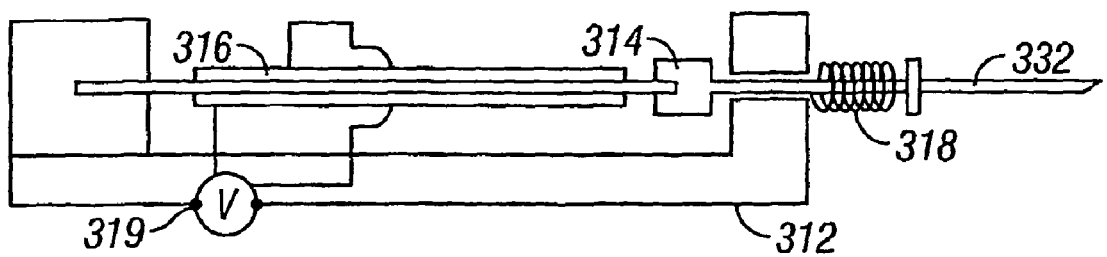
FIGS. 23A-23B show two different embodiments of actuators according to the present invention.

It has been observed that pre-stretching the elastomer (SRI) improves resistance to dielectric breakdown, and an extension of the operating voltage range. The actuator embodiment shown in FIG. 23A consists of a rigid frame 312 with a clamp 314 at one end to hold the elastomer. At the other end of the frame a guide bearing holds an actuator shaft that is clamped to the other end of the elastomer 316. A pre-stretch spring 318 tensions the elastomer. A controlled voltage source 319 applies actuating voltage to the electrodes on the elastomer.

Figure 23B:
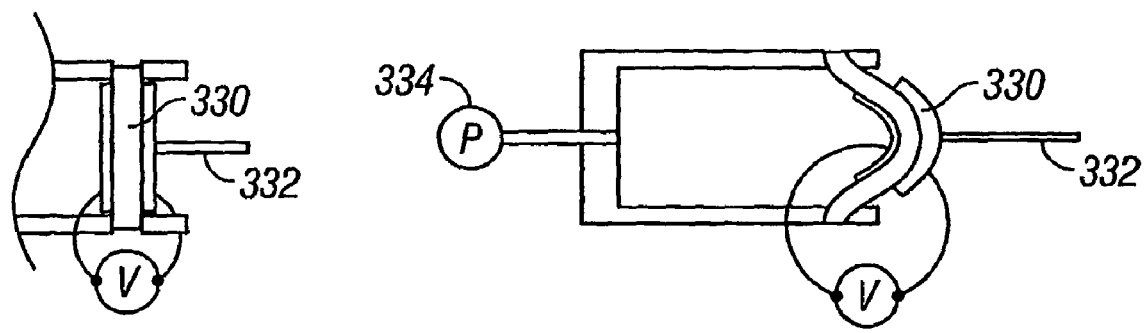

A second style of actuator shown in FIG. 23B consists of a pre-tensioned diaphragm 330 stretched over a chamber. In this embodiment, an actuator shaft 332 is attached to the center of the diaphragm 330, and may be guided by a bearing (not shown) if needed. Electrodes applied to the diaphragm 330 cause it to expand. To shape the diaphragm, and direct the resulting motion, a bias pressure from a source 334 is applied behind the diaphragm. The same function can be achieved by adding a bias spring to the actuation shaft.

Figure 24:
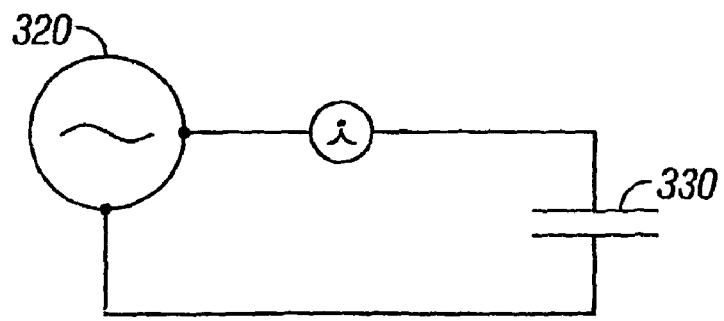
FIG. 24 is a schematic for determining position for an actuator according to the present invention.

Referring now to FIG. 24, one component of an actuator system is position feedback. A position signal can be obtained from an elastomeric actuator by measuring the capacitance of the actuator 330 (or 316). This can be accomplished by imposing a sine wave, or pulse signal 320 onto the DC drive voltage. The current resulting from this sensing signal is a measure of the capacitance of the actuator, and hence the deflection of the electrode plates.

As seen in FIGS. 25 and 26, a variety of feedback systems and velocity profiles may be used to control the motion provided by actuator 330 or 316. As discussed above, tissue penetration devices which employ spring or cam driving methods have a symmetrical or nearly symmetrical actuation displacement and velocity profiles on the advancement and retraction of the penetrating member as shown in FIGS. 25 and 26. In most of the available lancet devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

Figure 25A:
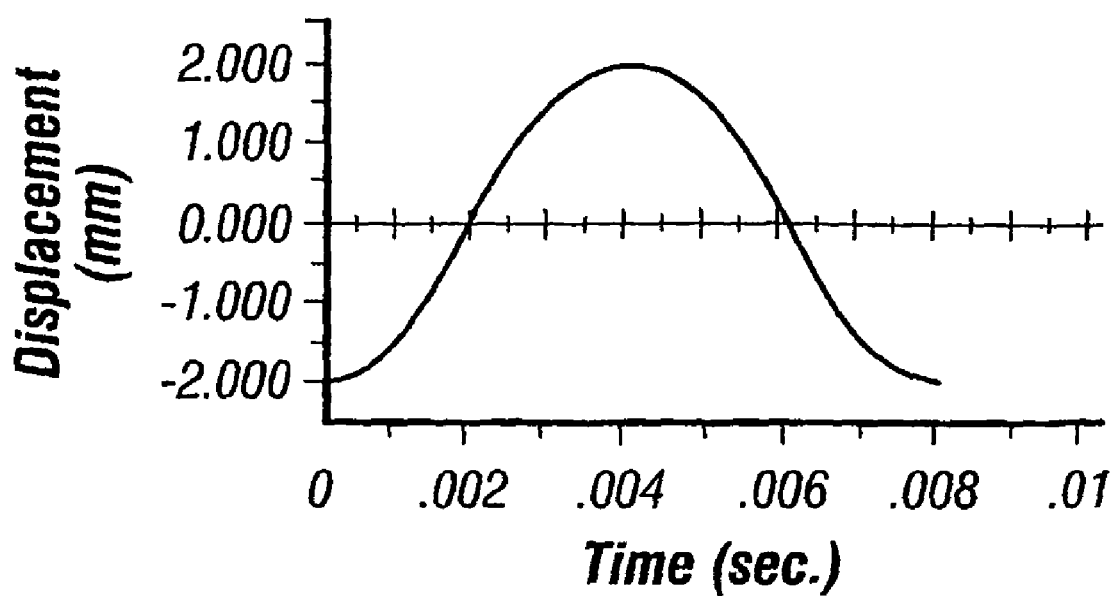
FIGS. 25A-25D show penetrating member velocity profiles.
Figure 25B:
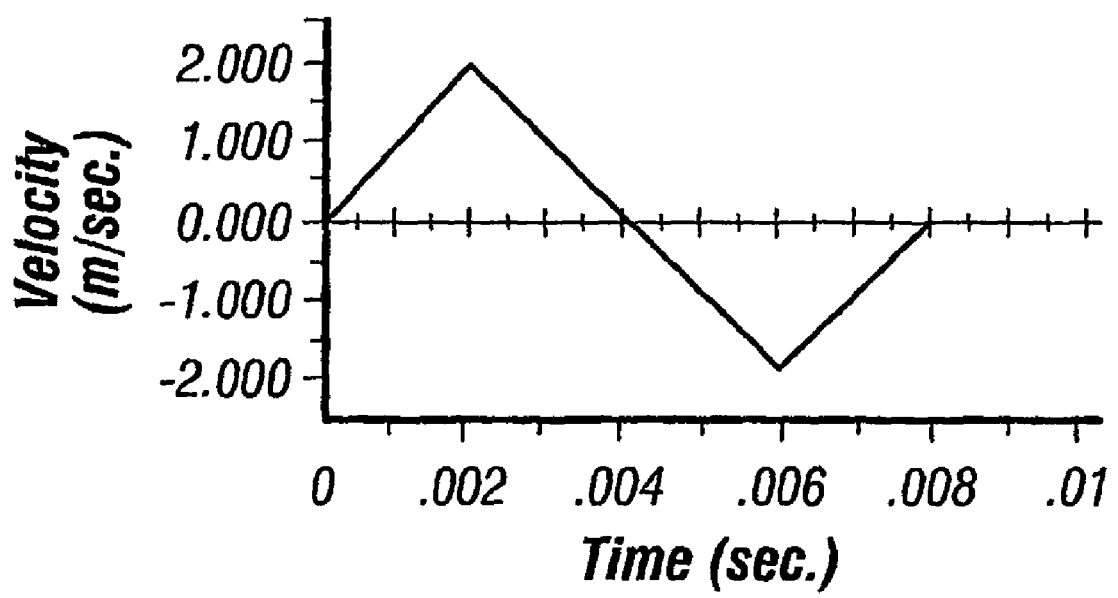
Figure 25C:
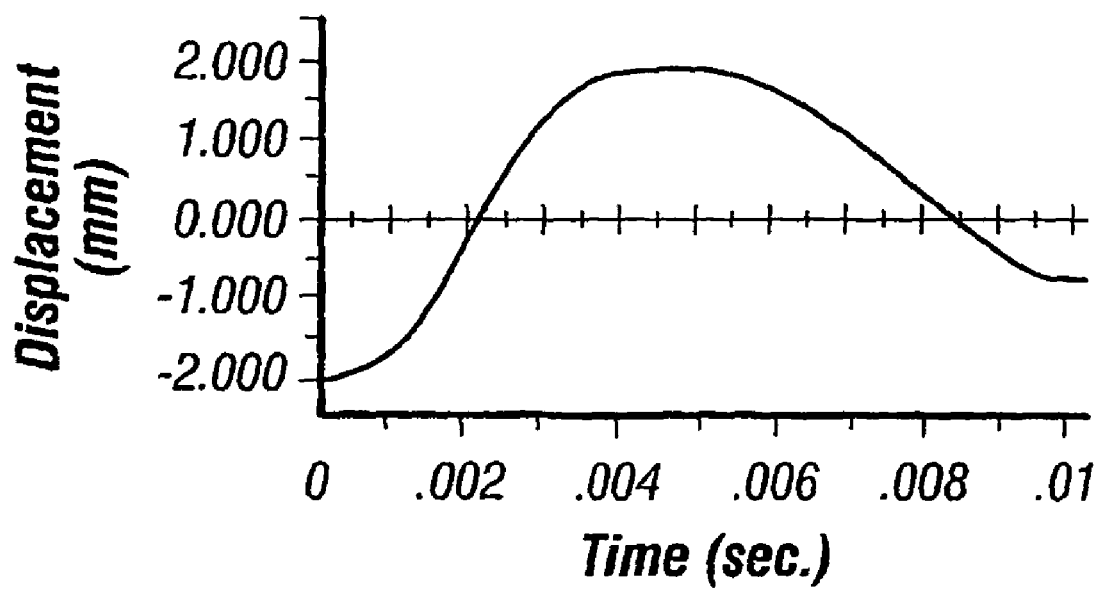
Figure 25D:
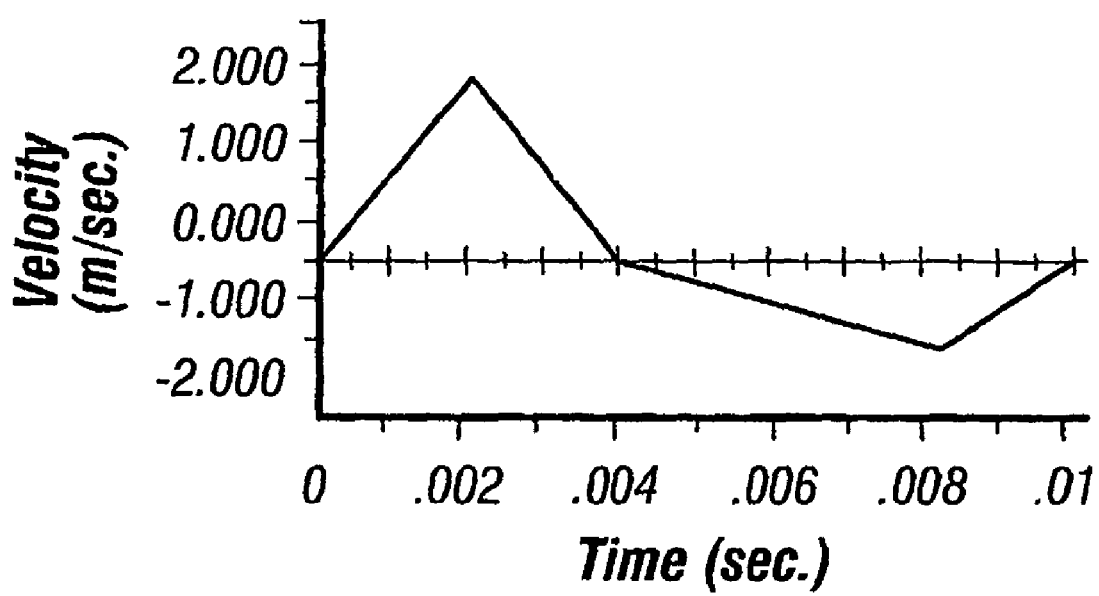

In this embodiment, the ability to control velocity and depth of penetration may be achieved by use of a controllable force driver where feedback is an integral part of driver control. Such drivers can control either metal or polymeric penetrating members or any other type of tissue penetration element. The dynamic control of such a driver is illustrated in FIG. 25C which illustrates an embodiment of a controlled displacement profile and FIG. 25D which illustrates an embodiment of a the controlled velocity profile. These are compared to FIGS. 25A and 25B, which illustrate embodiments of displacement and velocity profiles, respectively, of a harmonic spring/mass powered driver. Reduced pain can be achieved by using impact velocities of greater than about 2 m/s entry of a tissue penetrating element, such as a lancet, into tissue. Other suitable embodiments of the penetrating member driver are described in commonly assigned, copending U.S. patent application Ser. No. 10/127,395 filed Apr. 19, 2002 and previously incorporated herein.

FIG. 26 illustrates the operation of a feedback loop using a processor 360. The processor 360 stores profiles 362 in non-volatile memory. A user inputs information 364 about the desired circumstances or parameters for a lancing event. The processor 360 selects a driver profile 362 from a set of alternative driver profiles that have been preprogrammed in the processor 360 based on typical or desired tissue penetration device performance determined through testing at the factory or as programmed in by the operator. The processor 360 may customize by either scaling or modifying the profile based on additional user input information 364. Once the processor has chosen and customized the profile, the processor 360 is ready to modulate the power from the power supply 366 to the penetrating member driver 368 through an amplifier 370. The processor 360 may measure the location of the penetrating member 372 using a position sensing mechanism 374 through an analog to digital converter 376 linear encoder or other such transducer. Examples of position sensing mechanisms have been described in the embodiments above and may be found in the specification for commonly assigned, copending U.S. patent application Ser. No. 10/127,395, filed Apr. 19, 2002 and previously incorporated herein. The processor 360 calculates the movement of the penetrating member by comparing the actual profile of the penetrating member to the predetermined profile. The processor 360 modulates the power to the penetrating member driver 368 through a signal generator 378, which may control the amplifier 370 so that the actual velocity profile of the penetrating member does not exceed the predetermined profile by more than a preset error limit. The error limit is the accuracy in the control of the penetrating member.

After the lancing event, the processor 360 can allow the user to rank the results of the lancing event. The processor 360 stores these results and constructs a database 80 for the individual user. Using the database 379, the processor 360 calculates the profile traits such as degree of painlessness, success rate, and blood volume for various profiles 362 depending on user input information 364 to optimize the profile to the individual user for subsequent lancing cycles. These profile traits depend on the characteristic phases of penetrating member advancement and retraction. The processor 360 uses these calculations to optimize profiles 362 for each user. In addition to user input information 364, an internal clock allows storage in the database 379 of information such as the time of day to generate a time stamp for the lancing event and the time between lancing events to anticipate the user's diurnal needs. The database stores information and statistics for each user and each profile that particular user uses.

In addition to varying the profiles, the processor 360 can be used to calculate the appropriate penetrating member diameter and geometry suitable to realize the blood volume required by the user. For example, if the user requires about 1-5 microliter volume of blood, the processor 360 may select a 200 micron diameter penetrating member to achieve these results. For each class of penetrating member, both diameter and penetrating member tip geometry, is stored in the processor 360 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

An article titled Artificial Muscles in the October 2003 issue of Scientific American is incorporated herein by reference for all purposes.

Referring now to FIG. 27, yet another embodiment of the present invention will now be discussed. Mathematical modeling of microscale processes is a uniquely useful alternative to the known approaches since the chemical and physical processes in the microscale generally follow deterministic physical laws that can be accurately represented in mathematical models. Once validated by external measurements, modeling can predict internal behavior at any point in space and time within the microdevice, leading to new insights and optimization techniques, e.g., the accurate fitting of non-linear response functions, optimization of system dynamics, or location of a specific region of incomplete reagent mixing, complete with design modifications that will remedy the problem.

Many developers of microdevices utilize this very powerful approach of simultaneous modeling and experimentation. Microscale fluid movers have been developed using both linear[3-5] and nonlinear[6-8] modeling, even when complex fluids such as particle suspensions[10,11] are involved. Other components of microfluidic systems[12-17] have benefited from this dual approach as well.

The large surface-to-volume ratio characteristic of microdevices, however, frequently leads to unexpected behaviors. For example, microvolumes of physiological fluids evaporate, cool, and heat extremely rapidly and modeling is often desirable to accommodate, or leverage, such heat transfer and evaporation processes and their impact on the system. At the typical low Reynolds-number (slow flows) in microdevices, mixing is often problematic and modeling guides the design to achieve mixing requirements.

The modeling of laminar flow is rarely an end in itself, but since the exact governing equations can be solved analytically in simple channels, or numerically in more complex channels, this produces valuable knowledge of the flowfield and its effect on other important physical processes, for example the precise control of chemical reaction rate by designing the diffusive mixing of the reactants. A multiphysics model is the result and is extremely useful to experimentalists tasked with sorting out the effects of a microdevice with complex physics. Many researchers have utilized this approach to develop devices for fluid constituent extraction[18], property measurement such as pH[19], viscosity[20], and diffusion coefficient[21], quantitative analysis[22], sample preparation[23], and laminate-based microfluidic devices for biomedical applications[24-28].

To illustrate how modeling can speed the development of diagnostic products, the present application discusses using one embodiment of the present invention to model a microscale processes to speed development of a microfabricated glucose detecting member.

Referring now to FIGS. 27A and 27B, effort has been made to develop a novel microfabricated point-of-use glucose detecting member to be integrated within an automated low-volume lancet-based blood collection device. In a nonlimiting embodiment, the blood collection device is optimized to achieve almost painless blood acquisition of approximately 200 mL per sample ($\frac{1}{100}^{th}$ of a drop of blood). It should be understood, of course, that other volumes such as about 500 nl, 400 nl, 300 nl, 200 nl, 100 nl, 60 nl or less can also be used in other embodiments of the invention. A new integrated glucose detecting member was developed to be compatible with such small fluid volumes, as well as, for example and not limitation, a sub-10 second response time and an accuracy of ±5% over the clinical range. FIG. 27B shows one embodiment of the prototype analyte detecting member arrangement as well as the integrated glucose lancing device. The analyte detecting members may be clustered in units of five for each sample measurement and within a microchannel along which a blood sample flows.

The present invention focuses here on the analyte detecting member itself, a new type of fluorescence-optical glucose biosensor. In one embodiment, the membrane comprises an emulsion that incorporates the enzyme glucose oxidase (GOX) to catalytically consume sample glucose and co-consume oxygen. The emulsion additionally contains an oxygen-quenchable fluorescent indicator that determines the concentration, and hence consumption, of oxygen within the analyte detecting member by a change in fluorescence and thus is related to the sample glucose concentration. The indicator is contained in dispersed hydrophobic droplets within a hydrophilic matrix containing GOX. The use of an emulsion enables single-step deposition of the analyte detecting member, avoiding much complexity in manufacturing and maintains optimal micro-environments for the GOX and the fluorescent indicator. Other significant advantages such as faster response times are expected.

Figure 28:
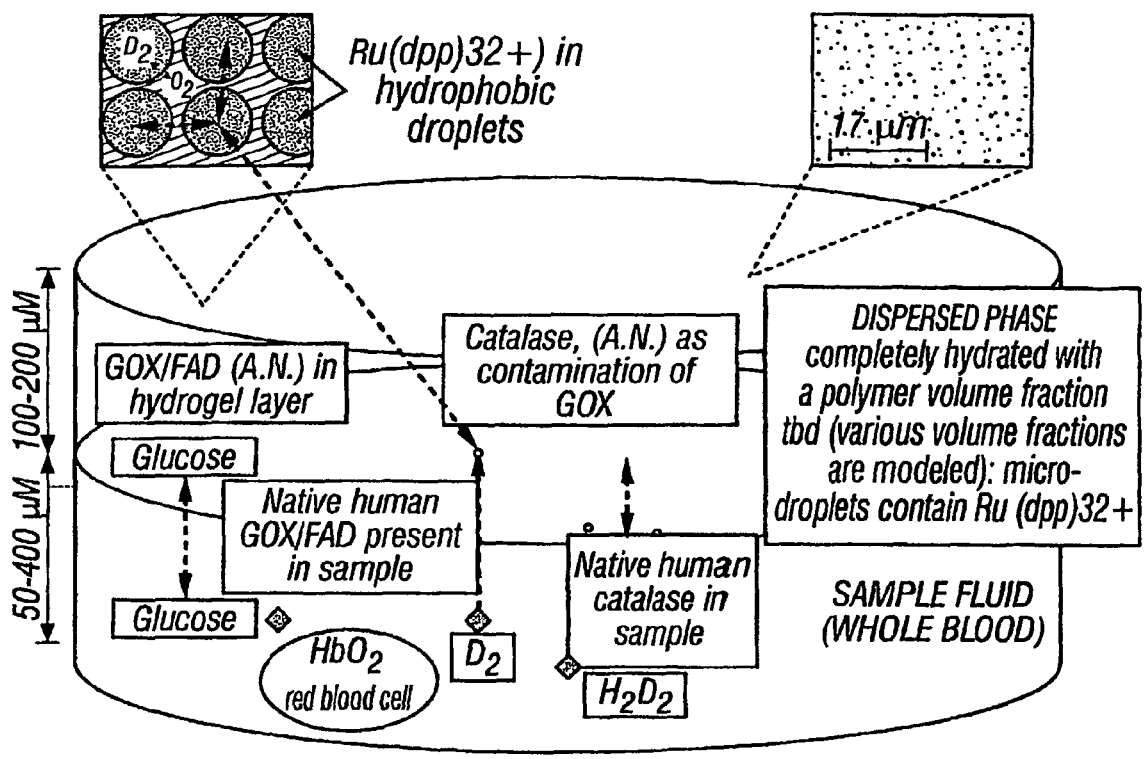
FIG. 28 is a diagram showing the analyte detecting member as modeled after initial contact of the member and the fluid sample.

The analyte detecting member model mathematically replicates the significant physical and chemical processes taking place in the analyte detecting member and sample. FIG. 28 provides a simplified schematic of the most important processes.

Prior to contact between the sample and the analyte detecting member layers, the whole blood sample contains red blood cells (RBCs) at a given hematocrit level and plasma with dissolved oxygen (bound to hemoglobin inside the RBCs and equilibrated with the surrounding plasma), human catalase (with no significant exchange of catalase between RBCs and plasma), glucose (which is the analyte), and hydrogen peroxide. In this embodiment, the sample is assumed to contain no GOX at this point. Other blood constituents that diffuse into the analyte detecting member layer are not expected to have a significant impact on the analyte detecting member chemistry at the concentrations they can reach within 60 seconds after exposure.

Prior to sample contact, the analyte detecting member membrane (dispersed-phase) contains a fluorescent indicator in the form of a ruthenium complex immobilized within microdroplets of a hydrophobic material (a siloxane-containing polymer) that are of known concentration and size distribution and embedded in a continuous hydrogel matrix of known water, polymer, and GOX content (see photo in FIG. 28). The membrane additionally has an oxygen concentration in equilibrium with the atmosphere.

When the analyte detecting member is initially exposed to the sample, the diffusion of all species is affected by the presence of the dispersed hydrophobic droplets; depending on the diffusion and partition coefficient of the each diffusing species, their diffusion rate may be increased or decreased. GOX starts to diffuse out of the analyte detecting member and into the sample at a slower rate than that of the small diffusants. As the glucose molecules reach the GOX molecules, they are metabolized and converted, with the co-consumption of oxygen and production of hydrogen peroxide, to gluconic acid, which in turn is instantaneously and non-reversibly hydrolyzed to gluconolactone.

In the present embodiment, the ruthenium complex (ruthenium-diphenylphenantroline $Ru(dpp)_3^{2+}$) in the hydrophobic microdroplets is initially in equilibrium with the ambient oxygen concentration, and its fluorescent lifetime is quenched to some degree. As oxygen is consumed by the GOX enzyme reaction a concentration gradient is generated between the hydrophobic microdroplets and the surrounding hydrogel, causing the diffusion of oxygen out of the microdroplets. At the same time, oxygen from the plasma in the sample (continually replenished by the RBCS) is diffusing into the analyte detecting member and locally counteracting the reduction in oxygen concentration accomplished by the GOX enzyme reaction. The net effect is a location-dependent reduction in the oxygen concentration in the microdroplets. The dispersed ruthenium complex within the microdroplets is thus quenched to a value somewhere between the values for ambient and for about 0 mbar oxygen. By way of example and not limitation, fluorescence lifetimes for these systems tend to be in the low microsecond range.

Modeling Methodology

In one embodiment of the present invention, the analyte detecting member model mathematically implements the physics of the analyte detecting member as described above. It divides the assay time into small time steps and the analyte detecting member into small control volumes. By way of example and not limitation, in the current embodiment, during each time step (and in each control volume), the model simultaneously solves a specie conservation equation for each important constituent: oxygen, glucose, glucose oxidase, catalase, and hydrogen peroxide. Each conservation equation includes an accumulation term, a diffusion term, and a production/destruction term. The latter relies on a production rate calculated either as a Michaelis-Menton reaction (catalase) or Ping-Pong Bi-Bi reaction (glucose oxidase).

The analyte detecting member model may track the diffusion of each important chemical component of the emulsion and sample, the chemical reactions between them, and the resulting signal from oxygen depletion. When the oxygen mass transfer rate between the hydrophobic droplet and surrounding hydrogel is as fast as the mass transfer rate of oxygen and glucose in the hydrophilic phase by diffusion, the concentration of oxygen in a droplet and the surrounding hydrophilic phase will always be close to equilibrium. This depends mainly on droplet diameter and diffusion coefficients, and is true for this analyte detecting member emulsion when the droplets are less than 5 microns in diameter. This rapid equilibration allows a welcome simplification in that the emulsion can be considered a single continuous material with averaged properties, instead of two segregated materials, one for each phase, requiring constant updating of the local oxygen flux between them.

Thus, the analyte detecting member model treats the emulsion as a continuum with properties based on volume-fraction averages of the properties of the hydrophobic and hydrophilic phases. The volume-averaged properties include: diffusion coefficient, solubility, and initial concentrations of each conserved chemical species. Using oxygen concentration in the analyte detecting member membrane as an example, the initial concentration (mM) is $$[O_2] = f_{Aq} S_{O2\ Aq} + f_{Si} S_{O2\ Si},$$

the effective partition coefficient is $$H_{O2} = f_{Aq} + f_{Si} \frac{S_{O2Si}}{S_{O2Aq}},$$

and the diffusion coefficient $$D_{O2} = f_{Aq} D_{O2\ Aq} + f_{Poly}(1 - f_{Si}) D_{O2\ Poly} + f_{Si} D_{O2\ Si}$$

where $f_{Si}$ is the volume fraction of the emulsion that is hydrophobic phase, $f_{Aq}$ and $f_{Poly}$ are the volume fractions of the hydrophilic phase that are aqueous and polymer, respectively. The diffusion coefficients of oxygen in water, hydrogel polymer, and hydrophobic phase are $D_{O2\ Aq}$, $D_{O2\ Poly}$, and $D_{O2\ Si}$. Finally, the solubilities of oxygen in water and hydrophobic phase at initial conditions are $S_{O2\ Aq}$ and $S_{O2\ Si}$ in mM units.

Solution of each constituent's conservation equation, each impacted by chemical reactions with other constituents, produces the predicted concentrations of oxygen, glucose, glucose oxidase, catalase, and hydrogen peroxide at every location in the analyte detecting member membrane and sample, as shown in the FIGS. 29 to 33.

Results from Model and Experiment

The following sets of plots illustrate some of the information generated by the model and the corresponding experiment for one set of initial conditions and analyte detecting member parameters. In these plots we used glucose-loaded saline solutions to provide tightly-controlled samples.

Figure 29A:
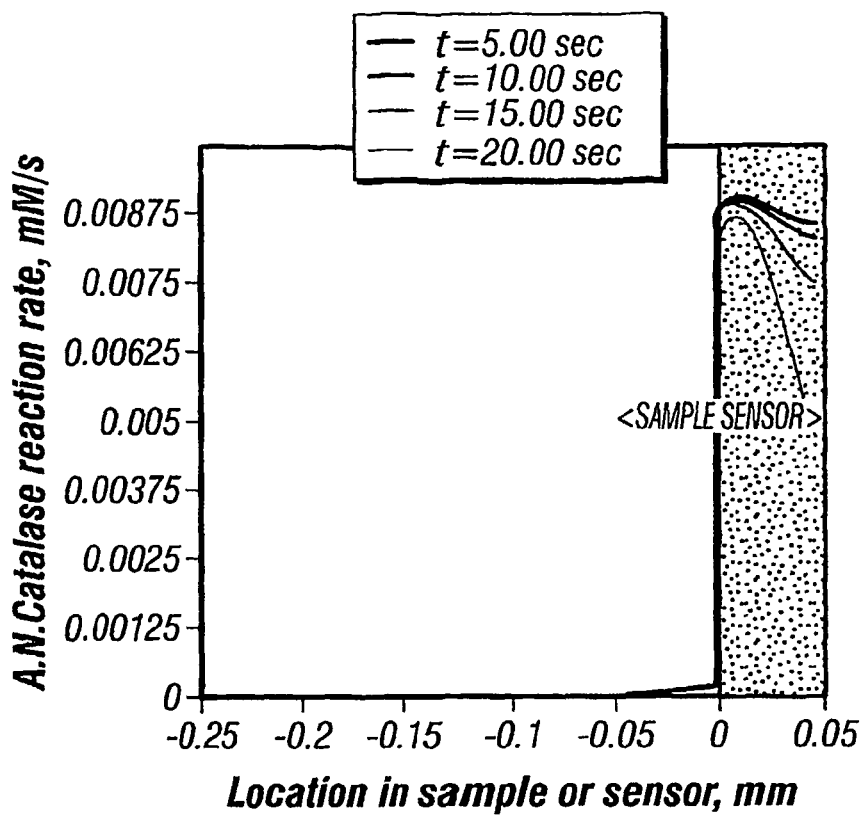
FIGS. 29a and 29b are charts showing reaction rates of enzyme reactions on the sample-sensor interface.
Figure 29B:
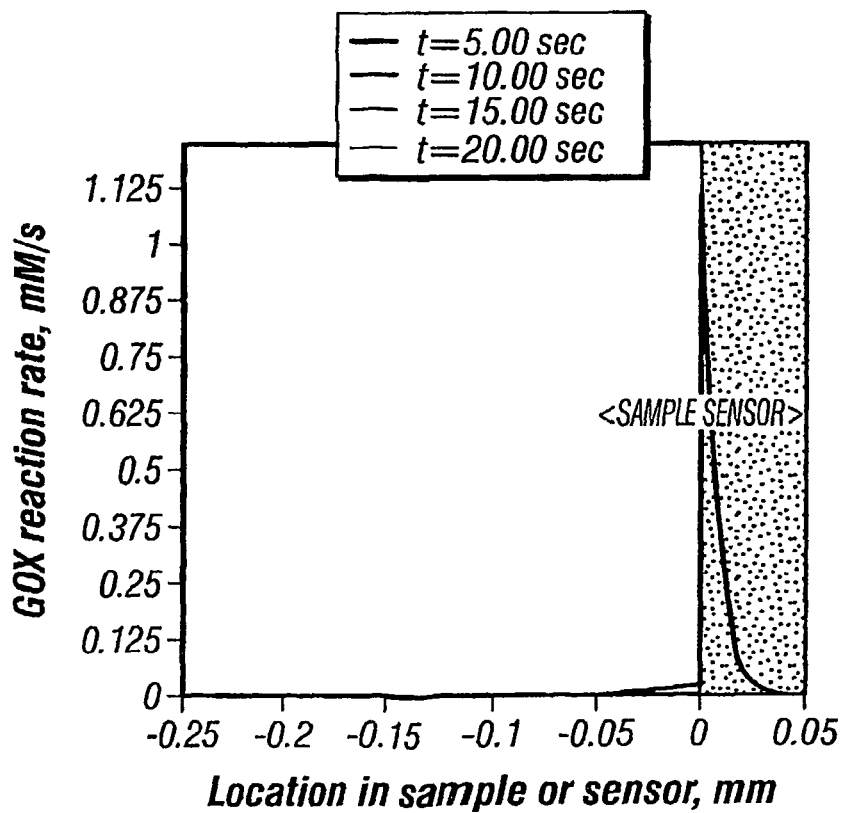

FIG. 29a shows the reaction rate for catalase from *Aspergillus niger* (as contaminant of GOX) and, in FIG. 29b, glucose oxidase from *Aspergillus niger* as a function of cross-sectional distance through the sample (1 mm on the left) and analyte detecting member (0.047 mm). Enzyme reaction rates are in mM/s. The curves correspond to 5, 10, 15, and 20 seconds after the exposure of the analyte detecting member membrane to the sample. Both reactions occur almost solely in the analyte detecting member; their initial rates are the highest.

Figure 30A:
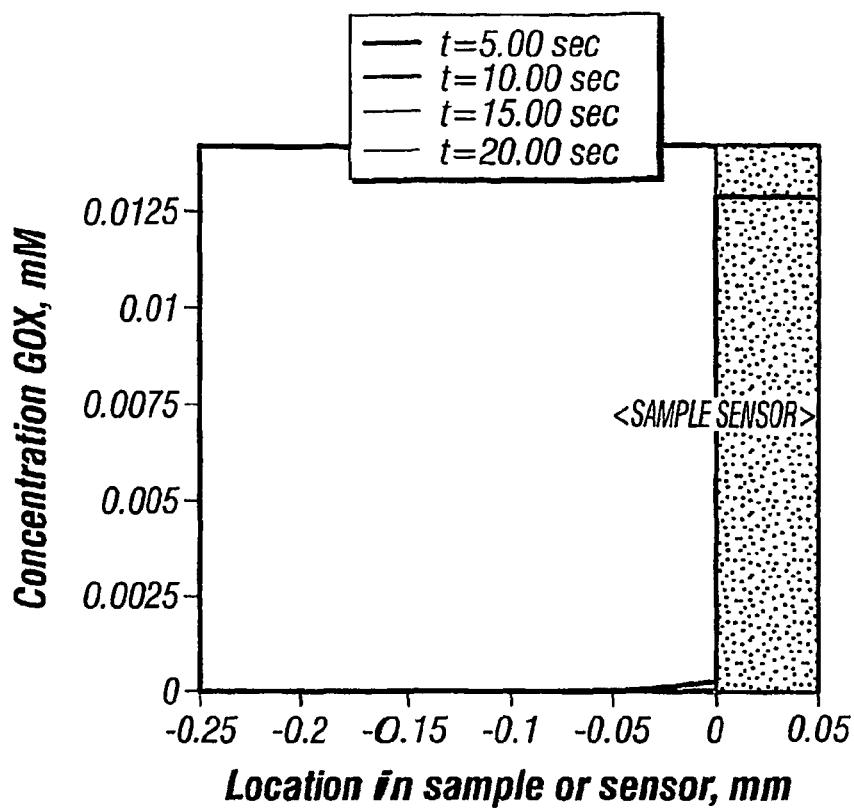
FIGS. 30a and 30b are charts showing concentrations profile of enzymes along the sample-sensor interface.
Figure 30B:
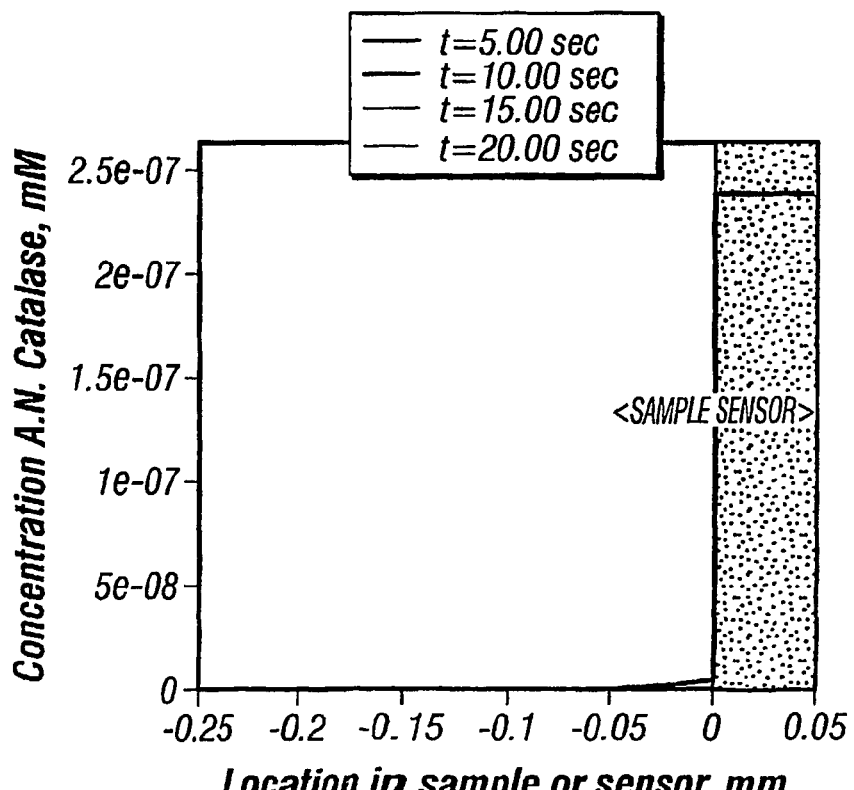

FIG. 30 shows the concentration of glucose oxidase from *Aspergillus niger* (FIG. 30a), and concentration of catalase from *Aspergillus niger* (as contaminant of GOX) (FIG. 30b) across a sample and analyte detecting member cross section. Experiments have shown that the *A. niger* enzymes are somewhat immobilized in the analyte detecting member emulsion by an as yet unknown mechanism (possibly entrapment), diffusing approximately $10^3$ times more slowly than if free. This reduction is implemented in the model, which only allows the normal diffusion speed in the sample. For the figures, Concentrations profile of enzymes are in mM.

Figure 31A:
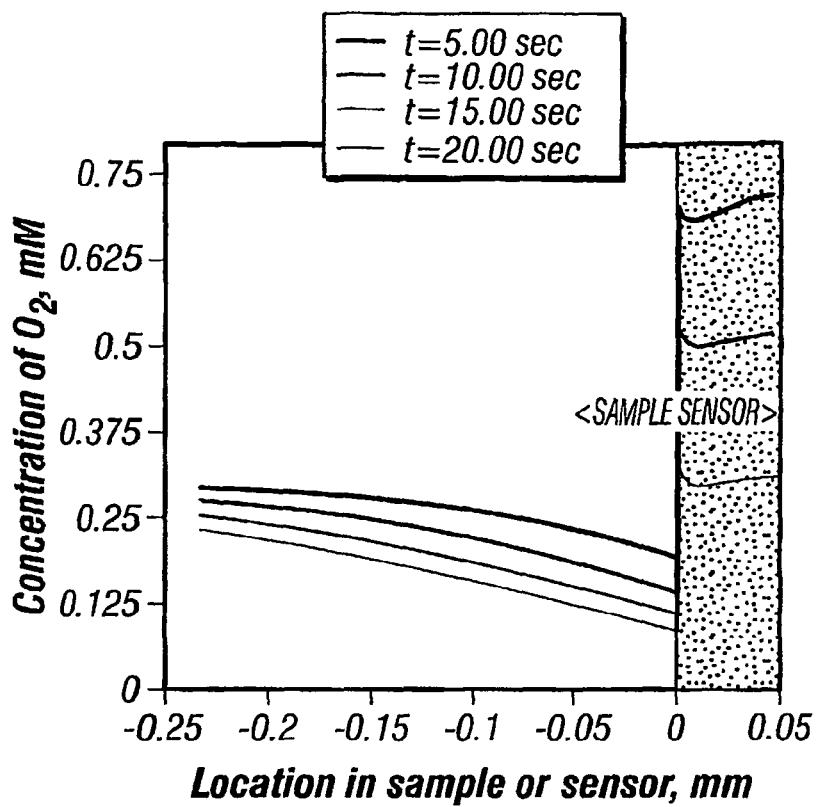
FIG. 31a through 31c are charts showing concentrations of reactants along the sample-sensor interface.
Figure 31B:
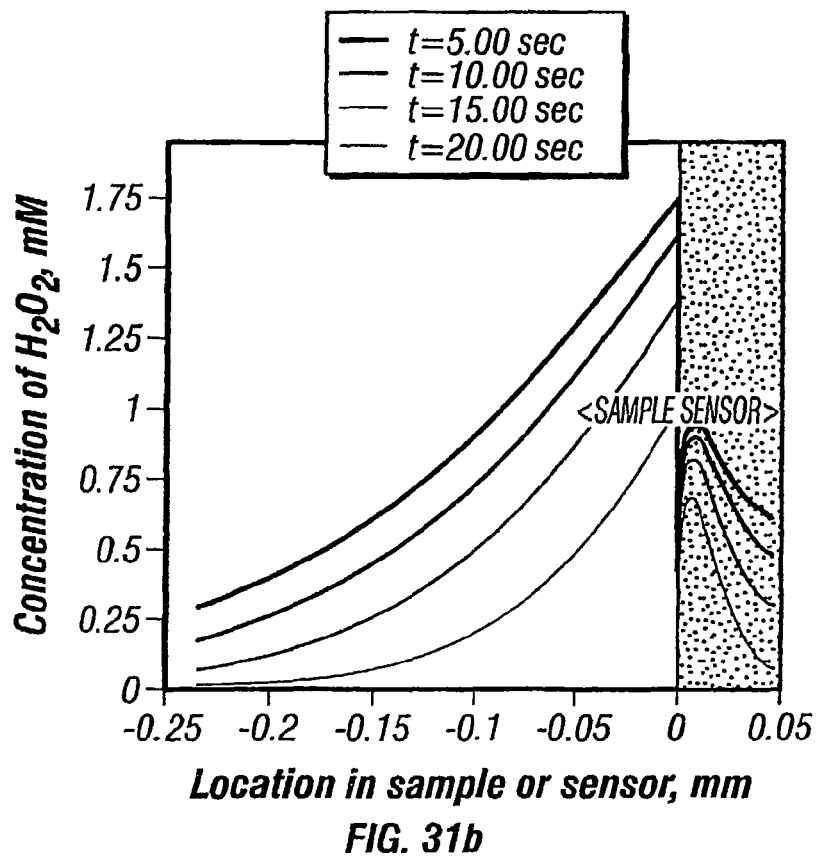
Figure 31C:
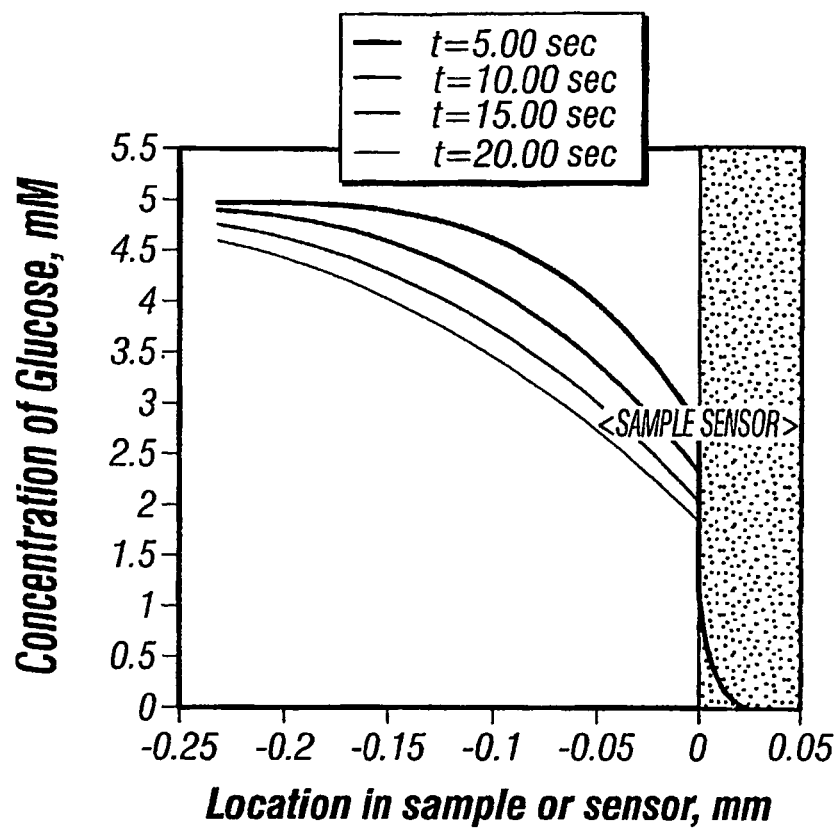

FIGS. 31a-31c show the concentrations of the reactants: oxygen, freely dissolved in sample and analyte detecting member emulsion (FIG. 31a), and hydrogen peroxide (FIG. 31b) and glucose (FIG. 31c), both freely dissolved in sample and analyte detecting member hydrophilic phase. For the figures, concentrations of reactants are in mM. These concentrations are affected by both diffusion and the consumption/production by chemical reactions over time. The decrease in oxygen concentration in the hydrophobic phase is the cause of the change in fluorescence lifetime. FIG. 31b shows an increase in hydrogen peroxide concentration produced by the glucose oxidase activity; hydrogen peroxide that diffuses into the sample largely escapes the catalase reaction.

Figure 32:
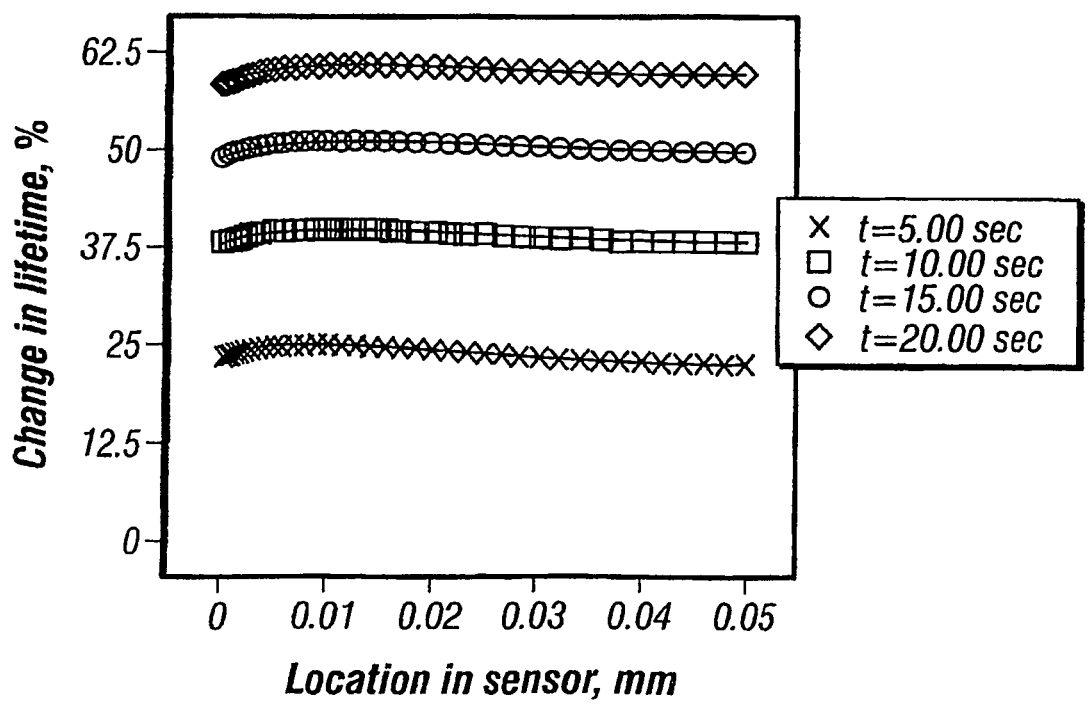
FIG. 32 is chart showing change in fluorescence lifetime as a function of analyte detecting member response to glucose.

FIG. 32 shows the change in fluorescence lifetime as a function of analyte detecting member response to glucose.

Figure 33A:
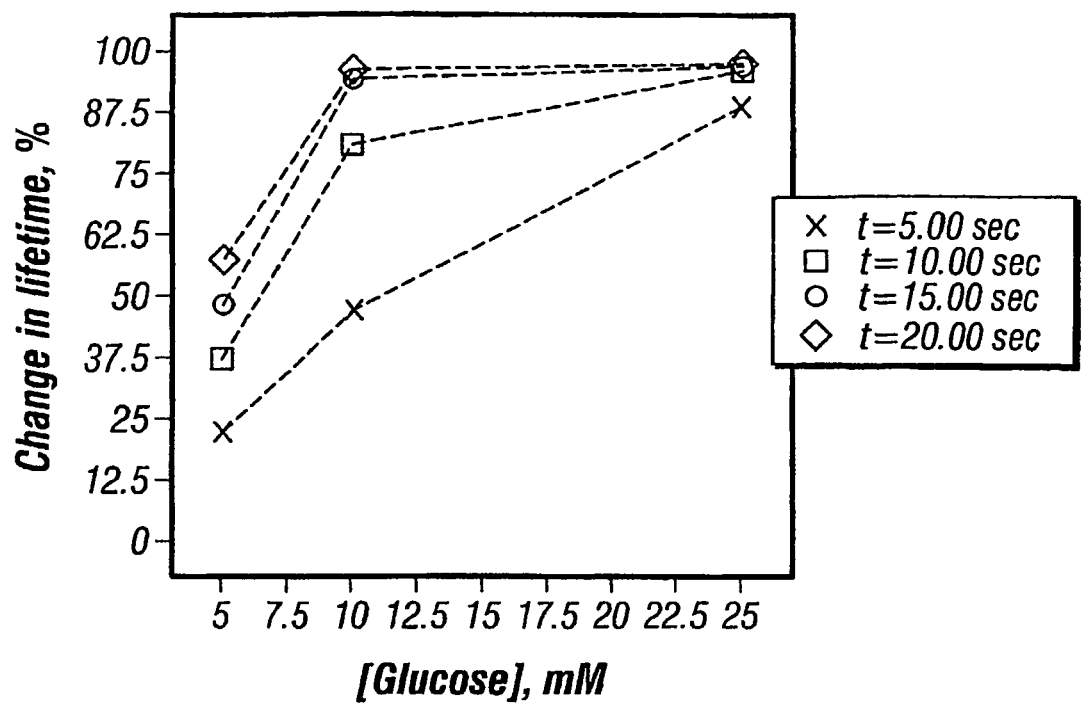
FIGS. 33a and 33b are charts showing simulated dynamic calibration (33a) and response (33b) graphs of modeled glucose analyte detecting member.
Figure 33B:
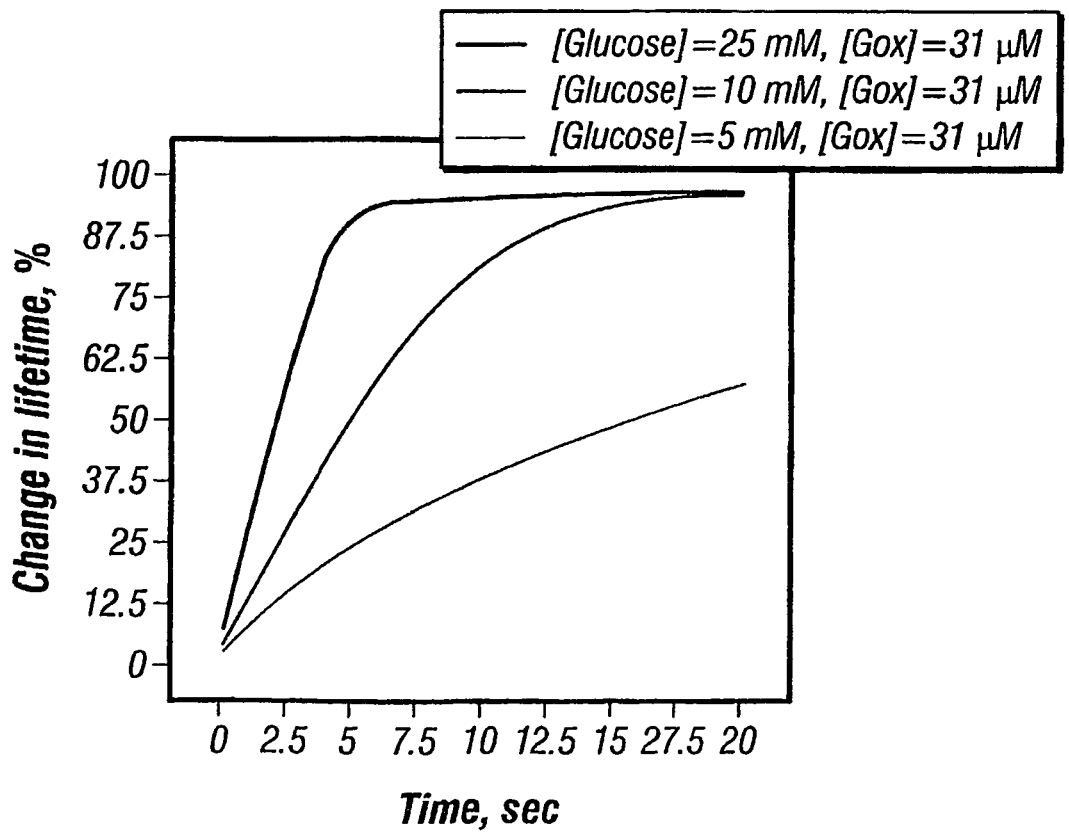

FIGS. 33a and 33b shows the simulated dynamic response of an analyte detecting member with good overall response characteristics: fast response, dynamic range in the physiologically important range, and a large enough signal change to be useful. The analyte detecting member has a hydrophobic to hydrophilic volume fraction of 40‰, an overall thickness of 47 micrometers, and 70% water in the hydrophilic phase.

FIG. 33a shows a simulated calibration graph, plotted for different times after initial analyte detecting member exposure. The analyte detecting member shows a solid response over the whole glucose range in less than 10 seconds. FIG. 33b shows simulated response curves, plotted for different glucose concentrations. In the present embodiment, the analyte detecting member reaches a plateau for the high glucose level after less than 10 seconds, while the medium and low glucose levels show an acceptable response over a similar time (in kinetic measurement mode). For reference, the normal range of glucose concentration in capillary blood is 3.5-6 mM. The 25 mM case represents an extremely high, critical glucose level. In FIG. 33b, the signal for even the high glucose level never reaches a signal of 100%, which would be equivalent to complete consumption of all oxygen present in the analyte detecting member, but rather a steady state value above 95%. The discrepancy is due to oxygen diffusion from the sample. The fact that oxygen diffusion is relatively minor is advantageous as the analyte detecting member will not be significantly sensitive to variations in oxygen concentrations in the sample.

Figure 34:
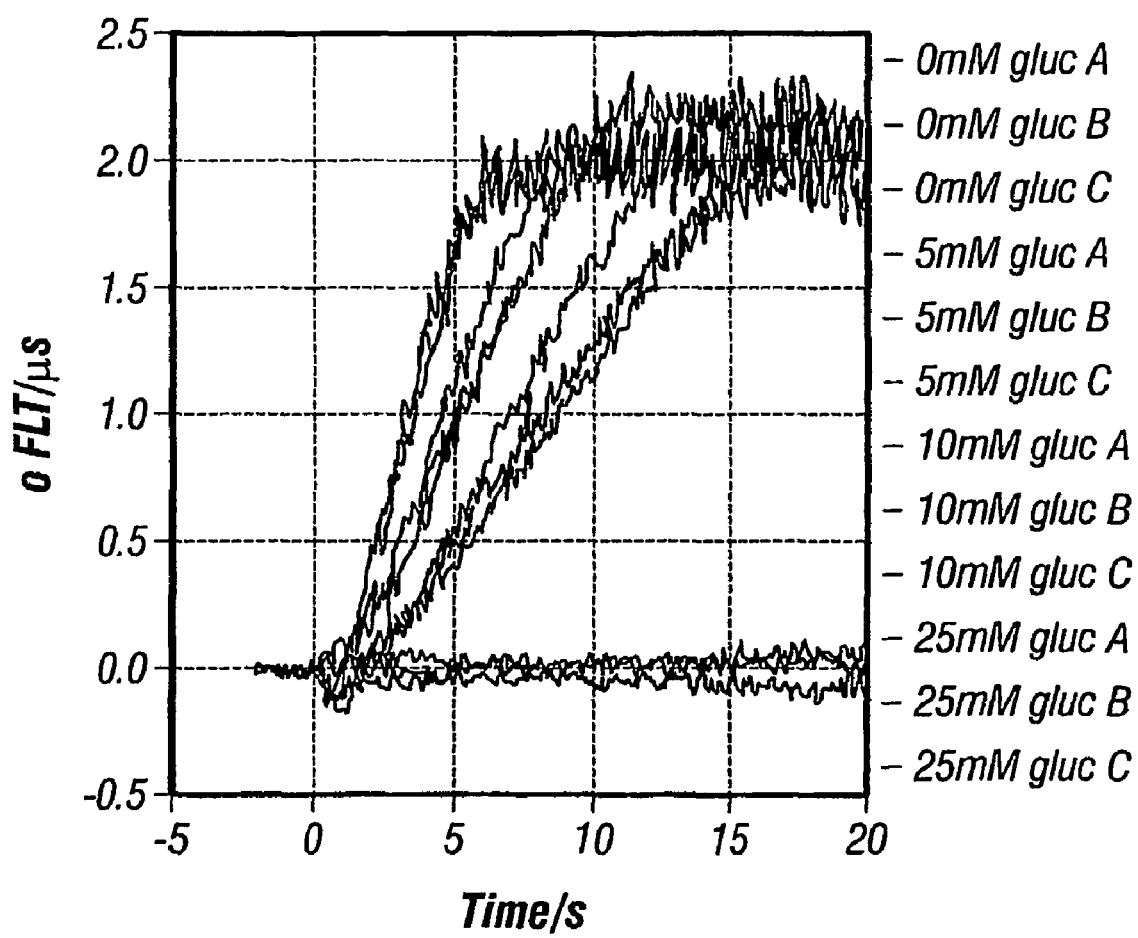
FIG. 34 shows experimentally obtained response curve of an analyte detecting member designed according to the model predictions according to the present invention.

FIG. 34 shows test data taken with a prototype analyte detecting member membrane using the same initial conditions and analyte detecting member parameters as supplied to the analyte detecting member model for the preceding figures. The predicted response (FIG. 33b) agrees with the test data, especially at the higher glucose loading. The data from the prototype membrane displays some variability and a slightly reduced dynamic range compared to that predicted.

The model was highly useful in the beginning of the development project to predict that rapid (sub-10 second) response was indeed possible (at a time when the experiments still showed response time of minutes due to material incompatibilities that were later corrected).

For the present embodiment, it was also discovered through modeling that GOX activity at concentrations higher than 3-5 mM in the analyte detecting member layer were highly non-linear, and that there was an inhibitory effect on GOX activity at those concentrations. This freed the experimental teams from trying to push the GOX concentration in the analyte detecting member to the solubility limit.

For manufacturing purposes, in some embodiments, the analyte detecting members were designed so that were less than 50 micrometers thin. The model, however, had predicted an optimum balance between response time and cross-sensitivity to sample oxygen for a analyte detecting member of approximately 100 micrometers thickness. It should be understood, of course, that various thicknesses may be used with different devices without deviating from the scope of the invention. So the model was exercised repeatedly to explore the design space; it predicted that if the GOX concentration was changed to 3 mM it would be possible to achieve a similar balance between fast response time, good dynamic range, and low cross sensitivity.

A particularly puzzling phenomenon was discovered when the experimental teams noticed a significant drop-off of glucose signal (an increase in fluorescence lifetime, or more accurately, in hybrid fluorescence phosphorescence lifetime) after only short exposure of the analyte detecting member to the sample. It was discovered through modeling that the analyte detecting member had in fact "used up" all the glucose in the sample solution, and the volume of the sample was subsequently increased.

The discussion of the various optima for the analyte detecting member and their derivation from the model are beyond the scope of this paper and will be reported elsewhere. However, based on multiple model runs and their experimental verification, we have assembled a number of qualitative design rules that should be generally applicable.

The thickness of the whole blood sample layer has no significant effect unless sample layer is very thin (<100 micrometers) and is not shielded from the atmosphere.

In one embodiment, a thinner analyte detecting member will be faster, but oxygen diffusion from the sample will start to be noticeable for analyte detecting members thinner than 100 micrometers. A higher GOX concentration can compensate for this effect. Oxygen or glucose-controlled GOX behavior is not a function of layer thickness but of the ratio between hydrophilic and hydrophobic volume and GOX concentration.

GOX concentration has to be balanced with the hydrophobic phase volume fraction to ensure a good dynamic range as well as a glucose-controlled reaction mechanism.

A ratio of hydrophilic to hydrophobic phase of 80/20 is ideal, but this can be modified as long as GOX concentration is modified as well. Increasing the ratio has three effects that beneficially enhance each other and decrease analyte detecting member response time: (a) faster diffusion of glucose in the hydrophilic phase (there is less impenetrable hydrophobic material in the way), (b) faster removal of oxygen from the hydrophobic phase (because there is less stored oxygen available), and (c) a higher amount of GOX can be used, because there is more hydrophilic phase.

Both layer thickness as well as the ratio of hydrophilic to hydrophobic phase will impact the overall fluorescence intensity that can be obtained form the analyte detecting member.

A low hydrogel polymer fraction (a higher water content) in the hydrogel yields analyte detecting members with faster response.

Catalase contamination in the hydrogel layer converts hydrogen peroxide back into oxygen, thus removing half of the oxygen-consuming effect that the consumption of glucose had on the hydrophobic layer. GOX with low catalase contamination is required.

Droplet sizes below 5 micrometers ensure oxygen diffusion inside the droplets is not a controlling parameter.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, analyte detecting members may be printed on the top, bottom, or side of the cavities. The front end of the cartridge maybe in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue. The sensory material may be deposited into the via holes. The conductor material may also be deposited into the via holes. The via holes may be formed by a variety of methods including micro drilling, laser drilling, plasma etching, or the like.

Any of the features described in this application or any reference disclosed herein may be adapted for use with any embodiment of the present invention. For example, the devices of the present invention may also be combined for use with injection penetrating members or needles as described in commonly assigned, copending U.S. patent application Ser. No. 10/127,395 filed Apr. 19, 2002. An analyte detecting member to detect the presence of foil may also be included in the lancing apparatus. For example, if a cavity has been used before, the foil or sterility barrier will be punched. The analyte detecting member can detect if the cavity is fresh or not based on the status of the barrier. It should be understood that in, optional embodiments, the sterility barrier may be designed to pierce a sterility barrier of thickness that does not dull a tip of the penetrating member. The lancing apparatus may also use improved drive mechanisms. For example, a solenoid force generator may be improved to try to increase the amount of force the solenoid can generate for a given current. A solenoid for use with the present invention may have five coils and in the present embodiment the slug is roughly the size of two coils. One change is to increase the thickness of the outer metal shell or windings surround the coils. By increasing the thickness, the flux will also be increased. The slug may be split; two smaller slugs may also be used and offset by ½ of a coil pitch. This allows more slugs to be approaching a coil where it could be accelerated. This creates more events where a slug is approaching a coil, creating a more efficient system.

In another optional alternative embodiment, a gripper in the inner end of the protective cavity may hold the penetrating member during shipment and after use, eliminating the feature of using the foil, protective end, or other part to retain the used penetrating member. Some other advantages of the disclosed embodiments and features of additional embodiments include: same mechanism for transferring the used penetrating members to a storage area; a high number of penetrating members such as 25, 50, 75, 100, 500, or more penetrating members may be put on a disk or cartridge; molded body about a lancet becomes unnecessary; manufacturing of multiple penetrating member devices is simplified through the use of cartridges; handling is possible of bare rods metal wires, without any additional structural features, to actuate them into tissue; maintaining extreme (better than 50 micron-lateral- and better than 20 micron vertical) precision in guiding; and storage system for new and used penetrating members, with individual cavities/slots is provided. The housing of the lancing device may also be sized to be ergonomically pleasing. In one embodiment, the device has a width of about 56 mm, a length of about 105 mm and a thickness of about 15 mm. Additionally, some embodiments of the present invention may be used with non-electrical force generators or drive mechanism. For example, the punch device and methods for releasing the penetrating members from sterile enclosures could be adapted for use with spring based launchers. The gripper using a frictional coupling may also be adapted for use with other drive technologies.

Still further optional features may be included with the present invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). The penetrating members may be a bare penetrating member during launch. In some embodiments, the penetrating member may be a patent needle. The same driver may be used for advancing and retraction of the penetrating member. Different analyte detecting members detecting different ranges of glucose concentration, different analytes, or the like may be combined for use with each penetrating member. Non-potentiometric measurement techniques may also be used for analyte detection. For example, direct electron transfer of glucose oxidase molecules adsorbed onto carbon nanotube powder microelectrode may be used to measure glucose levels. In some embodiments, the analyte detecting members may formed to flush with the cartridge so that a "well" is not formed. In some other embodiments, the analyte detecting members may formed to be substantially flush (within 200 microns or 100 microns) with the cartridge surfaces. In all methods, nanoscopic wire growth can be carried out via chemical vapor deposition (CVD). In all of the embodiments of the invention, preferred nanoscopic wires may be nanotubes. Any method useful for depositing a glucose oxidase or other analyte detection material on a nanowire or nanotube may be used with the present invention. Additionally, for some embodiments, any of the cartridge shown above may be configured without any of the penetrating members, so that the cartridge is simply an analyte detecting device. Still further, the indexing of the cartridge may be such that adjacent cavities may not necessarily be used serially or sequentially. As a nonlimiting example, every second cavity may be used sequentially, which means that the cartridge will go through two rotations before every or substantially all of the cavities are used. As another nonlimiting example, a cavity that is 3 cavities away, 4 cavities away, or N cavities away may be the next one used. This may allow for greater separation between cavities containing penetrating members that were just used and a fresh penetrating member to be used next. It should be understood that the spring-based drivers shown in the present invention may be adapted for use with any of the cartridges shown herein such as, but not limited to, those shown in FIGS. 61 and 62. These spring-based drivers may also be paired with gripper blocks that are configured to penetrate into cartridges that fully seal penetrating member therein, in order engage those penetrating members. The start and end positions of the penetrating members may also be the same. The penetrating members may be parked in a holder before actuation, and in some embodiments, into a holder after actuation (as seen in cartridge 500 or any other cartridge herein). Embodiments of the present invention may also include guides which provide lateral constraints and/or vertical constraints about penetrating member. These constraints may be positioned about the shaft portions of the penetrating member. For any of the embodiments herein, they may be configured to provide the various velocity profiles described. The analyte detecting members may use volumes of less than 1 microliter, less than 500 nl, 400 nl, 300 nl, 200 nl, 100 nl, 75 nl, 60 nl, 50 nl, 40 nl, 30 nl, 20 nl, 10 nl, or less of body fluid. In some embodiments, the chamber that holds the body fluid over the electrodes is less than 1 microliter, less than 500 nl, 400 nl, 300 nl, 200 nl, 100 nl, 75 nl, 60 nl, 50 nl, 40 nl, 30 nl, 20 nl, 10 nl, or less in volume. In still other embodiments, the volume of the chamber over the electrodes is less than 1 microliter, less than 500 nl, 400 nl, 300 nl, 200 nl, 100 nl, 75 nl, 60 nl, 50 nl, 40 nl, 30 nl, 20 nl, 10 nl, or less. Any of the features set forth in the present description may be combined with any other feature of the embodiments set forth above.

The publications discussed or cited herein are provided solely for their disclosure prior to the filing date of the present application. The following applications are incorporated herein by reference for all purposes: Ser. Nos. 60/507,317, 60/507,852, 60/507,845, 60/507,690, and 60/507,688. Nothing herein is to be construed as an admission that the present invention is not entitled to antedate such publication by virtue of prior invention. Further, the dates of publication provided may be different from the actual publication dates which may need to be independently confirmed. All publications and applications mentioned herein are incorporated herein by reference to disclose and describe the structures and/or methods in connection with which the publications are cited.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A body fluid sampling device comprising:
   a single cartridge;
   a plurality of penetrating members coupled to said single cartridge and operatively couplable to the penetrating member driver, said penetrating members movable to extend radially outward from the cartridge to penetrate tissue;
   a plurality of analyte detecting members coupled to said single cartridge, wherein at least one of said analyte detecting members positioned on the cartridge to receive body fluid from a wound in the tissue created by a penetrating member when the cartridge is in an operative position; and a mesh structure pushed and pierced by the penetrating member against the tissue in order to draw fluid generated by said tissue towards one of the analyte detecting members and
   wherein the mesh is a gradient mesh.

2. The device of claim 1 further comprising a ring around the cartridge wherein said analyte detecting members are mounted on said ring, along with said mesh.

3. The device of claim 1 further comprising a ring around the cartridge wherein said analyte detecting members are coupled to said cartridge through said ring.

4. The device of claim 1 further comprising a plurality of electrodes coupled to said analyte detecting member.

5. The device of claim 1 further comprising a radial cartridge, said support structure coupled to said radial cartridge.

6. The device of claim 1 further comprising a plurality of electrodes each having said sensory material.

7. The device of claim 1 wherein the texture structure is one or more of dimples, raised portions, detents, depressions, cross-hatch, scoring, criss-cross, and triangles.

8. The device of claim 1 wherein the texture structure improves user feedback and sensation of contact to let the user know whether he/she is on target.

9. The device of claim 1 wherein the mesh structure is made of capillary fibers.

10. The device of claim 1 wherein the mesh structure is pliable enough to allow relaxation.

11. The device of claim 1 wherein the mesh structure distributes impact of the penetrating member on the tissue to increase cutting efficiency of the penetrating member.

12. The device of claim 1 wherein the mesh structure reduces the amount of micropositioning used to assure that the droplet of the fluid gets to the analyte detecting member by reducing the amount of body fluid that spontaneously rises to the surface of the skin.

13. The device of claim 1 wherein the mesh structure is a hydrophilic mesh that allows the fluid built up on tissue to be absorbed.

14. A body fluid sampling device comprising:
   a single cartridge;
   a plurality of penetrating members coupled to said single cartridge and operatively couplable to the penetrating member driver, said penetrating members movable to extend radially outward from the cartridge to penetrate tissue;
   a plurality of analyte detecting members coupled to said single cartridge, wherein at least one of said analyte detecting members positioned on the cartridge to receive body fluid from a wound in the tissue created by a penetrating member when the cartridge is in an operative position; and a mesh structure pushed and pierced by the penetrating member against the tissue in order to draw fluid generated by said tissue towards one of the analyte detecting members; and
   wherein the mesh structure is a gradient type of mesh designed and patterned to create a desired movement of fluid in contact with the mesh.

* * * * *